United States Patent
Brar et al.

(10) Patent No.: US 11,421,232 B2
(45) Date of Patent: *Aug. 23, 2022

(54) COMPOSITIONS AND METHODS FOR TREATMENT OF CARDIAC DISEASES

(71) Applicant: Jaan Biotherapeutics LLC, San Diego, CA (US)

(72) Inventors: Bhawanjit Kaur Brar, La Jolla, CA (US); Eric G. Marcusson, San Francisco, CA (US)

(73) Assignee: Jaan Biotherapeutics LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/397,713

(22) Filed: Aug. 9, 2021

(65) Prior Publication Data

US 2022/0033819 A1  Feb. 3, 2022

Related U.S. Application Data

(63) Continuation of application No. 16/990,470, filed on Aug. 11, 2020, now Pat. No. 11,124,793, which is a continuation of application No. 16/318,353, filed as application No. PCT/US2017/042400 on Jul. 17, 2017.

(60) Provisional application No. 62/419,852, filed on Nov. 9, 2016, provisional application No. 62/363,512, filed on Jul. 18, 2016.

(51) Int. Cl.
    *C12N 15/113* (2010.01)
    *A61P 9/00* (2006.01)
    *A61K 31/7088* (2006.01)
    *A61K 45/06* (2006.01)

(52) U.S. Cl.
    CPC ........ *C12N 15/113* (2013.01); *A61K 31/7088* (2013.01); *A61K 45/06* (2013.01); *A61P 9/00* (2018.01); *C12N 2310/113* (2013.01); *C12N 2310/141* (2013.01); *C12N 2310/315* (2013.01); *C12N 2310/3231* (2013.01); *C12N 2310/344* (2013.01); *C12N 2310/346* (2013.01); *C12N 2750/14143* (2013.01)

(58) Field of Classification Search
    CPC ....... A61K 31/7088; A61K 45/06; A61P 9/00; C12N 15/113; C12N 2310/113; C12N 2310/141; C12N 2310/315; C12N 2310/3231; C12N 2310/344; C12N 2310/346; C12N 2320/31; C12N 2750/14143
    USPC .............................. 514/44 A; 435/375, 455
    See application file for complete search history.

(56) References Cited

U.S. PATENT DOCUMENTS

| | | | |
|---|---|---|---|
| 9,771,579 B2 * | 9/2017 | Collard | A61P 25/02 |
| 10,202,600 B2 | 2/2019 | Gao et al. | |
| 2006/0185027 A1* | 8/2006 | Bartel | C12N 15/111 800/14 |
| 2007/0092882 A1* | 4/2007 | Wang | C12Q 1/6837 435/6.11 |
| 2009/0306181 A1 | 12/2009 | Ikeda et al. | |
| 2014/0221463 A1 | 8/2014 | Aguirre et al. | |
| 2015/0232637 A1 | 8/2015 | Cha et al. | |
| 2015/0232837 A1* | 8/2015 | Thibonnier | A61P 29/00 514/44 A |

FOREIGN PATENT DOCUMENTS

| | | | | |
|---|---|---|---|---|
| WO | WO2004041177 A2 | 5/2004 | | |
| WO | WO-2005040419 A1 * | 5/2005 | ........... | C12Q 1/6886 |
| WO | WO2005040419 A1 | 5/2005 | | |
| WO | WO2007112754 A2 | 10/2007 | | |
| WO | WO2009012468 A2 | 1/2009 | | |
| WO | WO2010135570 A1 | 11/2010 | | |

OTHER PUBLICATIONS

Ma et al. (Intrinsic Features in MicroRNA Transcriptomes Link Porcine Visceral Rather than Subcutaneous Adipose Tissues to Metabolic Risk) PLoS, vol. 8, No. 11, pp. 1-9. (Year: 2013).*
Lagos-Quintana et al. (2002), Current Biology, vol. 12, pp. 735-739. Apr. 30, 2002. (Year: 2002).*
Addis & Epstein, "Induced regeneration—the progress and promise of direct reprogramming for heart repair," Nat Med 2013, 19(7), in 17 pages.
Aguirre et al., "Reprogramming toward Heart Regeneration: Stem Cells and Beyond," Cell Stem Cell 2013, 12, 275-284.
Aguirre et al., "In vivo activation of a conserved microRNA program induces robust mammalian heart regeneration," Cell Stem Cell 2014, 15(5), 589-604.
Alrefai et al., "Cardiac tissue engineering and regeneration using cell-based therapy," Stem Cells and Cloning: Advances and Applications 2015, 8, 81-101.
Ambros, "The functions of animal microRNAs," Nature 2004, 431, 350-355.

(Continued)

*Primary Examiner* — Janet L Epps -Smith
(74) *Attorney, Agent, or Firm* — Sheppard, Mullin, Richter & Hampton LLP

(57) ABSTRACT

Disclosed herein include microRNA antagonists, therapeutic compositions that include one or more of such microRNA antagonists, and methods of treating and/or ameliorating cardiac diseases and/or muscular dystrophy disorders with the microRNA antagonists. Also included are combination therapies, wherein a therapeutic composition disclosed herein and an additional therapy agent are provided to a subject having or suspected of having cardiac disease and/or muscular dystrophy disorder. In particular, some embodiments disclosed herein relate to compositions and methods for transiently administering a mixture of microRNA antagonists for promoting cardiomyocyte proliferation and cardiac regeneration.

18 Claims, 19 Drawing Sheets

Specification includes a Sequence Listing.

(56) References Cited

OTHER PUBLICATIONS

Angelini, "The role of corticosteroids in muscular dystrophy: A critical appraisal," Muscle and Nerve 2007, 36, 424-435.
ATS Consensus Statement, "Respiratory Care of the Patient with Duchenne Muscular Dystrophy," Am J Respir Crit Care Med 2004, 170, 456-465.
Axtell & Bartel, "Antiquity of MicroRNAs and Their Targets in Land Plants," The Plant Cell 2005, 17, 1658-1673.
Azevedo, "Duchenne MD Therapy Showing Potential in Initial Clinical Trial," Muscular Dystrophy 2016, in 2 pages, https://musculardystrophynews.com/2016/01/27/catabasis-pharmaceuticals-announces-positive-top-line-results-from-part-a-of-the-movedmdsm-trial-a-phase-1-2-trial-of-cat-1004-for-the-treatment-of-duchenne-muscular-dystrophy/.
Bajek et al., "Cell Therapy in Duchenne Muscular Dystrophy Treatment: Clinical Trials Overview," Critical Reviews in Eukaryotic Gene Expression 2015, 25(1), 1-11.
Bale et al., "The cardiovascular physiologic actions of urocortin II:Acute effects in murine heart failure," PNAS 2004, 101(10), 3697-3702.
Bartel, "MicroRNAs: Genomics, Biogenesis, Mechanism, and Function," Cell 2004, 116, 281-297.
Bartel, "MicroRNA Target Recognition and Regulatory Functions," Cell 2009, 136(2), 215-233.
Beltrami et al., "Evidence that Human Cardiac Myocytes Divide After Myocaridal Infection," The New England Journal of Medicine 2001, 344(23), 1750-1757.
Bentwich et al., "Identification of hundreds of conserved and nonconserved human microRNAs," Nature Genetics 2005, 37(7), 766-770.
Bersell et al.. "Neuregulin1/ErbB4 Signaling Induces Cardiomyocyte Proliferation and Repair of Heart Injury," Cell 2009, 138, 257-270.
Bogdanovich et al., "Functional improvement of dystrophic muscle by myostatin blockade," Nature 2002, 420, 418-421.
Bonuccelli et al., "Localized Treatment with a Novel FDA—Approved Proteasome Inhibitor Blocks the Degradation of Dystrophin and Dystrophin—Associated Proteins in mdx Mice," Cell Cycle 2007, 6(10), 1242-1248.
Bushby et al., "Report on the 124th ENMC International Workshop. Treatment of Duchenne muscular dystrophy; defining the gold standards of management in the use of corticosteroids," Neuromuscular Disorders 2004, 14, 526-534.
Bushby et al., "Diagnosis and management of Duchenne muscular dystrophy, part 1: diagnosis, and pharmacological and psychosocial management," The Lancet Neurol 2010, 9, 77-93.
Bushby et al., "The multidisciplinary management of Duchenne muscular dystrophy," Current Pediatrics 2005, 15(4), 292-300.
Buyse et al., "Idebenone as a Novel Therapeutic Approach for Duchenne Muscular Dystrophy," Neuromuscular Disorders 2015, 10(2), 189-194.
Buyse et al., "Efficacy of idebenone on respiratory function in patients with Duchenne muscular dystrophy not using glucocorticoids (DELOS): a double-blind randomised placebo-controlled phase 3 trial," Lancet 2015, 385, 1748-1757.
Capogrosso et al., "Assessment of resveratrol, apocynin and taurine on mechanical-metabolic uncoupling and oxidative stress in a mouse model of duchenne muscular dystrophy: A comparison with the gold standard, a-methyl prednisolone," Pharmacol Res 2016, 106, 101-113.
Chen & Rajewsky, "The evolution of gene regulation by transcription factors and microRNAs," Nature Reviews 2007, 8, 93-103.
Chendrimada et al., "TRBP recruits the Dicer complex to Ago2 for microRNA processing and gene silencing," Nature Publishing Group 2005, 436, 740-744.
Chicoine et al., "Vascular Delivery of rAAVrh74.MCK. GALGT2 to the Gastrocnemius Muscle of the Rhesus Macaque Stimulates the Expression of Dystrophin and Laminin α2 Surrogates," American Academy of Pediatrics 2005, 116(6), 1569-1573.
Chu et al., "Direct comparison of efficiency and stability of gene transfer into the mammalian heart using adeno-associated virus versus adenovirus vectors," The Journal of Thoracic and Cardiovascular Surgery 2003, 126(3), 671-679.
Cirak et al., "Exon skipping and dystrophin restoration in patients with Duchenne muscular dystrophy after systemic phosphorodiamidate morpholino oligomer treatment: an open-label, phase 2, dose-escalation study," Lancet 2011, 37(8), 595-605.
Cittadini et al., "A preliminary randomized study of growth hormone administration in Becker and Duchenne muscular dystrophies," European Heart Journal 2003, 24, 664-672.
Coppola et al., "Cardiomyogenesis is controlled by the miR-99a/let-7c cluster and epigenetic modifications," Stem Cell Research 2014, 12, 323-337.
Corrected Notice of Allowability dated Aug. 8, 2021 in U.S. Appl. No. 16/990,470.
Couzin, "Small RNAs Make Big Splash," Science 2002, 298(5602), 2296-2297.
Cripe et al., "Cardiovascular Health Supervision for Individuals Affected by Duchenne or Becker Muscular Dystrophy," American Academy of Pediatrics 2005, 116(6), 1569-1573.
Dennis, "The genome's guiding hand?," Nature 2002, 420, 732.
Di Mauro et al., "Distribution of costameric proteins in normal human ventricular and atrial cardiac muscle," Folia Histochem Cytobiol 2009, 47(4), 605-608.
Duboc et al. "Perindopril preventive treatment on mortality in Duchenne muscular dystrophy: 10 years' follow-up," American Heart Journal 2007, 154(3), 596-602.
Duggan et al., "Mutations in the Sarcoglycan Genes in Patients with Myopathy," The New England Journal of Medicine 1997, 336(9), 618-624.
Emery, "The muscular dystrophies," The Lancet 2002, 359, 687-695.
Escolar et al., "CINRG randomized controlled trial of creatine and glutamine in Duchenne muscular dystrophy," Ann Neurol. 2005, 58(1), 151-155.
Extended European Search Report dated Mar. 13, 2020 in European Patent Application No. 17831634.5.
Fabian et al., "Regulation of mRNA translation and stability by MicroRNAs," Annual review of biochemistry 2010, 79, 351-379.
Fayssoil et al., "Cardiomyopathy in Duchenne muscular dystrophy: pathogenesis and therapeutics," Heart Fail Rev 2010, 15, 103-107.
Fazi et al., "A Minicircuitry Comprised of MicroRNA-223 and Transcription Factors NFI-A and C/EBP∝ Regulates Human Granulopoiesis," Ceil 2005, 123, 819-831.
Fechner et al., "Cardiac-targeted RNA interference mediated by an AAV9 vector improves cardiac function in coxsackievirus B3 cardiomyopathy," J Mol Med 2008, 86, 987-997.
Finkel, "Readthrough Strategies for Suppression of Nonsense Mutations in Duchenne/Becker Muscular Dystrophy: Aminoglycosides and Ataluren (PTC124)," J Child Neurol 2010, 25(9), 1158-1164.
Flotte & Carter, "Adeno-Associated Viral Vectors," Gene Therapy Technologies, Applications and Regulations 1999, 109-125.
Friedman et al., "Most mammalian mRNAs are conserved targets of microRNAs," Genome Research 2009, 19, 92-105.
Geary et al., "Pharmacokinetics, biodistribution and cell uptake of antisense oligonucleotides," Advanced Drug Delivery Reviews 2015, 87, 46-51.
Giometti et al., "Muscle Protein Analysis. II. Two-Dimensional Electrophoresis of Normal and Diseased Human Skeletal Muscle," Clin Chem 1980, 26(8), 1152-1155.
Gregory et al., "The Microprocessor complex mediates the genesis of microRNAs," Nature 2004, 432, 235-240.
Gu et al., "Urocortin 2 Lowers Blood Pressure and Reduces Plasma Catecholamine Levels in Mice with Hyperadrenergic Activity," Endocrinology 2010, 151(10), 4820-4829.
Guiraud et al., "The Pathogenesis and Therapy of Muscular Dystrophies," Annu Rev Genom 2015, 16(13), 1-13.
Haraguchi et al., "Vectors expressing efficient RNA decoys achieve the long-term suppression of specific microRNA activity in mammalian cells," Nucleic Acids Research 2009, 37(6), e43, in 13 pages.
Hogan et al., "Anti-miRs Competitively Inhibit microRNAs in Argonauts Complexes," PLOS ONE 2014, 9(7), e100951, in 11 pages.

(56) References Cited

OTHER PUBLICATIONS

International Search Report and Written Opinion, dated Oct. 23, 2017, in International Application No. PCT/US2017/042400.
Jopling et al., "Zebrafish heart regeneration occurs by cardiomyocyte dedifferentiation and proliferation," Nature 2010, 464, 606-609.
Kawecka et al., "Adeno-Associated Virus (AAV) Mediated Dystrophin Gene Transfer Studies and Exon Skipping Strategies for Duchenne Muscular Dystrophy (DMD)," Current Gene Therapy 2015, 15, 395-415.
Kidner & Martienssen, "Macro effects of microRNAs in plants," TRENDS in Genetics 2003, 19(1), 13-16.
Kikuch et al., "Primary contribution to zebrafish heart regeneration by gata4+ cardiomyocytes," Nature 2010, 464, 601-605.
Klietsch et al., "Dystraphin-Glycoprotein Complex and Laminin Colocalize to the Sarcolemma and Transverse Tubules of Cardiac Muscle," Circulation Research 1993, 72, 349-360.
Koenig et al.,"Complete cloning of the Duchenne muscular dystrophy (DMD) cDNA and preliminary genomic organization of the DMD gene in normal and affected individuals," Cell 1987, 50(3), p. 509-517.
Koenig & Kunkel, "The complete sequence of dystrophin predicts a rod-shaped cytoskeletal protein," Cell 1988, 53(2), 219-228.
Koo & Wood, "Clinical trials using antisense oligonucleotides in duchenne muscular dystrophy," Hum Gene Therapy 2013, 24(5), 479-488.
Kragl et al., "Cells keep a memory of their tissue origin during axolotl limb regeneration," Nature 2009, 460, 60-65.
Ku & McManus, "Behind the Scenes of a Small RNA Gene—Silencing Pathway," Hum Gene Ther. 2008, 19, 17-26.
Lagos-Quintana et al., "Identification of Tissue-Specific MicroRNAs from Mouse," Current Biology 2002, 12(9), 735-739.
Laflamme & Murry, "Heart regeneration," Nature 2011, 473, 326-335.
Lee et al., "The C. elegans Heterochronic Gene lin-4 Encodes Small RNAs with Antisense Complementarity to lin-14," Cell 1993, 75, 843-854.
Lee et al., "MicroRNA genes are transcribed by RNA polymerase II," The EMBO Journal 2004, 23, 4051-4060.
Lee et al., "Evolutionary Conservation of MicroRNA Regulatory Circuits: An Examination of MicroRNA Gene Complexity and Conserved MicroRNA-Target Interactions through Metazoan Phylogeny," DNA and Cell Biology 2007, 26(4), 209-218.
Lewis et al., "Conserved Seed Pairing, Often Flanked by Adenosines, Indicates that Thousands of Human Genes are MicroRNA Targets," Cell 2005, 120, 15-20.
Li et al., "Sub-physiological sarcoglycan expression contributes to compensatory muscle protection in mdx mice," Human Molecular Genetics 2009, 18(7), 1209-1220.
Liebson, "Stem-Cell Angiogenesis and Regeneration of the Heart: Review of a Saga of 2 Decades," Clin Cardiol 2015, 38(5), 309-316.
Long et al., "Postnatal genome editing partially restores dystrophin expression in a mouse model of muscular dystrophy," Science 2016, 351(6271), 400-403.
Ma, J., et al., Intrinsic Features in MicroRNA Transcriptomes Link Porcine Visceral Rather than Adipose Tissue to Metabolic Risk, PLOS One, vol. 8, No. 11, e80041, 2011.
Madsen et al., "Adeno-associated virus serotype 2 induces cell-mediated immune responses directed against multiple epitopes of the capsid protein VP1," Journal of General Virology 2009, 90, 2622-2633.
Maiweilidan et al., "Novel interactions of ankyrins-G at the costameres: The muscle-specific Obscurin/Titin-Binding-related Domain (OTBD) binds plectin and fiiamin C," Experimental Cell Research 2011, 317(6), 724-736.
Matsumura et al., "Association of dystrophin-related protein with dystrophin-associated proteins in mdx mouse muscle," Nature 1992, 360, 588-591.
Mendell et al., "Clinical investigation of Duchenne muscular dystrophy. A methodology for therapeutic trials based on natural history controls," Archives of Neurology 1987, 44(8), 808-811.

Mendell et al., "LGMD 2D gene therapy restores alpha-sarcoglycan and associated proteins," Ann Neurol 2009, 66(3), 290-297.
Mendell et al., "Dystrophin Immunity in Duchenne's Muscular Dystrophy," The New England Journal of Medicine 2010, 363(13), 1429-1437.
Mendell et al., "Sustained alpha-sarcoglycan gene expression following gene transfer in LGMD2D," Ann Neural 2010, 68(5), 629-638.
Mendell et al., "Eteplirsen for the Treatment of Duchenne Muscular Dystrophy," Ann Neurol 2013, 74, 637-647.
Mendell et al., "Longitudinal Effect of Eteplirsen versus Historical Control on Ambulation in Duchenne Muscular Dystrophy," Ann Neurol 2016, 79, 257-271.
Miyazaki et al., "Heart Failure-Inducible Gene Therapy Targeting Protein Phosphatase 1 Prevents Progressive Left Ventricular Remodeling," PLoS ONE 2012, 7(4), e35875, in 13 pages.
Mok et al., "Lack of Functional Benefit with Glutamine versus Placebo in Duchenne Muscular Dystrophy: A Randomized Crossover Trial," PLoS ONE 2009, 4(5), e5448, in 8 pages.
Monaco et al., "An explanation for the phenotypic differences between patients bearing partial deletions of the DMD locus," Genomics 1988, 2(1), 90-95.
Muntoni & Torelli, "A Dystrophin and mutations: one gene, several proteins, multiple phenotypes," Lancet Neurol 2003, 2(12), 731-740.
Negro et al., "erbB2 is required for G protein-coupled receptor signaling in the heart," PNAS 2006, 103(43), 15889-15893.
Nelson et al., "In viva genome editing improves muscle function in a mouse model of Duchenne muscular dystrophy," Science 2016, 351(6271), 403-407.
Non-Final Office Action dated Mar. 29, 2021 in U.S. Appl. No. 16/990,470.
Notice of Allowance dated Jul. 27, 2021 in U.S. Appl. No. 16/990,470.
Nowbar et al., "Discrepancies in autologous bone marrow stem cell trials and enhancement of ejection fraction (DAMASCENE): weighted regression and meta-analysis," BMJ 2014, 348, in 9 pages.
Núñez-García, "Second-generation stem cells for cardiac repair," World Journal of Stem Cells 2015, 7(2), 352-367.
O'Donnell et al., "c-Myc-regulated microRNAs modulate E2F1 expression," Nature 2005, 435, 839-843.
Park et al., "AAV-Mediated Knock-Down of HRC Exacerbates Transverse Aorta Constriction-Induced Heart Failure," PLoS ONE 2012, 7(8), e43282, in 17 pages.
Pashmforoush et al., "Adult mice deficient in actinin-associated LIM—domain protein reveal a developmental pathway for right ventricular cardiomyopathy," Nature Medicine 2001, 7(5), 591-597.
Pasquinelli et al., "MicroRNAs: a developing story," Curr. Opin. Genet. Dev. 2005, 15, 200-205.
Peterson et al., "MicroRNAs and metazoan macroevolution: insights into canalization, complexity, and the Cambrian explosion," BioEssays 2009, 31(7), 736-747.
Piras et al., "Systemic Delivery of shRNA by AAV9 Provides Highly Efficient Knockdown of Ubiquitously Expressed GFP in Mouse Heart, but Not Liver," PLoS ONE 2013, 8(9), e75894, in 11 pages.
Porello et al., "Transient Regenerative Potential of the Neonatal Mouse Heart," Science 2011, 331(6020), 1078-7080.
Posner et al., "The Correlation of Skeletal and Cardiac Muscle Dysfunction in Duchenne Muscular Dystrophy," J Neuromuscular Disorders 2016, 3(1), 91-99.
Prasad et al., "Robust cardiac myocyte-specific gene expression following systemic injection of AAV: in vivo gene delivery follows a Poisson distribution," Gene Therapy 2011, 18, 43-52.
Protti et al., "Late Gadolinium Enhancement of Acute Myocardial Infarction in Mice at 7T: Cine-FLASH Versus Inversion Recovery," Journal of Magnetic Resonance Imaging 2010, 32, 878-886.
Protti et al., "MRI-based prediction of adverse cardiac remodeling after murine myocardial infarction," Am J Physiol Heart Circ Physiol 2012, 303, H309-H314.
Quinlivan et al., "Report of a Muscular Dystrophy Campaign funded workshop Birmingham, UK, Jan. 16, 2004, Osteoporosis in Duchenne muscular dystrophy; its prevalence, treatment and prevention," Neuromuscular Disorders 2005, 15, 72-79.

(56) References Cited

OTHER PUBLICATIONS

Rahimov & Kunkel, "Cellular and molecular mechanisms underlying muscular dystrophy," J Cell Biol 2013, 201(4), 499-510.
Raman et al., "Eplerenone for early cardiomyopathy in Duchenne muscular dystrophy: a randomised, double-blind, placebo-controlled trial," Lancet Neurol 2015, 14(2), 153-161.
Restriction Requirement dated Jan. 6, 2021 in U.S. Appl. No. 16/990,470.
Ricotti et al., "Safety, Tolerability, and Pharmacokinetics of SMT C1100, a 2-Arylbenzoxazole Utrophin Modulator, following Single- and Multiple-Dose Administration to Pediatric Patients with Duchenne Muscular Dystrophy," PloS ONE 2016, 11(4), e0152840, in 16 pages.
Ryan et al., "Ataluren: First Global Approval," Drugs 2014, 74, 1709-1714.
Saccone et al., "HDAC—regulated myomiRs control BAF60 variant exchange and direct the functional phenotype of fibro-adipogenic progenitors in dystrophic muscles," Genes and Development 2013, 28, 841-857.
Scott et al., "Viral vectors for gene transfer of micro-, mini-, or full-length dystrophin," Neuromuscular Disorders 2002, 12, S23-S29.
Sienkiewicz et al., "Duchenne muscular dystrophy: current cell therapies," Ther Adv Neurol Disord 2015, 8(4), 166-177.
Song et al., "Multiple shRNA expressing vector enhances efficiency of gene silencing," BMB reports 2008, 41(5), 358-362.
Song et al., "Antibody mediated in vivo delivery of small interfering RNAs via cell-surface receptors," Nature Biotechnology 2005, 23(6), 709-717.
Tabebordbar et al., "In vivo gene editing in dystrophic mouse muscle and muscle stem cells," Science 2016, 351(6271), 407-411.
Tanzer et al., "Molecular Evolution of a MicroRNA Cluster," J. Mol. Biol. 2004, 339, 327-335.
Tzahor & Poss, "Cardiac regeneration strategies: Staying young at heart," Science 2017, 356, 1035-1039.
U.S. National Library of Medicine, "Phase I/II Study of PRO044 in Duchenne Muscular Dystrophy (DMD)," BioMarin Pharmaceutical, Accessed Jan. 12, 2021, in 8 pages. https://ciinicaltrials.gov/ct2/show/NCT01037309.
U.S. National Library of Medicine, "Efficacy and Safety of Human Neuregulin-1 to Treat Stable Chronic Heart Failure(ZS-01-210)," Zensun Sci. & Tech. Co., Ltd. Accessed Jan. 12, 2021, in 8 pages. https://clinicaltrials.gov/ct2/show/NCT01251406?term=Zensun&rank=2).
U.S. National Library of Medicine, Search Results "Duchenne," dated Jan. 12, 2021, in 3 pages. https://clinicaltrials.gov/ct2/results?term=Duchenne&Search=Search.
U.S. National Library of Medicine, Search Results "Duchenne," dated Jan. 12, 2021, in 2 pages. https://clinicaltrials.gov/ct2/results?term=Duchenne&recr=Open&type=Intr&rslt=&age_v=&gndr=&cond=&intr=&titles=&outc=&spons=&lead=&id=&statel=&entryl=&state2=&entry2=&state3=&entry3=&locn=&rc v s=&rcv e=&lup_s=&lup_e=.
Wagner et al., "A Phase I/II trial of MYO-029 in Adult Subjects with Muscular Dystrophy," Ann Neurol 2008, 63, 561-571.
Webster et al., "Fast Muscle Fibers Are Preferentially Affected in Duchenne Muscular Dystrophy," Cell 1988, 52, 503-513.
Wright, "Transient Transfection Methods for Clinical Adeno-Associated Viral Vector Production," Human Gene Therapy 2009, 20, 698-706.
Xie et al., "Long-term, efficient inhibition of microRNA function in mice using rAAV vectors," Nature Methods 2012, 9(4), 403-409.
Zaiss & Muruve, "Immune Responses to Adeno-Associated Virus Vectors," Current Gene Therapy 2005, 5(3), 323-331.
Zeng & Cullen, "Sequence requirements for micro RNA processing and function in human cells," RNA 2003, 9, 112-123.
Zhang et al., "In vivo cardiac reprogramming contributes to zebrafish heart regeneration," Nature 2013, 498, 497-501.
Zolotukhin et al., "Recombinant adeno-associated virus purification using novel methods improves infectious titer and yield," Gene Therapy 1999, 6, 973-985.
Non-Final Office Action dated May 12, 2022 in U.S. Appl. No. 16/318,353.
Office Action dated Mar. 3, 2022 in Chinese Patent Application No. 201780057449.3.

\* cited by examiner

| Term | Count | Count | % | P-Value |
|---|---|---|---|---|
| Cardiac muscle contraction | | 15 | 9.1 | 3.00E-10 |
| Hypertrophic cardiomyopathy (HCM) | | 14 | 8.5 | 9.00E-09 |
| Dilated cardiomyopathy | | 14 | 8.5 | 2.80E-08 |
| | Count | Count | % | P-Value |
| muscle contraction | | 11 | 6.7 | 3.80E-10 |
| muscle system process | | 11 | 6.7 | 1.20E-09 |
| striated muscle contraction | | 8 | 4.8 | 2.70E-09 |
| | Count | Count | % | P-Value |
| myofibril | | 14 | 8.5 | 1.20E-10 |
| contractile fiber | | 14 | 8.5 | 2.10E-10 |
| contractile fiber part | | 13 | 7.9 | 8.60E-10 |
| sarcomere | | 12 | 7.3 | 5.20E-09 |
| keratin filament | | 11 | 6.7 | 7.40E-09 |
| myosin filament | | 7 | 4.2 | 1.80E-08 |
| intermediate filament | | 14 | 8.5 | 2.10E-08 |
| intermediate filament cytoskeleton | | 14 | 8.5 | 2.70E-08 |
| striated muscle thick filament | | 5 | 3 | 1.70E-06 |
| muscle myosin complex | | 5 | 3 | 5.10E-06 |
| cytoskeletal part | | 27 | 16.4 | 5.30E-06 |
| myosin II complex | | 5 | 3 | 1.20E-05 |
| actin cytoskeleton | | 13 | 7.9 | 1.30E-05 |
| striated muscle thin filament | | 4 | 2.4 | 6.90E-05 |
| cytoskeleton | | 31 | 18.8 | 7.80E-05 |
| myosin complex | | 7 | 4.2 | 1.20E-04 |

*FIG. 14*

COMPOSITIONS AND METHODS FOR TREATMENT OF CARDIAC DISEASES

CROSS-REFERENCE TO RELATED APPLICATIONS

This application is a continuation of U.S. Application Ser. No. 16/990,470, filed on Aug. 11, 2020, which is a continuation of U.S. application Ser. No. 16/318,353 filed on Jan. 16, 2019, which is the U.S. National Phase under 35 U.S.C. § 371 of International Application No. PCT/US2017/042400 filed on Jul. 17, 2017 designating the U.S., which claims the benefit of priority to U.S. Provisional Patent Application Ser. No. 62/363,512, filed on Jul. 18, 2016, and U.S. Provisional Patent Application Ser. No. 62/419,852, filed on Nov. 9, 2016. The disclosures of the above-related applications are herein expressly incorporated by reference it their entireties, including any drawings.

STATEMENT REGARDING FEDERALLY SPONSORED R&D

The present application was made in part with government support under Grant No. R41HL134387 and GRANT12233027 awarded by the National Heart, Lung, And Blood Institute of the National Institutes of Health. The government has certain rights in the invention.

REFERENCE TO SEQUENCE LISTING

The present application is being filed along with a Sequence Listing in electronic format. The Sequence Listing is provided as a file entitled "SequenceListing", created Aug. 11, 2020, which is approximately 60 KB in size. The information in the electronic format of the Sequence Listing is incorporated herein by reference in its entirety.

FIELD

Aspects of the present application relate to the fields of biochemistry and medicine. More particularly, disclosed herein are novel microRNA antagonists, therapeutic compositions that include one or more of such microRNA antagonists, and methods of treating and/or ameliorating cardiac diseases and/or muscular dystrophy disorders with such microRNA antagonists. Also included are combination therapies, wherein a therapeutic composition disclosed herein and an additional therapy agent are provided to a subject having or suspected of having cardiac disease and/or muscular dystrophy disorder where cardiac muscle regeneration is required.

BACKGROUND

Heart diseases encompass a family of disorders, including, but not limited to cardiomyopathies, myocardial infarction, and ischemic heart disease where cardiac muscle regeneration is required. Ischemic heart disease is a leading cause of morbidity and mortality in the industrialized world. Disorders within the heart disease spectrum are understood to arise from pathogenic changes in distinct cell types, such as cardiomyocytes, via alterations in a complex set of biochemical pathways. For example, certain pathological changes linked with heart disease can be accounted for by alterations in cardiomyocyte gene expression that lead to cardiomyocyte hypertrophy and impaired cardiomyocyte survival and contraction. Thus, an ongoing challenge in the development of heart disease treatments has been to identify effective therapies suitable for various types of heart diseases by, for example, promoting endogenous cardiac myocytes within the heart to divide and repair the damaged cardiac muscle.

The muscular dystrophies (MD) are a group of more than 30 genetic diseases characterized by progressive weakness and degeneration of the skeletal muscles that control movement. Some forms of MD are seen in infancy or childhood, while others may not appear until middle age or later. The disorders differ in terms of the distribution and extent of muscle weakness (some forms of MD also affect cardiac muscle), age of onset, rate of progression, and pattern of inheritance.

In particular, Duchenne muscular dystrophy (DMD) is one of the most prevalent inherited neuromuscular disorders. Caused by mutations in the dystrophin gene, DMD is characterized by progressive muscle weakness and wasting due to the absence of dystrophin protein resulting in degeneration of skeletal and cardiac muscle with subsequent fibrosis. The common cause of death for people with DMD is cardiomyopathy and heart failure. With no treatment currently available, there is a need for safe and effective therapies that prevent muscle degeneration in patients with DMD. The failure of human adult muscle cells to regenerate themselves constitutes a major clinical problem in DMD. This is compounded by the lack of adjunctive treatments, pharmacologic or cellular, that can be administered to successfully stimulate regeneration of cardiac muscle. Currently, there is no cure for DMD to fully restore dystrophin protein. With patients having a poor prognosis resulting in premature death, a significant unmet medical need exists for developing new treatment approaches.

SUMMARY

This section provides a general summary of the disclosure, and is not comprehensive of its full scope or all of its features.

The present disclosure generally relates to compositions and methods for the treatment of cardiac diseases and/or muscular dystrophy disorders. Some embodiments of the disclosure relate to the design of therapeutics and delivery systems of antagonists that specifically target a number of microRNAs of interest, including miR-9a-5p, miR-100-5p, Let-7a-5p, Let-7c-5p. In some embodiments, the compositions and methods disclosed herein allow for regeneration of cardiac muscles and for the treatment of heart diseases such as, for example, myocardial infarction or any cardiac injury where cardiac muscle regeneration is required. Without being bound by any particular theory, it is believed that regeneration of damaged cardiac myocytes can potentially lead to a reverse of ischemic injury of heart muscle after a heart attack.

In one aspect, disclosed herein are embodiments of compositions that include a plurality of microRNA (miR) antagonists, wherein the plurality of miR antagonists includes one or more miR-99a antagonists, one or more miR-100-5p antagonists, one or more miR-Let-7a-5p antagonists, and one or more miR-Let-7c-5p antagonists. Implementations of embodiments of the compositions according to this aspect and other aspects of the disclosure can include one or more of the following features.

In some embodiments, at least one of the one or more miR-99a antagonists includes an anti-miR-99a comprising a nucleotide sequence having at least 80%, 85%, 90%, 95%, 96%, 97, 98%, 99% or 100% sequence identity to a nucleotide sequence selected from the group consisting of SEQ ID NOs 47, 48, 50, 52, and 54. In some embodiments, at least one of the one or more miR-100-5p antagonists includes an anti-miR-100-5p comprising a nucleotide sequence having at least 80%, 85%, 90%, 95%, 96%, 97, 98%, 99% or 100% sequence identity to a nucleotide sequence selected from the group consisting of SEQ ID NOs 46, 49, 51, 53, and 55. In some embodiments, at least one of the one or more Let-7a-5p antagonists includes an anti-miR-Let-7a-5p comprising a nucleotide sequence having at least 80%, 85%, 90%, 95%, 96%, 97, 98%, 99% or 100% sequence identity to a nucleotide sequence selected from the group consisting of SEQ ID NOs: 37, 39, and 40-45. In some embodiments, at least one of the one or more Let-7c-5p antagonists includes an anti-miR-Let-7c-5p comprising a nucleotide sequence having at least 80%, 85%, 90%, 95%, 96%, 97, 98%, 99% or 100% sequence identity to a nucleotide sequence selected from the group consisting of SEQ ID NOs: 36, 38, and 40-45.

In some embodiments, at least one of the one or more miR-99a antagonists includes an anti-miR-99a comprising a nucleotide sequence having one or more mismatched nucleobases with respect to a sequence selected from the group consisting of SEQ ID NOs: 47, 48, 50, 52, and 54. In some embodiments, at least one of the one or more miR-100-5p antagonists includes an anti-miR-100-5p comprising a nucleotide sequence having one or more mismatched nucleobases with respect to a sequence selected from the group consisting of SEQ ID NOs: 46, 49, 51, 53, and 55. In some embodiments, at least one of the one or more Let-7a-5p antagonists includes an anti-miR-Let-7a-5p comprising a nucleotide sequence having one or more mismatched nucleobases with respect to a sequence selected from the group consisting of SEQ ID NOs: 37, 39, and 40-45. In some embodiments, at least one of the one or more Let-7c-5p antagonists includes an anti-miR-Let-7c-5p comprising a nucleotide sequence having one or more mismatched nucleobases with respect to a sequence selected from the group consisting of SEQ ID NOs: 36, 38, and 40-45.

In various embodiments of the compositions disclosed herein, at least one of the anti-miRs includes one or more chemical modifications selected from the group consisting of a modified internucleoside linkage, a modified nucleotide, and a modified sugar moiety, and combinations thereof. In some embodiments, the one or more chemical modifications includes a modified internucleoside linkage. In some embodiments, the modified internucleoside linkage is selected from the group consisting of a phosphorothioate, 2'-Omethoxyethyl (MOE), 2'-fluoro, alkylphosphonate, phosphorodithioate, alkylphosphonothioate, phosphoramidate, carbamate, carbonate, phosphate triester, acetamidate, carboxymethyl ester, and combinations thereof. In some embodiments, the modified internucleoside linkage includes a phosphorothioate internucleoside linkage. In some embodiments, at least one of the one or more chemical modifications includes a modified nucleotide. In some embodiments, the modified nucleotide includes a locked nucleic acid (LNA) chemistry modification, a peptide nucleic acid (PNA), an arabino-nucleic acid (FANA), an analogue, a derivative, or a combination thereof. In some embodiments, the modified nucleotide includes a locked nucleic acid (LNA). In some embodiments, the locked nucleic acid (LNA) is incorporated at one or both ends of the modified anti-miR. In some embodiments, at least one of the one or more chemical modifications includes a modified sugar moiety. In some embodiments, the modified sugar moiety is a 2'-O-methoxyethyl modified sugar moiety, a 2'-methoxy modified sugar moiety, a 2'-O-alkyl modified sugar moiety, a bicyclic sugar moiety, or a combination thereof. In some embodiments, the modified sugar moiety comprises a 2'-O-methyl sugar moiety. In some embodiments of the compositions disclosed herein, the composition is further formulated into a pharmaceutical formulation.

In one aspect, disclosed herein are embodiments of expression cassettes that include a nucleotide sequence encoding one or more miR-99a antagonists, one or more miR-100-5p antagonists, one or more miR-Let-7a-5p antagonists, and one or more miR-Let-7c-5p antagonists. In some embodiments, at least one of the one or more miR-99a antagonists includes an anti-miR-99a comprising a nucleotide sequence having at least 80%, 85%, 90%, 95%, 96%, 97, 98%, 99% or 100% sequence identity to a nucleotide sequence selected from the group consisting of SEQ ID NOs 47, 48, 50, 52, and 54. In some embodiments, at least one of the one or more miR-100-5p antagonists includes an anti-miR-100-5p comprising a nucleotide sequence having at least 80%, 85%, 90%, 95%, 96%, 97, 98%, 99% or 100% sequence identity to a nucleotide sequence selected from the group consisting of SEQ ID NOs 46, 49, 51, 53, and 55. In some embodiments, at least one of the one or more Let-7a-5p antagonists includes an anti-miR-Let-7a-5p comprising a nucleotide sequence having at least 80%, 85%, 90%, 95%, 96%, 97, 98%, 99% or 100% sequence identity to a nucleotide sequence selected from the group consisting SEQ ID NOs: 37, 39, and 40-45. In some embodiments, at least one of the one or more Let-7c-5p antagonists includes an anti-miR-Let-7c-5p comprising a nucleotide sequence having at least 80%, 85%, 90%, 95%, 96%, 97, 98%, 99% or 100% sequence identity to a nucleotide sequence selected from the group consisting of SEQ ID NOs: 36, 38, and 40-45.

In various embodiments of the expression cassettes disclosed herein, one or more of the following applies. In some embodiments, at least one of the one or more miR-99a antagonists includes an anti-miR-99a comprising a nucleotide sequence having one or more mismatched nucleobases with respect to a sequence selected from the group consisting of SEQ ID NOs: 47, 48, 50, 52, and 54. In some embodiments, at least one of the one or more miR-100-5p antagonists includes an anti-miR-100-5p comprising a nucleotide sequence having one or more mismatched nucleobases with respect to a sequence selected from the group consisting of SEQ ID NOs: 46, 49, 51, 53, and 55. In some embodiments, at least one of the one or more Let-7a-5p antagonists includes an anti-miR-Let-7a-5p comprising a nucleotide sequence having one or more mismatched nucleobases with respect to a sequence selected from the group consisting of SEQ ID NOs: 37, 39, and 40-45. In some embodiments, at least one of the one or more Let-7c-5p antagonists includes an anti-miR-Let-7c-5p comprising a nucleotide sequence having one or more mismatched nucleobases with respect to a sequence selected from the group consisting SEQ ID NOs: 36, 38, and 40-45.

In various embodiments of the expression cassettes disclosed herein, one or more of the following applies. In some embodiments, at least one of the anti-miRs includes one or more chemical modifications selected from the group consisting of a modified internucleoside linkage, a modified nucleotide, and a modified sugar moiety, and combinations thereof. In some embodiments, the one or more chemical modifications includes a modified internucleoside linkage. In some embodiments, the modified internucleoside linkage is selected from the group consisting of a phosphorothioate, 2'-Omethoxyethyl (MOE), 2'-fluoro, alkylphosphonate, phosphorodithioate, alkylphosphonothioate, phosphoramidate, carbamate, carbonate, phosphate triester, acetamidate, carboxymethyl ester, and combinations thereof. In some embodiments, the modified internucleoside linkage includes a phosphorothioate internucleoside linkage. In some embodiments, at least one of the one or more chemical modifications includes a modified nucleotide. In some embodiments, the modified nucleotide includes a locked nucleic acid (LNA) chemistry modification, a peptide nucleic acid (PNA), an arabino-nucleic acid (FANA), an analogue, a derivative, or a combination thereof. In some embodiments, the modified nucleotide includes a locked nucleic acid (LNA). In some embodiments, the locked nucleic acid (LNA) is incorporated at one or both ends of the modified anti-miR. In some embodiments, at least one of the one or more chemical modifications includes a modified sugar moiety. In some embodiments, the modified sugar moiety is a 2'-O-methoxyethyl modified sugar moiety, a 2'-methoxy modified sugar moiety, a 2'-O-alkyl modified sugar moiety, a bicyclic sugar moiety, or a combination thereof. In some embodiments, the modified sugar moiety comprises a 2'-O-methyl sugar moiety. In some embodiments, the composition according to this aspect is a pharmaceutical composition.

In one aspect, some embodiments of the present application relate to a cloning vector or expression vector that include an expression cassette as disclosed herein. In some embodiments, the cloning vector or expression vector disclosed herein includes an expression cassette including a nucleotide sequence which encodes one or more miR-99a antagonists, one or more miR-100-5p antagonists, one or more miR-Let-7a-5p antagonists, and one or more miR-Let-7c-5p antagonists. In some embodiments, the cloning vector or expression vector is a viral vector. In some embodiments, the viral vector is a lentiviral vector or an adeno-associated viral (AAV) vector. In some embodiments, the cloning vector or expression vector disclosed herein includes a nucleotide sequence having at least 80%, 85%, 90%, 95%, 96%, 97, 98%, 99% or 100% sequence identity to each of the nucleotide sequences set forth in SEQ ID NOs: 59-64; or a nucleotide sequence having at least 80%, 85%, 90%, 95%, 96%, 97, 98%, 99% or 100% sequence identity to each of the nucleotide sequences set forth in SEQ ID NOs: 86-89; or a nucleotide sequence having at least 80%, 85%, 90%, 95%, 96%, 97, 98%, 99% or 100% sequence identity to each of the nucleotide sequences set forth in the SEQ ID NOs indicated in a) and b). In some embodiments, the cloning vector or expression vector disclosed herein includes an expression cassette including a nucleotide sequence having least 80%, 85%, 90%, 95%, 96%, 97, 98%, 99% or 100% sequence identity to the nucleotide sequence of SEQ ID NO: 85.

In one aspect, disclosed herein are embodiments of a therapeutic composition that includes an effective amount of at least one therapeutic agent, and one or more of the followings: (a) a composition comprising a plurality of microRNA (miR) antagonists as disclosed herein; (b) an expression cassette as disclosed herein; and (c) a cloning or expression vector as disclosed herein. In some embodiments, the therapeutic composition is further formulated into a pharmaceutical formulation.

In some embodiments, the at least one therapeutic agent is selected from the group consisting of Idebenone, Eplerenone, VECTTOR, AVI-4658, Ataluren/PTC124/Translarna, BMN044/PRO044, CAT-1004, MicroDystrophin AAV Gene Therapy (SGT-001), Galectin-1 Therapy (SB-002), LTBB4 (SB-001), rAAV2.5-CMV-minidystrophin, Glutamine, NFKB inhibitors, Sarcoglycan, delta (35 kDa dystrophin-associated glycoprotein), Insulin like growth factor-1 (IGF-1), and combinations thereof. In some embodiments, the therapeutic composition according to this aspect is a pharmaceutical composition.

In one aspect, some embodiments of the disclosure relate to a method for treating a cardiac disease in a subject. The method includes administering or providing to the subject a therapeutic composition suitable for the treatment of cardiac diseases, wherein (a) the therapeutic composition is a composition comprising a plurality of microRNA (miR) antagonists as disclosed herein; (b) the therapeutic composition comprises an expression cassette as disclosed herein; or (c) the therapeutic composition comprises a cloning or expression vector as disclosed herein. In some embodiments, the method further includes identifying the subject as having or suspected of having a cardiac disease. In some embodiments, the cardiac disease is myocardial infarction, ischemic heart disease, dilated cardiomyopathy, heart failure (e.g., congestive heart failure), ischemic cardiomyopathy, hypertrophic cardiomyopathy, restrictive cardiomyopathy, alcoholic cardiomyopathy, viral cardiomyopathy, tachycardia-mediated cardiomyopathy, stress-induced cardiomyopathy, amyloid cardiomyopathy, arrhythmogenic right ventricular dysplasia, left ventricular noncompaction, endocardial fibroelastosis, aortic stenosis, aortic regurgitation, mitral stenosis, mitral regurgitation, mitral prolapse, pulmonary stenosis, pulmonary stenosis, pulmonary regurgitation, tricuspid stenosis, tricuspid regurgitation, congenital disorder, genetic disorder, or a combination thereof.

In another aspect, some embodiments of the disclosure relate to a method for promoting cardiac muscle regeneration in a subject. The method includes administering or providing to the subject a therapeutic composition, wherein (a) the therapeutic composition is a composition comprising a plurality of microRNA (miR) antagonists as disclosed herein; (b) the therapeutic composition comprises an expression cassette as disclosed herein; or (c) the therapeutic composition comprises a cloning or expression vector as disclosed herein. In some embodiments, the method further includes identifying or selecting the subject as having or suspected of having a cardiac disease. In some embodiments, the cardiac disease is myocardial infarction, ischemic heart disease, heart failure (e.g., congestive heart failure), ischemic cardiomyopathy, hypertrophic cardiomyopathy, restrictive cardiomyopathy, alcoholic cardiomyopathy, viral cardiomyopathy, tachycardia-mediated cardiomyopathy, stress-induced cardiomyopathy, amyloid cardiomyopathy, arrhythmogenic right ventricular dysplasia, left ventricular noncompaction, endocardial fibroelastosis, aortic stenosis, aortic regurgitation, mitral stenosis, mitral regurgitation, mitral prolapse, pulmonary stenosis, pulmonary stenosis, pulmonary regurgitation, tricuspid stenosis, tricuspid regurgitation, congenital disorder, genetic disorder, or a combination thereof. In some other particular embodiments, the cardiac disease is Ischemic heart disease where cardiac muscle regeneration is required.

In yet another aspect, some embodiments disclosed herein relate to a method of modulating proliferation of a cardiomyocyte and/or muscle cell. The method includes (1) introducing into a cardiomyocyte a therapeutic composition, wherein (a) the therapeutic composition is a composition comprising a plurality of microRNA (miR) antagonists as disclosed herein; (b) the therapeutic composition comprises an expression cassette as disclosed herein; or (c) the therapeutic composition comprises a cloning or expression vector as disclosed herein; and (2) allowing the cardiomyocyte obtained from (1) to divide, thereby modulating proliferation of the cardiomyocyte or muscle cell. In some embodiments, the introduction of the therapeutic composition into the cardiomyocyte includes transfecting the cardiomyocyte and/or muscle cell with at least one expression cassette or at least one viral vector comprising a nucleic acid sequence encoding the plurality of miR antagonists. In some embodiments, the method further includes measuring the proliferation of the cardiomyocyte and/or muscle cell. In some embodiments, the proliferation of the cardiomyocyte and/or muscle cell is increased compared to a control cardiomyocyte lacking the nucleic acid sequence encoding the plurality of miR antagonists. In some embodiments, the cardiomyocyte and/or muscle is in vivo. In some other embodiments, the cardiomyocyte and/or muscle is ex vivo. In some embodiments, the cardiomyocyte and/or muscle is of a human subject. In some embodiments, the human subject is suffering from a cardiac disease.

Implementations of embodiments of the methods disclosed herein can include one or more of the following features. In some embodiments, the plurality of miR antagonists are encoded by the same expression cassette or vector. In some embodiments, the plurality of miR antagonists are encoded by different expression cassettes or vectors. In some embodiments, the vector is a viral vector. In some embodiments, the viral vector is a lentiviral vector or an adeno-associated viral (AAV) vector. In some embodiments, the viral vector is an adeno-associated viral (AAV) vector.

In some embodiments, the methods further include administrating an effective amount of at least one additional therapeutic agent or at least one additional therapy to the subject for a combination therapy. In some embodiments, the at least one additional therapeutic agent or therapeutic therapy is selected from the group consisting of Idebenone, Eplerenone, VECTTOR, AVI-4658, Ataluren/PTC124/Translarna, BMN044/PRO044, CAT-1004, microDystrophin AAV gene therapy (SGT-001), Galectin-1 therapy (SB-002), LTBB4 (SB-001), rAAV2.5-CMV-minidystrophin, glutamine, NFKB inhibitors, sarcoglycan, delta (35 kDa dystrophin-associated glycoprotein), insulin like growth factor-1 (IGF-1) expression, genome editing through the CRISPR/Cas9 system, any gene delivery therapy aimed at reintroducing a functional recombinant version of the dystrophin gene, Exon skipping therapeutics, read-through strategies for nonsense mutations, cell-based therapies, utrophin upregulation, myostatin inhibition, anti-inflammatories/anti-oxidants, mechanical support devices, any standard therapy for muscular dystrophy, and combinations thereof. In some embodiments, the at least one additional therapeutic agent or therapy comprises a biologic drug. In some embodiments, the at least one additional therapeutic agent or therapy comprises a gene therapy or therapeutic gene modulation agent.

In some embodiments, each of the therapeutic composition and the at least one additional therapeutic agent or therapy is administered in a separate formulation. In some embodiments, the therapeutic composition and the at least one additional therapeutic agent or therapy are administered sequentially. In some embodiments, the therapeutic composition and the at least one additional therapeutic agent or therapy are administered concomitantly. In some embodiments, the therapeutic composition and the at least one additional therapeutic agent or therapy are administered in rotation. In some the therapeutic composition and the at least one additional therapeutic agent or therapy are administered together in a single formulation.

In one aspect, disclosed herein are embodiments of methods for treating a muscular dystrophy (MD) disorder. The method includes administering or providing to the subject a therapeutic composition, wherein (a) the therapeutic composition is a composition comprising a plurality of microRNA (miR) antagonists as disclosed herein; (b) the therapeutic composition comprises an expression cassette as disclosed herein; or (c) the therapeutic composition comprises a cloning or expression vector as disclosed herein, and wherein the administration of the therapeutic composition is performed in combination with an effective amount of at least one additional therapeutic agent or at least one additional therapy to provide a combination therapy. In some embodiments, the muscular dystrophy disorder is associated with Amyotrophic Lateral Sclerosis (ALS), Charcot-Marie-Tooth Disease (CMT), Congenital Muscular Dystrophy (CMD), Duchenne Muscular Dystrophy (DMD), Emery-Dreifuss Muscular Dystrophy (EDMD), Inherited and Endocrine Myopathies, Metabolic Diseases of Muscle, Mitochondrial Myopathies (MM), Myotonic Muscular Dystrophy (MMD), Spinal-Bulbar Muscular Atrophy (SBMA), or a combination thereof.

Also disclosed herein are embodiments of methods for increasing proliferation of a heart cell and/or increasing the expression and/or activity of proteins involved in muscle structure and/or function and/or regeneration, comprising contacting or providing the heart cell with a combination of (1) a therapeutic composition, wherein (a) the therapeutic composition is a composition comprising a plurality of microRNA (miR) antagonists as disclosed herein; (b) the therapeutic composition comprises an expression cassette as disclosed herein; or (c) the therapeutic composition comprises a cloning or expression vector as disclosed herein; and (2) at least one additional therapeutic agent or therapy. In some embodiments, the heart cell is selected from the group consisting of cardiac fibroblasts, cardiac myocytes, endothelial cells, and vascular smooth muscle cells (VSMCs). In some embodiments, the heart cell is selected from the group consisting of cardiomyocytes and skeletal muscle cells.

Also disclosed herein are embodiments of methods for inhibiting or reducing expression of a target microRNA (miR), comprising contacting or providing a heart cell with a combination of (1) a therapeutic composition, wherein (a) the therapeutic composition is a composition comprising a plurality of microRNA (miR) antagonists as disclosed herein; (b) the therapeutic composition comprises an expression cassette as disclosed herein; or (c) the therapeutic composition comprises a cloning or expression vector as disclosed herein; and (2) at least one additional therapeutic agent or therapy. In some embodiments, the heart cell is selected from the group consisting of cardiac fibroblasts, cardiac myocytes, endothelial cells, and vascular smooth muscle cells (VSMCs). In some embodiments, the heart cell is selected from the group consisting of cardiomyocytes and skeletal muscle cells.

Implementations of embodiments of the methods according to the foregoing aspects of the disclosure can include one or more of the following features. In some embodiments, the at least one additional therapeutic agent or therapeutic therapy is selected from the group consisting of Idebenone, Eplerenone, VECTTOR, AVI-4658, Ataluren/PTC124/Translarna, BMN044/PRO044, CAT-1004, microDystrophin AAV gene therapy (SGT-001), Galectin-1 therapy (SB-002), LTBB4 (SB-001), rAAV2.5-CMV-minidystrophin, glutamine, NFKB inhibitors, sarcoglycan, delta (35 kDa dystrophin-associated glycoprotein), insulin like growth factor-1 (IGF-1) expression modulation, genome editing through the CRISPR/Cas9 system, any gene delivery therapy aimed at reintroducing a functional recombinant version of the dystrophin gene, Exon skipping therapeutics, read-through strategies for nonsense mutations, cell-based therapies, utrophin upregulation, myostatin inhibition, anti-inflammatories/anti-oxidants, mechanical support devices, any standard therapy for muscular dystrophy, and combinations thereof. In some embodiments, the at least one additional therapeutic agent or therapy includes a biologic drug. In some embodiments, the at least one additional therapeutic agent or therapy comprises a gene therapy or therapeutic gene modulation agent. In some embodiments, each of the therapeutic composition and the at least one additional therapeutic agent or therapy is administered in a separate formulation. In some embodiments, the therapeutic composition and the at least one additional therapeutic agent or therapy are administered sequentially. In some embodiments, the therapeutic composition and the at least one additional therapeutic agent or therapy are administered concomitantly. In some embodiments, the therapeutic composition and the at least one additional therapeutic agent or therapy are administered in rotation. In some embodiments, the therapeutic composition and the at least one additional therapeutic agent or therapy are administered in a single formulation.

Disclosed herein further includes microRNA (miR) antagonists. In some embodiments, the miR antagonist include (a) a nucleotide sequence having at least 80%, 85%, 90%, 95%, 96%, 97, 98%, 99% or 100% sequence identity to a nucleotide sequence selected from the group consisting of SEQ ID NOs 47, 48, 50, 52, and 54; (b) a nucleotide sequence having at least 80%, 85%, 90%, 95%, 96%, 97, 98%, 99% or 100% sequence identity to a nucleotide selected from the group consisting of SEQ ID NOs 46, 49, 51, 53, and 55; or (c) a nucleotide sequence having at least 80%, 85%, 90%, 95%, 96%, 97, 98%, 99% or 100% sequence identity to a nucleotide selected from the group consisting of SEQ ID NOs: 37, 39, and 40-45; or (d) a nucleotide sequence having at least 80%, 85%, 90%, 95%, 96%, 97, 98%, 99% or 100% sequence identity to a nucleotide selected from the group consisting of SEQ ID NOs: 36, 38, and 40-45.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

BRIEF DESCRIPTION OF THE DRAWINGS

FIG. 14 shows expression of proteins in organ cultures of adult mouse heart.

Figure 1:
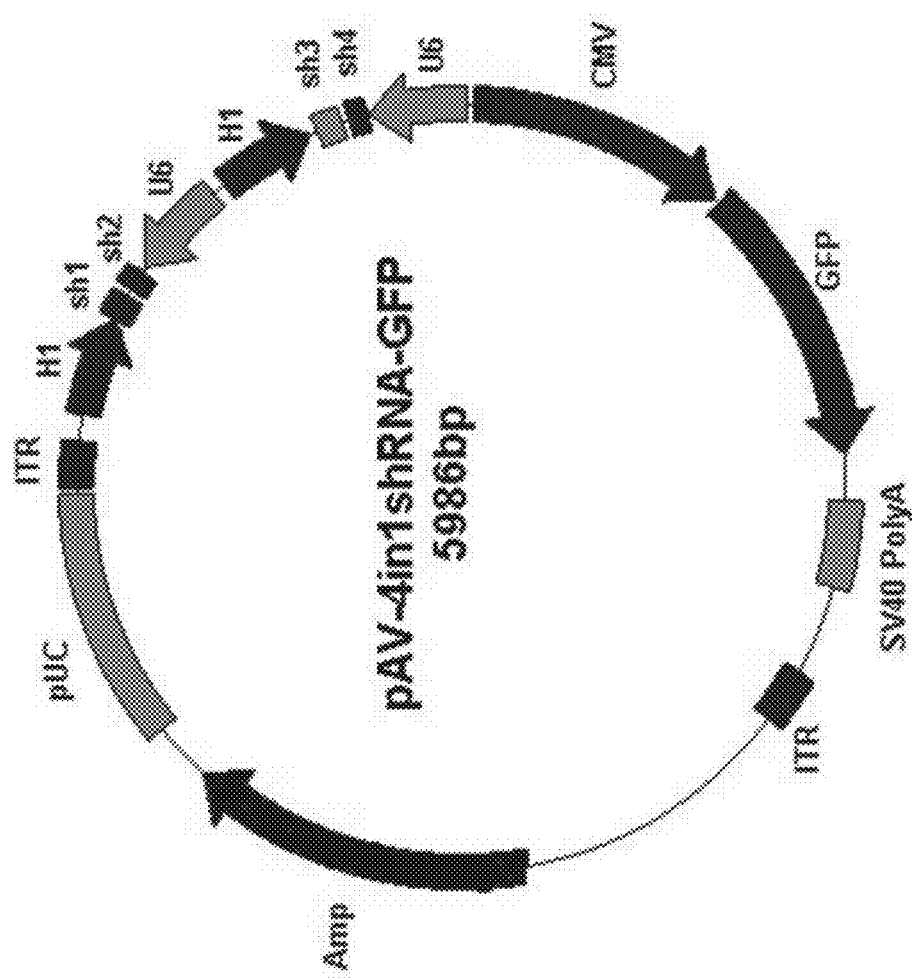
FIG. 1 is a schematic illustration of a non-limiting exemplary cloning vector design which includes nucleotide sequences encoding a modified hairpin Zip construct expressing Let-7a-5p and miR-99a-5p inhibitory sequences under control of the H1 promoter and U6 promoter, respectively. In this exemplary illustration, the vector also includes nucleotide sequences encoding a Let-7c-5p and miR-100-5p inhibitory sequences under the regulation of the H1 and U6 promoter, respectively.

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope; the disclosure will be described with additional specificity and detail through use of the accompanying drawings.

DETAILED DESCRIPTION

The present disclosure generally relates to novel microRNA antagonists, therapeutic compositions that include one or more of such microRNA antagonists, and methods of treating and/or ameliorating cardiac diseases and/or muscular dystrophy disorders with such microRNA antagonists. Also included are combination therapies wherein a therapeutic composition disclosed herein and an additional therapy agent are provided to a subject having or suspected of having cardiac disease and/or muscular dystrophy disorder. In particular, some embodiments disclosed herein relate to the use of various combinations of synthetic oligonucleotide miR-99A-5P, miR-100-5P, Let-7a-5p, and Let-7c-5p antagonists and/or viral delivered miR-99A-5P, miR-100-5P, Let-7a-5p, and Let-7c-5p antagonists, chemotherapeutic agents, and biological agents for the treatment of cardiac diseases and/or muscular dystrophy disorders. For example, some embodiments disclosed herein describe two adenoviral AAV2/9 delivery systems (referred to herein as JBT-miR1 and JBT-miR2), and the corresponding expression vectors with a number of variants for miR-99a-5p, miR-100-5p, Let-7a-5p, Let-7c-5p antagonists that are capable of inhibiting the respective target microRNAs. Further provided herein are a number of synthetic oligonucleotide antagonists designed for specifically targeting miR-99a-5p, miR-100-5p, Let-7a-5p, and Let-7c, individually or in combination.

In the following detailed description, reference is made to the accompanying Figures, which form a part hereof. The illustrative embodiments described in the detailed description, Figures, and claims are not meant to be limiting. Other embodiments may be used, and other changes may be made, without departing from the spirit or scope of the subject matter presented here. It will be readily understood that the embodiments of the present disclosure, as generally described herein, and illustrated in the Figures, can be arranged, substituted, combined, and designed in a wide variety of different configurations, all of which are explicitly contemplated and make part of this disclosure.

Some Definitions

Unless otherwise defined, all terms of art, notations and other scientific terms or terminology used herein are intended to have the meanings commonly understood by those of skill in the art to which this disclosure pertains when read in light of this disclosure. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. (See, e.g., Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989).

The singular form "a", "an", and "the" include plural references unless the context clearly dictates otherwise. For example, the term "a molecule" includes one or more molecules, including mixtures thereof. As used in this disclosure and the appended claims, the term "and/or" can be singular or inclusive. For example, "A and/or B" is used herein to include all of the following alternatives: "A", "B", and "A and B".

The term "about", as used herein, has its ordinary meaning of approximately. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

"Administering" means providing a pharmaceutical agent or composition to a subject, and includes, but is not limited to, administering by a medical professional and self-administering.

"Parenteral administration," means administration through injection or infusion. Parenteral administration includes, but is not limited to, subcutaneous administration, intravenous administration, intramuscular administration, intra-arterial administration, and intracranial administration. "Subcutaneous administration" means administration just below the skin. "Intravenous administration" means administration into a vein. "Intraarterial administration" means administration into an artery.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, y-carboxyglutamate, and 0-phosphoserine. Amino acid analogs refers to compounds that have the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Antisense compound" means a compound having a nucleobase sequence that will allow hybridization to a target nucleic acid. In certain embodiments, an antisense compound is an oligonucleotide having a nucleobase sequence complementary to a target nucleic acid.

The terms "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing. The terms "protein", "peptide", and "polypeptide" are used interchangeably to denote an amino acid polymer or a set of two or more interacting or bound amino acid polymers. These terms, as used herein, encompass amino acid polymers in which one or more amino acid residue is an artificial chemical mimetic of a corresponding naturally occurring amino acid, as well as to naturally occurring amino acid polymers and non-naturally occurring amino acid polymer.

The phrase "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical nucleotide sequences. Because of the degeneracy of the genetic code, a large number of functionally identical nucleic acids can encode any given protein. For instance, the codons GCA, GCC, GCG and GCU all encode the amino acid alanine. Thus, at every position where an alanine is specified by a codon, the codon can be altered to any of the corresponding codons described above without altering the encoded polypeptide. Such nucleic acid variations are "silent variations," which are one species of conservatively modified variations. Any one of the nucleic acid sequences described herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, all silent variations of a nucleic acid which encodes a polypeptide are implicit in each of the described sequences with respect to its expression product, but not with respect to actual probe sequences. In addition or alternatively, a variant can comprises deletions, substitutions, additions of one or more nucleotides at the 5' end, 3' end, and/or one or more internal sites in comparison to the reference polynucleotide. Similarities and/or differences in sequences between variants and the reference polynucleotide can be detected using conventional techniques known in the art, for example polymerase chain reaction (PCR) and hybridization techniques. Variant polynucleotides also include synthetically derived polynucleotides, such as those generated, for example, by using site-directed mutagenesis. Generally, a variants of a particular polynucleotide disclosed herein, including, but not limited to, a miRNA, will have at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs known by skilled artisan.

The terms "identical" or "percent identity", in the context of two or more nucleic acids or proteins, refer to two or more sequences or subsequences that are the same or have a specified percentage of nucleotides or amino acids that are the same (e.g., about 60% sequence identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the complement of a test sequence. This definition also includes sequences that have deletions and/or additions, as well as those that have substitutions. Sequence identity typically exists over a region that is at least about 50 amino acids or nucleotides in length, or over a region that is 50-100 amino acids or nucleotides in length, or over the entire length of a given sequence.

As used herein, the term "construct" is intended to mean any recombinant nucleic acid molecule such as an expression cassette, plasmid, cosmid, virus, autonomously replicating polynucleotide molecule, phage, or linear or circular, single-stranded or double-stranded, DNA or RNA polynucleotide molecule, derived from any source, capable of genomic integration or autonomous replication, comprising a nucleic acid molecule where one or more nucleic acid sequences has been linked in a functionally operative manner, e.g. operably linked.

The term "transfection" or "transfecting" is defined as a process of introducing a nucleic acid molecule to a cell using non-viral or viral-based methods. The nucleic acid molecule can be a sequence encoding complete proteins or functional portions thereof. Typically, a nucleic acid vector comprises the elements necessary for protein expression (e.g., a promoter, transcription start site, etc.). Non-viral methods of transfection include any appropriate transfection method that does not use viral DNA or viral particles as a delivery system to introduce the nucleic acid molecule into the cell. Exemplary non-viral transfection methods include, but are not limited to, calcium phosphate transfection, liposomal transfection, nucleofection, sonoporation, transfection through heat shock, magnetifection, and electroporation. For viral-based methods, any one of useful viral vectors known in the art can be used in the methods described herein. Examples of viral vectors include, but are not limited to retroviral, adenoviral, lentiviral and adeno-associated viral vectors. In some aspects, the nucleic acid molecules are introduced into a cell using a retroviral vector following standard procedures known in the art.

The term "heterologous" when used with reference to portions of a nucleic acid or protein indicates that the nucleic acid or protein comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "gene" is used broadly to refer to any segment of nucleic acid molecule that encodes a protein or that can be transcribed into a functional RNA. Genes may include sequences that are transcribed but are not part of a final, mature, and/or functional RNA transcript, and genes that encode proteins may further comprise sequences that are transcribed but not translated, for example, 5' untranslated regions (5'-UTR), 3' untranslated regions (3'-UTR), introns, etc. Further, genes may optionally further comprise regulatory sequences required for their expression, and such sequences may be, for example, sequences that are not transcribed or translated. Genes can be obtained from a variety of sources, including cloning from a source of interest or synthesizing from known or predicted sequence information, and may include sequences designed to have desired parameters.

The term "internucleoside linkage" means a covalent linkage between adjacent nucleosides.

The term "nucleobase" means a heterocyclic moiety capable of non-covalently pairing with another nucleobase.

"Nucleoside" means a nucleobase linked to a sugar. "Linked nucleosides" means nucleosides joined by a covalent linkage. "Nucleotide" means a nucleoside having a phosphate group covalently linked to the sugar portion of a nucleoside.

"miR antagonist" means an agent designed to interfere with or inhibit the activity of a miRNA. In certain embodiments, a miR antagonist comprises an antisense compound targeted to a miRNA. In certain embodiments, a miR antagonist comprises a modified oligonucleotide having a nucleobase sequence that is complementary to the nucleobase sequence of a miRNA, or a precursor thereof. In certain embodiments, a miR antagonist comprises a small molecule, or the like that interferes with or inhibits the activity of an miRNA.

"miR-9a-5p antagonist" means an agent designed to interfere with or inhibit the activity of miR-9a-5p. "miR-100-5p antagonist" means an agent designed to interfere with or inhibit the activity of miR-100-5p. "Let-7a-5p antagonist" means an agent designed to interfere with or inhibit the activity of Let-7a-5p. "Let-7c-5p antagonist" means an agent designed to interfere with or inhibit the activity of Let-7c-5p.

"Modified oligonucleotide" means an oligonucleotide having one or more chemical modifications relative to a naturally occurring terminus, sugar, nucleobase, and/or internucleoside linkage.

"Modified internucleoside linkage" means any change from a naturally occurring internucleoside linkage.

"Phosphorothioate internucleoside linkage" means a linkage between nucleosides where one of the non-bridging atoms is a sulfur atom.

"Modified sugar" means substitution and/or any change from a natural sugar.

"Modified nucleobase" means any substitution and/or change from a natural nucleobase.

"5-methylcytosine" means a cytosine modified with a methyl group attached to the 5' position.

"2'-O-methyl sugar" or "2'-OMe sugar" means a sugar having an O-methyl modification at the 2' position.

"2'-O-methoxyethyl sugar" or "2'-MOE sugar" means a sugar having an O-methoxyethyl modification at the 2' position.

"2'-O-fluoro sugar" or "2'-F sugar" means a sugar having a fluoro modification of the 2' position.

"Bicyclic sugar moiety" means a sugar modified by the bridging of two non-geminal ring atoms.

"2'-O-methoxyethyl nucleoside" means a 2'-modified nucleoside having a 2'-O-methoxyethyl sugar modification.

"2'-fluoro nucleoside" means a 2'-modified nucleoside having a 2'-fluoro sugar modification.

"2'-O-methyl" nucleoside means a 2'-modified nucleoside having a 2'-O-methyl sugar modification.

"Bicyclic nucleoside" means a 2'-modified nucleoside having a bicyclic sugar moiety.

As used herein, the terms "miR," "mir," and "miRNA" are used interchangeably and to refer to microRNA, a class of small RNA molecules that are capable of hybridizing to and regulating the expression of a coding RNA. In certain embodiments, a miRNA is the product of cleavage of a pre-miRNA by the enzyme Dicer. These terms as provided herein refer to a nucleic acid that forms a double stranded RNA which has the ability to reduce or inhibit expression of a gene or target gene when expressed in the same cell as the gene or target gene. The complementary portions of the nucleic acid that hybridize to form the double stranded molecule typically have substantial or complete identity. In one embodiment, a "microRNA" refers to a nucleic acid that has substantial or complete identity to a target gene and forms a double stranded miRNA. In some embodiments, the miRNA of the disclosure inhibits gene expression by interacting with a complementary cellular mRNA thereby interfering with the expression of the complementary mRNA. In some embodiments, the double stranded miRNA of the present disclosure is at least about 15-50 nucleotides in length (e.g., each complementary sequence of the double stranded miRNA is 15-50 nucleotides in length, and the double stranded miRNA is about 15-50 base pairs in length). In some embodiments, the length is 20-30 base nucleotides, preferably about 20-25 or about 24-29 nucleotides in length, e.g., 20, 21, 22, 23, 24, 25, 26, 27, 28, 29, or 30 nucleotides in length. In some embodiments of the disclosure, the microRNA is selected from, or substantially similar to a microRNA selected from, the group consisting of miR-9a-5p, miR-100-5p, Let-7a-5p, and Let-7c-5p.

As used herein, the term "anti-miRNA" is used interchangeably with the term "anti-miR", which refers to an oligonucleotide capable of interfering with or inhibiting one or more activities of one or more target microRNAs. In some embodiments, the anti-miRNA is a chemically synthesized oligonucleotide. In some embodiments, the anti-miRNA is a small molecule. In some embodiments, the anti-miRNA is a miR antisense molecule. "Seed region" means nucleotides 2 to 6 or 2 to 7 from the 5'-end of a mature miRNA sequence.

The term "miRNA precursor" means a transcript that originates from a genomic DNA and that comprises a non-coding, structured RNA comprising one or more miRNA sequences. For example, in certain embodiments a miRNA precursor is a pre-miRNA. In certain embodiments, a miRNA precursor is a pri-miRNA.

"Pre-miRNA" or "pre-miR" means a non-coding RNA having a hairpin structure, which contains a miRNA. In certain embodiments, a pre-miRNA is the product of cleavage of a pri-miR by the double-stranded RNA-specific ribonuclease known as Drosha. Without wishing to be bound by any particular theory, it is believed that in the cytoplasm, the pre-miRNA hairpin is cleaved by the RNase III enzyme Dicer. This endoribonuclease interacts with 5' and 3' ends of the hairpin and cuts away the loop joining the 3' and 5' arms, yielding an imperfect miRNA:miRNA duplex of about 22 nucleotides in length. Although either strand of the duplex may potentially act as a functional miRNA, it is believed that only one strand is usually incorporated into the RNA-induced silencing complex (RISC) where the miRNA and its mRNA target interact. The remaining strand—sense strand—is degraded. The RNA-induced silencing complex, or RISC, is a multiprotein complex, specifically a ribonucleoprotein, which incorporates one strand of a single-stranded RNA (ssRNA) fragment, such as microRNA (miRNA), or double-stranded small interfering RNA (siRNA).

"Modulation" means to a perturbation of function or activity. In certain embodiments, modulation means an increase in gene expression. In certain embodiments, modulation means a decrease in gene expression. The term "microRNA modulator" as used herein refers to an agent capable of modulating the level of expression of a microRNA (e.g., let-7 a, let-7 c, miR-100, miR-99). In some embodiments, the microRNA modulator is encoded by a nucleic acid. In other embodiments, the microRNA modulator is a small molecule (e.g., a chemical compound or synthetic microRNA molecule). In some embodiments, the microRNA modulator decreases the level of expression of a microRNA compared to the level of expression in the absence of the microRNA modulator. Where the microRNA modulator decreases the level of expression of a microRNA relative to the absence of the modulator, the microRNA modulator is an antagonist of the micro RNA. In some embodiments, the microRNA modulator increases the level expression of a micro RNA compared to the level of expression in the absence of the microRNA modulator. Where the microRNA modulator increases the level of expression of a micro RNA relative to the absence of the modulator, the microRNA modulator is an agonist of the microRNA.

As used herein, the term "myocardial cell" includes any cell that is obtained from, or present in, myocardium such as a human myocardium and/or any cell that is associated, physically and/or functionally, with myocardium. In some embodiments disclosed herein, a myocardial cell is a cardiomyocyte.

The term "nucleotide" covers naturally occurring nucleotides as well as non-naturally occurring nucleotides. Thus, "nucleotides" includes not only the known purine and pyrimidine heterocycles-containing molecules, but also heterocyclic analogues and tautomers thereof. Non-limiting examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in U.S. Pat. No. 5,432,272. The term "nucleotide" is intended to cover every and all of these examples as well as analogues and tautomers thereof.

The term "nucleic acid" and "polynucleotide" are used interchangeably herein and refer to deoxyribonucleotides or ribonucleotides and polymers thereof in either single- or double-stranded form, and complements thereof. The term "polynucleotide" include linear sequences of nucleotides. The term "nucleotide" typically refers to a single unit of a poly-nucleotide, e.g., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, and 2'-O-methyl ribonucleotides. As such, the term "nucleic acid" and "polynucleotide" encompass nucleic acids comprising phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil.

The term "operably linked", as used herein, denotes a functional linkage between two or more sequences. For example, an operably linkage between a polynucleotide of interest and a regulatory sequence (for example, a promoter) is functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. In some embodiments disclosed herein, the term "operably linked" denotes a configuration in which a regulatory sequence is placed at an appropriate position relative to a sequence that encodes a polypeptide or functional RNA such that the control sequence directs or regulates the expression or cellular localization of the mRNA encoding the polypeptide, the polypeptide, and/or the functional RNA. Thus, a promoter is in operable linkage with a nucleic acid sequence if it can mediate transcription of the nucleic acid sequence. Operably linked elements may be contiguous or non-contiguous.

The terms "promoter", "promoter region", or "promoter sequence", as used interchangeably herein, refer to a nucleic acid sequence capable of binding RNA polymerase to initiate transcription of a gene in a 5' to 3' ("downstream") direction. The specific sequence of the promoter typically determines the strength of the promoter. For example, a strong promoter leads to a high rate of transcription initiation. A gene is "under the control of" or "regulated by" a promoter when the binding of RNA polymerase to the promoter is the proximate cause of said gene's transcription. The promoter or promoter region typically provides a recognition site for RNA polymerase and other factors necessary for proper initiation of transcription. A promoter may be isolated from the 5' untranslated region (5' UTR) of a genomic copy of a gene. Alternatively, a promoter may be synthetically produced or designed by altering known DNA elements. Also considered are chimeric promoters that combine sequences of one promoter with sequences of another promoter. A promoter can be used as a regulatory element for modulating expression of an operably linked polynucleotide molecule such as, for example, a coding sequence of a polypeptide or a functional RNA sequence. Promoters may contain, in addition to sequences recognized by RNA polymerase and, preferably, other transcription factors, regulatory sequence elements such as cis-elements or enhancer domains that affect the transcription of operably linked genes. In some embodiments, a promoter can be "constitutive." In some embodiments, a promoter may be regulated in a "tissue-specific" or "tissue-preferred" manner, such that it is only active in transcribing the operable linked coding region in a specific tissue type or types. In some embodiments, for therapeutic purposes, the promoter can be a tissue-specific promoter which supports transcription in cardiac and skeletal muscle cell. Further information in this regard can be found in, for example, PCT Patent Publication WO2004041177A2, which is hereby incorporated by reference in its entirety. In some embodiments, a promoter may comprise "naturally-occurring" or "synthetically" assembled nucleic acid sequences.

Expression of a transfected gene can occur transiently or stably in a host cell. During "transient expression" the transfected nucleic acid is not integrated into the host cell genome, and is not transferred to the daughter cell during cell division. Since its expression is restricted to the transfected cell, expression of the gene can be lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into to the host genome. During transposon-mediated insertion, the gene is positioned in a predictable manner between two transposon linker sequences that allow insertion into the host genome as well as in subsequent excision.

The terms "inhibitor," "repressor" or "antagonist" or "downregulator", as used interchangeably herein, refer to a substance, agent, or molecule that results in a detectably lower expression or activity level of a target gene as compared to a control. The inhibited expression or activity can be 10%, 20%, 30%, 40%, 50%, 60%, 70%, 80%, 90% or less than that in a control. In some embodiments, the inhibition is 1.5-fold, 2-fold, 3-fold, 4-fold, 5-fold, 10-fold, or more in comparison to a control. In some embodiments, an antagonist is an anti-miR.

As used herein, "treatment" refers to a clinical intervention made in response to a disease, disorder or physiological condition manifested by a patient or to which a patient may be susceptible. The aim of treatment includes, but is not limited to, the alleviation or prevention of symptoms, slowing or stopping the progression or worsening of a disease, disorder, or condition and/or the remission of the disease, disorder or condition. "Treatments" refer to one or both of therapeutic treatment and prophylactic or preventative measures. Subjects in need of treatment include those already affected by a disease or disorder or undesired physiological condition as well as those in which the disease or disorder or undesired physiological condition is to be prevented. In some embodiments of the disclosure, the terms "treatment," "therapy," and "amelioration" refer to any reduction in the severity of symptoms, e.g., of a neurodegenerative disorder or neuronal injury. As used herein, the terms "treat" and "prevent" are not intended to be absolute terms. Treatment can refer to any delay in onset, amelioration of symptoms, and improvement in patient survival, increase in survival time or rate, etc., or a combination thereof. The effect of treatment can be compared to an individual or pool of individuals not receiving the treatment, or to the same patient prior to treatment or at a different time during treatment. In some embodiments, the severity of disease or disorder in an individual can be reduced by at least 10%, as compared, e.g., to the individual before administration or to a control individual not undergoing treatment. In some embodiments, the severity of disease or disorder in an individual is reduced by at least 25%, 50%, 75%, 80%, or 90%, or in some embodiments, no longer detectable using standard diagnostic techniques.

As used herein, the term "effective amount" or "therapeutically effective amount" refers to an amount sufficient to effect beneficial or desirable biological and/or clinical results. In some embodiments, the term refers to that amount of the therapeutic agent sufficient to ameliorate a given disorder or symptoms. For example, for the given parameter, a therapeutically effective amount can show an increase or decrease of at least 5%, 10%, 15%, 20%, 25%, 40%, 50%, 60%, 75%, 80%, 90%, or at least 100% compared to a control. Therapeutic efficacy can also be expressed as "-fold" increase or decrease. For example, a therapeutically effective amount can have at least a 1.2-fold, 1.5-fold, 2-fold, 5-fold, or more effect over a control.

The terms "subject," "patient," "individual in need of treatment" and like terms are used interchangeably and refer to, except where indicated, an mammal subject that is the object of treatment, observation, or experiment. As used herein, "mammal" refers to a subject belonging to the class Mammalia and includes, but not limited to, humans, domestic and farm animals, zoo animals, sports and pet animals. Non-limiting examples of mammals include humans, and non-human primates, mice, rats, sheep, dogs, horses, cats, cows, goats, pigs, and other mammalian species. In some embodiments, the mammal is a human. However, in some embodiments, the mammal is not a human. The term does not necessarily indicate that the subject has been diagnosed with a particular disease or disorder, but typically refers to a subject under medical supervision. "Subject suspected of having" means a subject exhibiting one or more clinical indicators of a disease or condition. In certain embodiments, the disease or condition is a muscular dystrophy (MD) disorder.

"Target nucleic acid," "target RNA," "target RNA transcript" and "nucleic acid target" all mean a nucleic acid capable of being targeted by antagonists. "Targeting" means the process of design and selection of nucleobase sequence that will hybridize to a target nucleic acid and induce a desired effect. "Targeted to" means having a nucleobase sequence that will allow hybridization to a target nucleic acid to induce a desired effect. In certain embodiments, a desired effect is reduction of a target nucleic acid.

As used herein, the term "variant" refers to a polynucleotide (or polypeptide) having a sequence substantially similar to a reference polynucleotide (or polypeptide). In the case of a polynucleotide, a variant can have deletions, substitutions, additions of one or more nucleotides at the 5' end, 3' end, and/or one or more internal sites in comparison to the reference polynucleotide. Similarities and/or differences in sequences between a variant and the reference polynucleotide can be detected using conventional techniques known in the art, for example polymerase chain reaction (PCR) and hybridization techniques. Variant polynucleotides also include synthetically derived polynucleotides, such as those generated, for example, by using site-directed mutagenesis. Generally, a variant of a polynucleotide, including, but not limited to, a DNA, can have at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs known by skilled artisans. In the case of a polypeptide, a variant can have deletions, substitutions, additions of one or more amino acids in comparison to the reference polypeptide. Similarities and/or differences in sequences between a variant and the reference polypeptide can be detected using conventional techniques known in the art, for example Western blot. Generally, a variant of a polypeptide, can have at least about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polypeptide as determined by sequence alignment programs known by one of ordinary skill in the art.

As used herein, "comprising" is synonymous with "including," "containing," or "characterized by," and is inclusive or open-ended and does not exclude additional, unrecited elements or method steps. As used herein, "consisting of" excludes any elements, steps, or ingredients not specified in the claimed composition or method. As used herein, "consisting essentially of" does not exclude materials or steps that do not materially affect the basic and novel characteristics of the claimed composition or method. Any recitation herein of the term "comprising", particularly in a description of components of a composition or in a description of steps of a method, is understood to encompass those compositions and methods consisting essentially of and consisting of the recited components or steps.

In some embodiments of the methods or processes described herein, the steps can be carried out in any order, except when a temporal or operational sequence is explicitly recited. Furthermore, in some embodiments, the specified steps can be carried out concurrently unless explicit claim language recites that they be carried out separately. For example, in some embodiments a claimed step of doing X and a claimed step of doing Y can be conducted simultaneously within a single operation, and the resulting process will fall within the literal scope of the claimed process.

The section headings, e.g., (a), (b), (i) etc., are presented merely for ease of reading the specification and claims, as they are used herein for organizational purposes only and are not to be construed as limiting the subject matter described. The use of headings in the specification or claims does not require the steps or elements be performed in alphabetical or numerical order or the order in which they are presented. All documents, or portions of documents, cited in the application including, without limitation, patents, patent applications, articles, books, manuals, and treatises are hereby expressly incorporated by reference in their entireties.

As will be understood by one having ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

I. Cardiac Diseases and Micro-Ribonucleic Acid (miRNA)

Cardiac disease or heart disease is a disease for which several classes or types exist (e.g., Ischemic Cardiomyopathy (ICM), Dilated Cardiomyopathy (DCM), Aortic Stenosis (AS)) and, many require unique treatment strategies. Thus, heart disease is not a single disease, but rather a family of disorders arising from distinct cell types (e.g., myocardial cells) by distinct pathogenetic mechanisms. The challenge of heart disease treatment has been to target specific therapies to particular heart disease types, to maximize effectiveness and to minimize toxicity. Improvements in heart disease categorization (classification) have thus been central to advances in heart disease treatment. As used herein, cardiac disease encompasses the following non-limiting examples: heart failure (e.g., congestive heart failure), ischemic cardiomyopathy, hypertrophic cardiomyopathy, restrictive cardiomyopathy, alcoholic cardiomyopathy, viral cardiomyopathy, tachycardia-mediated cardiomyopathy, stress-induced cardiomyopathy, amyloid cardiomyopathy, arrhythmogenic right ventricular dysplasia, left ventricular noncompaction, endocardial fibroelastosis, aortic stenosis, aortic regurgitation, mitral stenosis, mitral regurgitation, mitral prolapse, pulmonary stenosis, pulmonary regurgitation, tricuspid stenosis, tricuspid regurgitation, congenital disorder, genetic disorder, or a combination thereof.

Heart cell regeneration: Throughout the 20th century the human heart was believed to be a terminally differentiated post mitotic organ, unable to be repaired after an injury. This was challenged in 2001 when mitosis in cardiomyocytes was evident after a myocardial infarction. Studies by others confirmed that adult mammalian hearts can elicit a primitive regeneration response upon injury with mature differentiated mononuclear mammalian cardiomyocytes re-entering the cell cycle upon application of chemical compounds that target specific signaling pathways.

miRNAs (also referred to as miRs) are small non-coding RNA molecules conserved in plants, animals, and some viruses, which function in RNA silencing and post-transcriptional regulation of gene expression. Identified in 1993, they are a vital and evolutionarily component of genetic regulation. They function via base-pairing and silencing complementary sequences within mRNA molecules thereby modulating target protein expression and downstream signaling pathways. There are 1000 known miRs in the human genome that can target 60% of human genes. In animals, miRNAs are processed from larger primary transcripts (pri-miRNA or pri-miR) through an approximate 60-bp hairpin precursor (pre-miRNA or pre-miR) into the mature forms (miRNA) by two RNAse III enzymes Drosha and Dicer. The mature miRNA is loaded into the 50 ribonucleoprotein complex (RISC), where it typically guides the downregulation of target mRNA through base pair inter-actions. Pri-miRNAs are transcribed by RNA polymerase II and predicted to be regulated by transcription factors in an inducible manner. While some miRNAs show ubiquitous expression, others exhibit only limited developmental stage-, tissue- or cell type-specific patterns of expression.

As described in greater detail below, measurements previously made in myocardial tissue have suggested the miRNAs play a regulatory role in myocardial growth, fibrosis, and remodeling. In particular, ribonucleic acid interference (RNAi) technology is an area of intense research for the development of new therapies for heart disease, with studies demonstrating the utility of adeno-associated virus (AAV) for delivering oligonucleotides in vivo. Two separate AAV2/9 virus' expressing antagonists of microRNAs (miRs) let-7a/let-c and miR-99/100 can induce proliferation of cardiomyocytes in the ischemic mouse heart for up to 3 months following a single injection. Transcriptomic and translational analysis on mice heart cells and tissues treated with viral delivered miR antagonists showed differences in the expression of genes and proteins involved in cardiac development, proliferation and muscle structure and function, implying that a similar regenerative effect, through targeting of these miRs, may occur in human cardiac myocytes and models of DMD.

RNAi technology can take many forms, but it is typically implemented within a cell in the form of a base-pair short hairpin (sh) RNA (shRNA), which is processed into an approximately 20 base pair small interfering RNA through the endogenous miR pathway. Viral delivery of complementary sequences to miRs is a common approach. AAV vectors are optimal in cardiovascular muscle gene delivery since they a) contain no viral protein-coding sequences to stimulate an immune response, b) do not require active cell division for expression to occur and c) have a significant advantage over adenovirus vectors because of their stable, long-term expression of recombinant genes in myocytes in vivo. Viral delivery of genes are in development for the treatment of DMD and include AAV1-gamma-sarcoglycan vector as a therapy for LGMD, recombinant (r) AAV2.5 vector for delivery of mini dystrophin, and rAAV, rhesus serotype 74.

As described herein, the mechanism by which the miRNA antagonist functions to inhibit the activity of the target miRNA is not limited in any way. For example, a nucleic acid-based antagonist, may form a duplex with the target miRNA sequences and prevent proper processing of the mature miRNA product from its precursor, or may prevent the mature miRNA from binding to its target gene, or may lead to degradation of pri-, pre-, or mature miRNA, or may act through some other mechanism.

let-7a/c and miR-100/99: By studying the mechanisms of heart regeneration in zebrafish and neonatal mice, scientists have found that heart regeneration is a primarily cardiomyocyte-mediated process that occurs by dedifferentiation of mature cardiomyocytes followed by proliferation and further re-differentiation. Epigenetic remodeling and cell cycle control are two key steps controlling this regenerative process. Aguirre et al (Cell Stem Cell. 2014; 15(5):589-604) reported a very relevant study, which investigated the underlying mechanism of heart regeneration and identified a series of miRs strongly involved in zebrafish heart regeneration. Focus on those miRs that present significant expression changes and that were conserved across vertebrates, both in sequence and 3' UTR binding sites, led to the identification of two miR families (miR-99/100, let-7a/c) clustered in two well-defined genomic locations. This finding was supported by a common role for the miR-99a/Let-7c-5p cluster in regulating vertebrate cardiomyogenesis. MIRANDA-based miR-UTR binding predictions showed a strong interaction for miR-99/100 with zebrafish FNTβ (beta subunit of farnesyl-transferase) and SMARCA5 (SWI/SNF-related matrix associated actin-dependent regulator of chromatin subfamily a, member 5), linking the miR families to cell cycle and epigenetic control in cardiomyocytes. Interestingly, miR-99/100 and let-7a/c levels are low during early mammalian heart development and promote quick cardiac mass growth, but increase exponentially during late development, with a corresponding decrease in FNTβ and SMARCA5 protein levels to block further cardiomyocyte proliferation. Post-mortem analysis of injured human heart tissue, suggests that these miRs constitute a conserved roadblock to cardiac regeneration in adults. RNA-seq transcriptomic analysis on neonatal mouse cardiomyocytes transduced two viral delivered antagonists to let-7a/c and miR-99/100 revealed differences in genes involved in epigenetic remodeling, demethylation, cardiac development, proliferation, and unexpectedly, metabolic pathways and muscle structural and function. Indeed, miR-let 7a/c and miR-99/100 inhibition targets 1072 and 47 genes, respectively.

A number of selective genes involved in muscle structure and function include actin/myosin, NFKB inhibitor interacting Ras-like 2, sarcoglycan, delta (35 kDa dystrophin-associated glycoprotein) and IGF-1 that are current therapeutic targets for muscular dystrophies (see, Table 1 below). Semi-quantitative mass spectrometry on organ cultures of mouse hearts treated with the inhibitors identified metabolic and mitochondrial processes as key actors, while also highlighting changes in cytoskeleton and proteins involved in muscle contraction as shown in FIG. 14.

TABLE 1

Non-limiting examples of selected target genes for Let-7a-5p in neonatal mouse cardiac myocytes

| Target gene | Representative transcript | Gene name |
|---|---|---|
| IGF2BP3 | NM_006547 | insulin-like growth factor 2 mRNA binding protein 3 |
| COL24A1 | NM_152890 | collagen, type XXIV, alpha 1 |
| TMEM135 | NM_001168724 | transmembrane protein 135 |
| CHD9 | NM_025134 | chromodomain helicase DNA binding protein 9 |
| IGF1R | NM_000875 | insulin-like growth factor 1 receptor |
| IGF2BP2 | NM_001007225 | insulin-like growth factor 2 mRNA binding protein 2 |
| ACTA1 | NM_001100 | actin, alpha 1, skeletal muscle |
| FKBP10 | NM_021939 | FK506 binding protein 10, 65 kDa |
| ACVR1B | NM_004302 | activin A receptor, type IB |
| MYO5B | NM_001080467 | myosin VB |
| INSR | NM_000208 | insulin receptor |
| ITGB8 | NM_002214 | integrin, beta 8 |
| FRS2 | NM_001042555 | fibroblast growth factor receptor substrate 2 |
| ACVR1C | NM_001111031 | activin A receptor, type IC |
| COL3A1 | NM_000090 | collagen, type III, alpha 1 |
| NGF | NM_002506 | nerve growth factor (beta polypeptide) |
| COL4A6 | NM_001847 | collagen, type IV, alpha 6 |

TABLE 1-continued

Non-limiting examples of selected target genes for Let-7a-5p in neonatal mouse cardiac myocytes

| Target gene | Representative transcript | Gene name |
|---|---|---|
| CTHRC1 | NM_138455 | collagen triple helix repeat containing 1 |
| IRS2 | NM_003749 | insulin receptor substrate 2 |
| NOS1 | NM_000620 | nitric oxide synthase 1 (neuronal) |
| MYRIP | NM_015460 | myosin VIIA and Rab interacting protein |
| COL11A1 | NM_001190709 | collagen, type XI, alpha 1 |
| NKIRAS2 | NM_001001349 | NFKB inhibitor interacting Ras-like 2 |
| SMAD2 | NM_001003652 | SMAD family member 2 |
| TTL | NM_153712 | tubulin tyrosine ligase |
| SGCD | NM_000337 | sarcoglycan, delta (35 kDa dystrophin-associated glycoprotein) |
| COL14A1 | NM_021110 | collagen, type XIV, alpha 1 |
| COL1A1 | NM_000088 | collagen, type I, alpha 1 |
| COL15A1 | NM_001855 | collagen, type XV, alpha 1 |
| FNDC3B | NM_001135095 | fibronectin type III domain containing 3B |
| COL4A5 | NM_000495 | collagen, type IV, alpha 5 |
| MFAP3L | NM_001009554 | microfibrillar-associated protein 3-like |
| ACVR2B | NM_001106 | activin A receptor, type IIB |
| RPS6KA3 | NM_004586 | ribosomal protein S6 kinase, 90 kDa, polypeptide 3 |

II. Muscular Dystrophy

The muscular dystrophies (MD) are a group of more than 30 genetic diseases characterized by progressive weakness and degeneration of the skeletal muscles that control movement. Some forms of MD are seen in infancy or childhood, while others may not appear until middle age or later. The disorders differ in terms of the distribution and extent of muscle weakness (some forms of MD also affect cardiac muscle), age of onset, rate of progression, and pattern of inheritance.

Duchenne muscular dystrophy (DMD) is a progressive, an X-linked recessive inherited muscle-wasting disease, leading to severe disability and premature death. DMD is caused by mutations on one of the 21.2 band on the short arm of the X chromosomes, affecting half of the male infants of mothers who carry the genetic defect. This gene is responsible for producing cytoplasmic dystrophin protein, an essential part of a protein complex that connects the cytoskeleton of a muscle fiber to the surrounding extracellular matrix through the cell membrane. Without dystrophin, muscles degenerate. The primary symptoms of the disease is muscle weakness, respiratory problems and early diastolic dysfunction caused by focal fibrosis which proceeds to dilated cardiomyopathy (DCM), complicated by heart failure and arrhythmia in most patients. Current treatments for DMD are solely symptomatic. Table 3 below provides a listing of non-limiting examples of current standard approaches for the treatment of Duchenne Muscular Dystrophy.

TABLE 3

Standard therapy for muscular Duchenne dystrophy (DMD)

| Intervention | Timing/Use | Examples/Limitations |
|---|---|---|
| Corticosteroids | Age <4 years | Prednisone, Prednisolone, Deflazacort/Behavioral changes, failure to gain height, weight gain, osteoporosis, impaired glucose tolerance, blood pressure changes, immune/adrenal suppression, dyspepsia/peptic ulceration, cataract, and skin changes, cushingoid features, red reflex of eyes, bone fractures, infections. |
| Nutrition | Age <4 years | Calcium and vitamin D intake, controlled sodium intake/Weight control. |
| Respiratory care | With symptoms | Ventilators/ Management of chest infections with antibiotics. |
| Cardiac care | Age 5-10 years | ACE-inhibitors, beta-blockers, diuretics with onset of HF. Anticoagulation therapy considered with severe cardiac dysfunction to prevent systemic thromboembolic events. If ventricular arrhythmias occur, antiarrhythmic treatment is introduced with possible negative inotropic effects. Echocardiogram and ECG every five years. |
| Orthopedics | Variable | Splinting, Knee-Ankle-Foot Orthosis, fusion. |
| Psychosocial | Variable | Social (information, advocacy and advice) and psychological support |
| Rehabilitation | At diagnosis | Physiotherapists and occupational therapists. Moderate active exercise. |

There have been over 200 clinical studies for DMD and selective interventional studies with results. Table 4 below provides a listing of non-limiting examples of Selective Clinical Investigative therapies for interventional DMD trials that have been reported previously. Current DMD therapeutic approaches in clinical development include, 1) gene delivery therapy aimed at reintroducing a functional recombinant version of the dystrophin gene, 2) exon skipping, 3) read-through strategies for nonsense mutations, 4) cell-based therapies, 5) utrophin upregulation, myostatin inhibition, Insulin like growth factor-1 (IGF-1) expression, 6) approved commercial products and 7) anti-Inflammatories/anti-oxidants.

TABLE 4

Selective clinical investigative agents interventional DMD trials for which results have been previously reported

| Therapy | Phase | Clinical Trials Identifier: | Main findings/status |
| --- | --- | --- | --- |
| Idebenone | IIa | NCT00654784 | Respiratory treatment effect on peak expiratory |
|  | III | NCT01027884 | flow (p = 0.039 for PEF) [62], Reduced the loss of respiratory function. |
| Eplerenone | II | NCT01521546 | Lower decline in left ventricular circumferential strain than placebo |
| VECTTOR |  | NCT01874275 | Indicted in the U.S. for chronic, intractable pain and post-surgical trauma pain. Device considered for off-label use. |
| AVI-4658 | II | NCT01396239 | Increase in six minute walk test, decreased |
| AVI-4658 | I/II | NCT00844597 | incidence in loss of ambulation [66-67]. New dystrophin protein expression (p = 0.0203). Restoration of α-sarcoglycan and nitric oxide synthase. |
| Ataluren/PTC124/ | II | NCT00264888 | Approval in European Union approval for |
| Translarna | III | NCT00592553 | nonsense mutation DMD. |
| BMN044/PRO044 | I/II | NCT01037309 | Increase in expression of dystrophin protein. |
| CAT-1004 | I/II | NCT02439216 | Phase I showed safety, and no adverse events |
| rAAV2.5-CMV-minidystrophin | I | NCT00428935 | Failure to establish long-term transgene expression in muscle fibers. |
| Glutamine | III | NCT00296621 | No disease modifying effect. |
|  |  | NCT00018109 | No disease modifying effect. |

Major problems of finding effective treatments is the need to target different muscles in the body, the requirement of a long-term effect, the problem of fibrosis and the necessity for various versions of a drug to address different mutations. Although long-term expression could be achieved with gene therapy, restoration of dystrophin protein expression is complicated by the large size of dystrophin cDNA that cannot be carried by a viral vector. Smaller versions of dystrophin (mini- and micro-dystrophins) have been developed to address this problem. For limb-girdle muscular dystrophy type 2D (LGMD) clinical trials have shown promising results. Genome editing through the CRISPR/Cas9 system has demonstrated encouraging findings in preclinical murine models but is not yet possible in humans.

Despite a number of investigative therapies, full recovery of dystrophin protein is not achievable. Finding alternative therapeutic strategies that increase the expression of compensatory genes and proteins and regenerate both endogenous cardiac muscle in DMD patients is an urgent necessity.

Intriguingly, heart regenerating vertebrates that do not develop pathologic remodeling after a heart attack (including neonatal mice), heal by cardiomyocyte dedifferentiation and proliferation, illustrating two important facts: 1) cardiomyocytes represent a larger and more efficient pool of regenerative precursors than stem cells and 2) regeneration is an innate property of mammalian hearts and can lead to functional recovery, albeit inefficiently, in adults.

III. Compositions of the Disclosure
MicroRNA Antagonists

Disclosed herein includes embodiments of compositions that include a plurality of microRNA (miR) antagonists. As used herein, "miR antagonist" refers to an agent designed to interfere with or inhibit the activity of a miRNA. In certain embodiments, a miR antagonist comprises an antisense compound targeted to a miRNA. In certain embodiments, a miR antagonist comprises a modified oligonucleotide having a nucleotide sequence that is complementary to the nucleotide sequence of a miRNA, or a precursor thereof. In other embodiments, a miR antagonist comprises a small molecule, or the like that interferes with or inhibits the activity of a miRNA. In some embodiments, a miR antagonist is a miR-99a antagonist. In some embodiments, a miR antagonist is a miR-100-5p antagonist. In some embodiments, a miR antagonist is a miR-Let-7a-5p antagonist. In some embodiments, a miR antagonist is a miR-Let-7c-5p antagonist. The miR antagonists disclosed herein are useful, for example, in providing compositions and methods to prevent, inhibit, or reduce target gene expression in, for example, myocardium (e.g., myocardial tissue, myocardial cells). Thus, some of the embodiments disclosed herein relate to the use of the miR antagonists of the disclosure in methods for evaluation and therapy of cardiac diseases, including heart failure.

Implementations of embodiments of the compositions according to this aspect and other aspects of the disclosure can include one or more of the following features. In some embodiments, the plurality of miR antagonists includes 4, 5, 6, 7, 8, 9, 10, 15, 20, 30, 40, 50 miR antagonists or a number of antagonists that is within a range defined by any two of the aforementioned values. In some embodiments, the plurality of miR antagonists includes one or more selected from miR-99a antagonists, miR-100-5p antagonists, miR-Let-7a-5p antagonists, miR-Let-7c-5p antagonists, and combinations thereof. In some embodiments, the plurality of miR antagonists includes one or more miR-99a antagonists, one or more miR-100-5p antagonists, one or more miR-Let-7a-5p antagonists, and one or more miR-Let-7c-5p antagonists.

In some embodiments, the numbers of each miR antagonist group are the same in the plurality of miR antagonists. In some embodiments, the numbers of each miR antagonist group are not the same in the plurality of miR antagonists.

Accordingly, in some embodiments, the plurality of miR antagonists includes at least one miR antagonist comprising a nucleotide sequence having, or having about, 85%, 90%, 91%, 92%, 93%, 94%, 95%, 96%, 97%, 98%, 99%, 100%, or a range between any two of these values, sequence identity to one or more of the miR antagonists disclosed herein. For example, in some embodiments, the miR antagonist comprises, or consists of, a nucleotide sequence having at least about 85%, at least about 90%, at least about 95%, at least about 96%, at least about 97%, at least about 98%, at least about 99%, or more, sequence identity to one or more of the miR antagonists disclosed herein. In some embodiments, the miR antagonist comprises, or consists of, a nucleotide sequence having at least about 85%, at least about 90%, at least about 95%, at least about 96%, at least about 97%, at least about 98%, at least about 99%, or more, sequence identity to one or more of the miR antagonists disclosed herein. In some embodiments, the miR antagonist comprises, or consists of, a nucleotide sequence having about 85%, about 90%, about 95%, about 96%, about 97%, about 98%, about 99%, about 100%, or a range between any two of these values, sequence identity to one or more of the miR antagonists disclosed herein.

In some embodiments, at least one of the one or more miR-99a antagonists includes an anti-miR-99a comprising a nucleotide sequence having at least about, or having about, 80%, 85%, 90%, 95%, 96%, 97, 98%, 99% or 100%, or a range between any two of these values, sequence identity to a sequence selected from the group consisting of SEQ ID NOs 47, 48, 50, 52, and 54. In some embodiments, at least one of the one or more miR-100-5p antagonists includes an anti-miR-100-5p comprising a nucleotide sequence having at least about, or having about, 80%, 85%, 90%, 95%, 96%, 97, 98%, 99% or 100%, or a range between any two of these values, sequence identity to a sequence selected from the group consisting of SEQ ID NOs 46, 49, 51, 53, and 55. In some embodiments, at least one of the one or more Let-7a-5p antagonists includes an anti-miR-Let-7a-5p comprising a nucleotide sequence having at least about, or having about, 80%, 85%, 90%, 95%, 96%, 97, 98%, 99% or 100%, or a range between any two of these values, sequence identity to a sequence selected from the group consisting SEQ ID NOs: 37, 39, and 40-45. In some embodiments, at least one of the one or more Let-7c-5p antagonists includes an anti-miR-Let-7c-5p comprising a nucleotide sequence having at least about, or having about, 80%, 85%, 90%, 95%, 96%, 97, 98%, 99% or 100%, or a range between any two of these values, sequence identity to a sequence selected from the group consisting of SEQ ID NOs: 36, 38, and 40-45.

In some embodiments of the compositions disclosed herein, one or more of the followings applies. In some embodiments, at least one of the one or more miR-99a antagonists includes an anti-miR-99a comprising a nucleotide sequence having one or more mismatched nucleobases with respect to a sequence selected from the group consisting of SEQ ID NOs: 47, 48, 50, 52, and 54. In some embodiments, at least one of the one or more miR-100-5p antagonists includes an anti-miR-100-5p comprising a nucleotide sequence having one or more mismatched nucleobases with respect to a sequence selected from the group consisting of SEQ ID NOs: 46, 49, 51, 53, and 55. In some embodiments, at least one of the one or more Let-7a-5p antagonists includes an anti-miR-Let-7a-5p comprising a nucleotide sequence having one or more mismatched nucleobases with respect to a sequence selected from the group consisting of SEQ ID NOs: 37, 39, and 40-45. In some embodiments, at least one of the one or more Let-7c-5p antagonists includes an anti-miR-Let-7c-5p comprising a nucleotide sequence having one or more mismatched nucleobases with respect to a sequence selected from the group consisting of SEQ ID NOs: 36, 38, and 40-45.

In some embodiments, the plurality of miR antagonists includes at least one miR antagonist comprising a nucleotide sequence having, or having about, 1, 2, 3, 4, 5, 6, 7, 8, 9, 10, or a range between any two of these values, mismatched nucleobases with respect to the nucleotide sequence of one or more of the miR antagonists disclosed herein. For example, in some embodiments, the miR antagonist comprises, or consists of, a nucleotide sequence having at least about 1, at least about 2, at least about 3, at least about 4, at least about 5, or more, mismatched nucleobases with respect to the nucleotide sequence of one or more of the miR antagonists disclosed herein. In some embodiments, the miR antagonist comprises, or consists of, a nucleotide sequence having at least about 6, at least about 7, at least about 8, at least about 9, at least about 10, or more, mismatched nucleobases with respect to the nucleotide sequence of one or more of the miR antagonists disclosed herein.

Accordingly, in some embodiments, at least one of the one or more miR-99a antagonists includes an anti-miR-99a comprising a nucleotide sequence having, or having about, 1, 2, 3, 4, 5, 6, 7, 8, 9, 10, or a range between any two of these values, mismatched nucleobases with respect to a nucleotide sequence selected from the group consisting of SEQ ID NOs: 47, 48, 50, 52, and 54. In some embodiments, at least one of the one or more miR-100-5p antagonists includes an anti-miR-100-5p comprising a nucleotide sequence having, or having about, 1, 2, 3, 4, 5, 6, 7, 8, 9, 10, or a range between any two of these values, mismatched nucleobases with respect to a nucleotide sequence selected from the group consisting of SEQ ID NOs: 46, 49, 51, 53, and 55. In some embodiments, at least one of the one or more Let-7a-5p antagonists includes an anti-miR-Let-7a-5p comprising a nucleotide sequence having, or having about, 1, 2, 3, 4, 5, 6, 7, 8, 9, 10, or a range between any two of these values, mismatched nucleobases with respect to a nucleotide sequence selected from the group consisting of SEQ ID NOs: 37, 39, and 40-45. In some embodiments, at least one of the one or more Let-7c-5p antagonists includes an anti-miR-Let-7c-5p comprising a nucleotide sequence having, or having about, 1, 2, 3, 4, 5, 6, 7, 8, 9, 10, or a range between any two of these values, mismatched nucleobases with respect to a nucleotide sequence selected from the group consisting of SEQ ID NOs: 36, 38, and 40-45.

In various embodiments of the compositions disclosed herein, at least one of the anti-miRs includes one or more chemical modifications described herein. Suitable chemical modifications include, but are not limited to, modifications to a nucleobase, a sugar, and/or an internucleoside linkage. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases. Accordingly, in some embodiments of the compositions disclosed herein, at least one of the anti-miRs includes one or more chemical modifications selected from the group consisting of a modified internucleoside linkage, a modified nucleotide, and a modified sugar moiety, and combinations thereof.

In some embodiments, the one or more chemical modifications includes a modified internucleoside linkage. Generally, a modified internucleoside linkage can be any internucleoside linkage known in the art. Non-limiting examples of suitable modified internucleoside linkage include a phosphorothioate, 2'-Omethoxyethyl (MOE), 2'-fluoro, alkylphosphonate, phosphorodithioate, alkylphosphonothioate, phosphoramidate, carbamate, carbonate, phosphate triester, acetamidate, carboxymethyl ester, and combinations thereof. In some embodiments, the modified internucleoside linkage comprises a phosphorus atom. In some embodiments, the modified internucleoside linkage does not comprise a phosphorus atom. In certain such embodiments, an internucleoside linkage is formed by a short chain alkyl internucleoside linkage. In certain such embodiments, an internucleoside linkage is formed by a cycloalkyl internucleoside linkages. In certain such embodiments, an internucleoside linkage is formed by a mixed heteroatom and alkyl internucleoside linkage. In certain such embodiments, an internucleoside linkage is formed by a mixed heteroatom and cycloalkyl internucleoside linkages. In certain such embodiments, an internucleoside linkage is formed by one or more short chain heteroatomic internucleoside linkages. In certain such embodiments, an internucleoside linkage is formed by one or more heterocyclic internucleoside linkages. In certain such embodiments, an internucleoside linkage has an amide backbone. In certain such embodiments, an internucleoside linkage has mixed N, O, S and $CH_2$ component parts. In some embodiments, at least one of the anti-miRs includes a modified internucleoside linkage which is a phosphorothioate internucleoside linkage.

In some embodiments, at least one of the one or more chemical modifications includes a modified nucleotide. A modified nucleotide can generally be any modified nucleotide and can be for example, a locked nucleic acid (LNA) chemistry modification, a peptide nucleic acid (PNA), an arabino-nucleic acid (FANA), an analogue, a derivative, or a combination thereof. In some embodiments, the modified nucleotide comprises 5-methylcytosines. In some embodiments, a modified nucleotide is selected from 5-hydroxymethyl cytosine, 7-deazaguanine and 7-deazaadenine. In certain embodiments, the modified nucleotide is selected from 7-deaza-adenine, 7-deazaguanosine, 2-aminopyridine and 2-pyridone. In certain embodiments, the modified nucleotide is selected from 5-substituted pyrimidines, 6-azapyrimidines and N-2, N-6 and O-6 substituted purines, including 2 aminopropyladenine, 5-propynyluracil and 5-propynylcytosine. In certain embodiments, a modified nucleotide comprises a polycyclic heterocycle. In certain embodiments, a modified nucleotide comprises a tricyclic heterocycle. In certain embodiments, a modified nucleotide comprises a phenoxazine derivative. In certain embodiments, the phenoxazine can be further modified to form a nucleobase known in the art as a G-clamp.

In some embodiments, the modified nucleotide includes a locked nucleic acid (LNA). In some embodiments, the one or more chemical modifications includes at least one locked nucleic acid (LNA) chemistry modifications to enhance the potency, specificity and duration of action and broaden the routes of administration of oligonucleotides. This can be achieved by substituting some of the nucleobases in a base nucleotide sequence by LNA nucleobases. The LNA modified nucleotide sequences may have a size similar to the parent nucleobase or may be larger or preferably smaller. In some embodiments, the LNA-modified nucleotide sequences contain less than about 70%, less than about 65%, more preferably less than about 60%, less than about 55%, most preferably less than about 50%, less than about 45% LNA nucleobases and that their sizes are between about 5 and 25 nucleotides, more preferably between about 12 and 20 nucleotides. In some embodiments, the locked nucleic acid (LNA) is incorporated at one or both ends of the modified anti-miR.

In some embodiments, the one or more chemical modifications include at least one modified sugar moiety. In some embodiments, In certain embodiments, a sugar modified nucleoside is a 2'-modified nucleoside, wherein the sugar ring is modified at the 2' carbon from natural ribose or 2'-deoxy-ribose. In some embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In some embodiments, the bicyclic sugar moiety comprises a bridge group between the 2' and the 4'-carbon atoms. In certain such embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N($R_1$)—, —C($R_1$)($R_2$)—, —C($R_1$)=C($R_1$)—, —C($R_1$)=N—, —C(=N$R_1$)—, —Si($R_1$)($R_2$)—, —S(=O)$_2$—, —S(=O)—, —C(=O)— and —C(=S)—; where each $R_1$ and $R_2$ is, independently, H, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, substituted oxy (—O—), amino, substituted amino, azido, carboxyl, substituted carboxyl, acyl, substituted acyl, CN, thiol, substituted thiol, sulfonyl (S(=O)$_2$—H), substituted sulfonyl, sulfoxyl (S(=O)—H) or substituted sulfoxyl; and each substituent group is, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, amino, substituted amino, acyl, substituted acyl, $C_1$-$C_{12}$ aminoalkyl, $C_1$-$C_{12}$ aminoalkoxy, substituted $C_1$-$C_{12}$ aminoalkyl, substituted $C_1$-$C_{12}$ aminoalkoxy or a protecting group.

In some embodiments, the bicyclic sugar moiety is bridged between the 2' and 4' carbon atoms with a biradical group selected from —O—($CH_2$)$_p$—, —O—$CH_2$—, —O—$CH_2CH_2$—, —O—CH(alkyl)-, —NH—($CH_2$)$_p$—, —N(alkyl)-($CH_2$)$_p$—, —O—CH(alkyl)-, —(CH(alkyl))—($CH_2$)$_p$—, —NH—O—($CH_2$)$_p$—, —N(alkyl)-O—($CH_2$)$_p$—, or —O—N(alkyl)-($CH_2$)$_p$—, wherein p is 1, 2, 3, 4 or 5 and each alkyl group can be further substituted. In certain embodiments, p is 1, 2 or 3.

In some embodiments, a 2'-modified nucleoside comprises a 2'-substituent group selected from halo, allyl, amino, azido, SH, CN, OCN, $CF_3$, $OCF_3$, O—, S—, or N($R_m$)-alkyl; O—, S—, or N($R_m$)-alkenyl; O—, S— or N($R_m$)-alkynyl; O-alkylenyl-O-alkyl, alkynyl, alkaryl, aralkyl, O-alkaryl, O-aralkyl, O($CH_2$)$_2$$SCH_3$, O—($CH_2$)$_2$—O—N($R_m$)($R_n$) or O—$CH_2$—C(=O)—N($R_m$)($R_n$), where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In some embodiments, a 2'-modified nucleoside comprises a 2'-substituent group selected from F, $NH_2$, $N_3$, $OCF_3$, O—$CH_3$, $O(CH_2)_3NH_2$, $CH_2$—CH=$CH_2$, O—$CH_2$—CH=$CH_2$, $OCH_2CH_2OCH_3$, $O(CH_2)_2SCH_3$, O—$(CH_2)_2$—O—$N(R_m)(R_n)$, —$O(CH_2)_2O(CH_2)_2N(CH_3)_2$, and N-substituted acetamide (O—$CH_2$—C(=O)—$N(R_m)(R_n)$) where each $R_m$ and $R_n$ is, independently, H, an amino protecting group or substituted or unsubstituted $C_1$-$C_{10}$ alkyl.

In some embodiments, a 2'-modified nucleoside comprises a 2% substituent group selected from F, OCF3, O—CH3, OCH2CH2OCH3, 2'-O(CH2)2SCH3, O—(CH2)2-O—N(CH3)2, O(CH2)2O(CH2)2N—(CH3)2, and O—CH2-C(=O)—N(H)CH3.

In some embodiments, a 2'-modified nucleoside comprises a 2'-substituent group selected from F, O—$CH_3$, and $OCH_2CH_2OCH_3$.

In some embodiments, a sugar-modified nucleoside is a 4'-thio modified nucleoside. In certain embodiments, a sugar-modified nucleoside is a 4'-thio-2'-modified nucleoside. A 4'-thio modified nucleoside has a β-D-ribonucleoside where the 4'-O replaced with 4'-S. A 4'-thio-2'-modified nucleoside is a 4'-thio modified nucleoside having the 2'-OH replaced with a 2'-substituent group. Suitable 2'-substituent groups include 2'-$OCH_3$, 2'-O—$(CH_2)_2$—$OCH_3$, and 2'-F.

Accordingly, in some embodiments of the disclosure, the modified sugar moiety is a 2'-O-methoxyethyl modified sugar moiety, a 2'-methoxy modified sugar moiety, a 2'-O-alkyl modified sugar moiety, a bicyclic sugar moiety, or a combination thereof. In some embodiments, the modified sugar moiety comprises a 2'-O-methyl sugar moiety.

Expression Cassettes

In some embodiments, one or more of the miR antagonists described herein are encoded by and expressed from expression cassettes. Thus, in one aspect, some embodiments of the present disclosure related to expression cassettes that include a nucleotide sequence encoding one or more miR antagonists described herein. As used herein, "expression" refers to the process of converting genetic information of a polynucleotide into RNA through transcription, which is typically catalyzed by an enzyme, RNA polymerase, and, where the RNA encodes a polypeptide, into protein, through translation of mRNA on ribosomes to produce the encoded protein. The term "expression cassette" as used herein, refers to a nucleic acid construct that encodes a gene, a protein, or a functional RNA operably linked to expression control elements, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc.

Cloning Vectors and Expression Vectors

In a related aspect, one or more of the miR antagonists described herein can be encoded by and/or expressed from a cloning vector or an expression vector. Accordingly, some embodiments of the present application are directed to a cloning vector or expression vector that includes an expression cassette as disclosed herein. As used herein, the term "vector" refers to a nucleic acid construct, typically a plasmid or a virus, used to transmit genetic material to a host cell. Vectors can be, for example, viruses, plasmids, cosmids, or phage. A vector as used herein can be composed of either DNA or RNA. In some embodiments, a vector is composed of DNA. In some embodiments, a vector is composed of RNA. The term "vector" includes cloning vectors and expression vectors, as well as viral vectors and integrating vectors. An "expression vector" is a vector that is capable of directing the expression of a gene, or protein encoded by one or more genes carried by the vector when it is present in the appropriate environment. Vectors are preferably capable of autonomous replication. Typically, an expression vector comprises a transcription promoter, a gene, and a transcription terminator. Gene expression is usually placed under the control of a promoter, and a gene is said to be "operably linked to" the promoter.

Accordingly, in some embodiments, the cloning vector or expression vector disclosed herein includes an expression cassette including a nucleotide sequence which encodes one or more miR antagonists described herein. In some embodiments, the cloning vector or expression vector disclosed herein includes an expression cassette including a nucleotide sequence which encodes one or more miR-99a antagonists, one or more miR-100-5p antagonists, one or more miR-Let-7a-5p antagonists, and one or more miR-Let-7c-5p antagonists.

In some embodiments, the cloning vector or expression vector is a viral vector. As used herein, a "viral vector" is a viral-derived nucleic acid molecule that is capable of transporting another nucleic acid into a cell. A viral vector is capable of directing expression of a gene, a protein or proteins encoded by one or more genes carried by the vector when it is present in the appropriate environment. Examples for viral vectors include, but are not limited to retroviral vectors, adenoviral vectors, lentiviral vectors, and adeno-associated viral vectors.

Accordingly, in some embodiments, the viral vector is a lentiviral vector or an adeno-associated viral (AAV) vector or any serotype. As used herein, the term "serotype" or "serovar" is a distinct variation within a species of bacteria or virus or among immune cells of different individuals. These microorganisms, viruses, or cells are classified together based on their cell surface antigens, allowing the epidemiologic classification of organisms to the sub-species level. Generally, the AAV vector can be any existing AAV vectors and can be, for example, an AAV vector selected from the group consisting of serotype 1, 2, 3, 4, 5, 6, 7, 8, 9, and 10 or chimeric AAV derived thereof, which will be even better suitable for high efficiency transduction in the tissue of interest. Upon transfection, AAV elicits only a minor immune reaction (if any) in the host. Therefore, AAV vector is highly suited for gene therapy approaches. It has been reported that, for transduction in mice, AAV serotype 6 and AAV serotype 9 are particularly suitable. For gene transfer into a human, AAV serotypes 1, 6, 8 and 9 are generally preferred. It has been also assumed that the capacity of AAV for packaging a therapeutic gene is limited to approximately 4.9 kb, while longer sequences lead to truncation of AAV particles. In some embodiments, the AAV vector is an AAV2/9 vector, e.g., AAV2 inverted terminal repeat (ITR) sequences cross-packaged into AAV capsid.

In some embodiments, disclosed herein are cloning or expression vectors having, or having about, 85%, 90%, 91%, 92%, 93%, 94%, 95%, 96%, 97%, 98%, 99%, 100%, or a range between any two of these values, sequence identity to one or more of the vectors disclosed herein. For example, in some embodiments, the cloning or expression vector comprises, or consists of, a nucleotide sequence having at least about 85%, at least about 90%, at least about 95%, at least about 96%, at least about 97%, at least about 98%, at least about 99%, or more, sequence identity to the full sequence of JBT-miR1 (SEQ ID NO: 85). In some embodiments, the vector comprises, or consists of, a nucleotide sequence having at least about 85%, at least about 90%, at least about 95%, at least about 96%, at least about 97%, at least about 98%, at least about 99%, or more, sequence identity to the nucleotide sequence of JBT-miR2. In some embodiments, the vector comprises, or consists of, a nucleotide sequence having about 85%, about 90%, about 95%, about 96%, about 97%, about 98%, about 99%, about 100%, or a range between any two of these values, sequence identity to the full sequence of JBT-miR1 (SEQ ID NO: 85) or JBT-miR2.

In some embodiments, the cloning vector or expression vector disclosed herein includes a nucleotide sequence having, or having about, 85%, 90%, 91%, 92%, 93%, 94%, 95%, 96%, 97%, 98%, 99%, 100%, or a range between any two of these values, sequence identity to each of the nucleotide sequences set forth in SEQ ID NOs: 59-64. In some embodiments, the cloning vector or expression vector disclosed herein includes a nucleotide sequence having, or having about, 85%, 90%, 91%, 92%, 93%, 94%, 95%, 96%, 97%, 98%, 99%, 100%, or a range between any two of these values, sequence identity to each of the nucleotide sequences set forth in SEQ ID NOs: 86-89. In some embodiments, the cloning vector or expression vector disclosed herein includes a nucleotide sequence having, or having about, 85%, 90%, 91%, 92%, 93%, 94%, 95%, 96%, 97%, 98%, 99%, 100%, or a range between any two of these values, sequence identity to each of the nucleotide sequences set forth in SEQ ID NOs: 59-64 and SEQ ID NOs: 86-89. In some embodiments, the cloning vector or expression vector disclosed herein includes a nucleotide sequence having, or having about, 85%, 90%, 91%, 92%, 93%, 94%, 95%, 96%, 97%, 98%, 99%, 100%, or a range between any two of these values, sequence identity to the nucleotide sequence of SEQ ID NO: 8

Therapeutic Compositions and Pharmaceutical Formulations

In another aspect, disclosed herein are embodiments of a therapeutic composition that includes an effective amount of at least one therapeutic agent, and one or more of the followings: a) a composition comprising a plurality of microRNA (miR) antagonists as disclosed herein; b) an expression cassette as disclosed herein; and a cloning or expression vector as disclosed herein.

While it is possible for the agents to be administered as the raw substances, it is preferable, in view of their potency, to present them as a pharmaceutical formulation. Thus, in some embodiments of the compositions disclosed herein, the composition is further formulated into a pharmaceutical formulation. The term "pharmaceutical formulation", as used herein, refers to a composition suitable for administering to an individual that includes a pharmaceutical agent. For example, a pharmaceutical formulation according to some aspects and embodiments of the present disclosure may comprise an anti-miR antagonist disclosed herein and a sterile aqueous solution. For example, the pharmaceutical formulations of the present disclosure for human use comprise the agent, together with one or more acceptable carriers therefor and optionally other therapeutic ingredients. The carrier(s) must be "acceptable" in the sense of being compatible with the other ingredients of the formulation and not deleterious to the recipient thereof or deleterious to the inhibitory function of the active agent. Desirably, the pharmaceutical formulations should not include oxidizing agents and other substances with which the agents are known to be incompatible.

Accordingly, some embodiments disclosed herein relate to pharmaceutical formulations that include a therapeutic composition described herein and a pharmaceutically acceptable carrier. The formulations can also comprise additional ingredients such as diluents, stabilizers, excipients, and adjuvants. As used herein, "pharmaceutically acceptable" carriers, excipients, diluents, adjuvants, or stabilizers are the ones nontoxic to the cell or subject being exposed thereto (preferably inert) at the dosages and concentrations employed or that have an acceptable level of toxicity as determined by the skilled practitioner.

Buffers may also be included in the pharmaceutical formulations to provide a suitable pH value for the formulation. Suitable such materials include sodium phosphate and acetate. Sodium chloride or glycerin may be used to render a formulation isotonic with the blood. If desired, the formulation may be filled into the containers under an inert atmosphere such as nitrogen or may contain an anti-oxidant, and are conveniently presented in unit dose or multi-dose form, for example, in a sealed ampoule.

The carriers, diluents and adjuvants can include antioxidants such as ascorbic acid; low molecular weight polypeptides (e.g., less than about 10 residues); proteins such as serum albumin, gelatin or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™ or polyethylene glycol (PEG). In some embodiments, the physiologically acceptable carrier is an aqueous pH buffered solution.

Generally, the pharmaceutical formulations disclosed herein can be prepared by any one of the methods and techniques known in the art. For example, solid dosage forms can be prepared by wet granulation, dry granulation, direct compression, and the like. In some embodiments, the solid dosage forms of the present disclosure may be coated or otherwise compounded to provide a dosage form affording the advantage of prolonged action. For example, the tablet or pill can comprise an inner dosage and an outer dosage component, the latter being in the form of an envelope over the former. In some embodiments, the two components can be separated by an enteric layer, which serves to resist disintegration in the stomach and permit the inner component to pass intact into the duodenum or to be delayed in release. In these instances, a variety of materials can be used for such enteric layers or coatings, such materials including a number of polymeric acids and mixtures of polymeric acids with such materials as shellac, cetyl alcohol, and cellulose acetate.

Titers of the expression vector and/or one or more of the miRNA antagonists to be administered will vary depending, for example, on the particular expression vector, the mode of administration, the treatment goal, the individual, and the cell type(s) being targeted, and can be determined by methods standard in the art.

As will be readily apparent to one of ordinary skill in the art, the useful in vivo dosage of the expression vectors and/or one or more of the miRNA antagonists to be administered and the particular mode of administration will vary depending upon the age, weight, the severity of the affliction, and animal species treated, the particular expression vector that is used, and the specific use for which the expression vector and/or one or more of the miRNA antagonists is employed. The determination of effective dosage levels, that is the dosage levels necessary to achieve the desired result, can be accomplished by one of ordinary skill in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

For example, dosage regimens may be adjusted to provide the optimum desired response. For example, a single dose may be administered, or several divided doses may be administered over time, or the dose may be proportionally reduced or increased as indicated by the exigencies of the therapeutic situation. It is especially advantageous to formulate parenteral compositions and formulations in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the present disclosure are dictated by and directly dependent on (a) the unique characteristics of the therapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present disclosure.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present disclosure encompasses intra-patient dose-escalation as determined by the skilled artisan. Determining appropriate dosages and regimens for administration of therapeutic agents are well-known in the relevant art and would be understood to be encompassed by the skilled artisan once provided the teachings disclosed herein.

The expression vectors and/or the miRNA antagonists disclosed herein can be administered to a subject (e.g., a human) in need thereof. The route of the administration is not particularly limited. For example, a therapeutically effective amount of the recombinant viruses can be administered to the subject by via routes standard in the art. Non-limiting examples of the route include intramuscular, intravaginal, intravenous, intraperitoneal, subcutaneous, epicutaneous, intradermal, rectal, intraocular, pulmonary, intracranial, intraosseous, oral, buccal, or nasal. In some embodiments, the recombinant virus is administered to the subject by intramuscular injection. In some embodiments, the recombinant virus is administered to the subject by intravaginal injection. In some embodiments, the expression vectors and/or the miRNA antagonists is administered to the subject by the parenteral route (e.g., by intravenous, intramuscular or subcutaneous injection), by surface scarification or by inoculation into a body cavity of the subject. In some embodiments, the expression vectors and/or the miRNA antagonists are administered to muscle cells such as, cardiac muscle cells.

When administering these small miR oligonucleotide antagonists by injection, the administration may be by continuous infusion, or by single or multiple boluses. The dosage of the administered miR antagonist will vary depending upon such factors as the patient's age, weight, sex, general medical condition, and previous medical history. Typically, it is desirable to provide the recipient with a dosage of the molecule which is in the range of from about 1 pg/kg to 10 mg/kg (amount of agent/body weight of patient), although a lower or higher dosage may also be administered, In some embodiments, it may be desirable to target delivery of a therapeutic to the heart, while limiting delivery of the therapeutic to other organs. This may be accomplished by any one of a number of methods known in the art. In some embodiments, delivery to the heart of a therapeutic composition or pharmaceutical formulation described herein comprises coronary artery infusion. In certain embodiments, coronary artery infusion involves inserting a catheter through the femoral artery and passing the catheter through the aorta to the beginning of the coronary artery. In yet some other embodiments, targeted delivery of a therapeutic to the heart involves using antibody-protamine fusion proteins, such as those previously describe (Song E et al., *Nature Biotechnology*, 2005), to deliver the small miR oligonucleotide antagonists disclosed herein.

Actual administration of the expression vectors and/or the miRNA antagonists can be accomplished by using any physical method that will transport the expression vectors and/or the miRNA antagonists into the target tissue of the subject. For example, the expression vectors and/or the miRNA antagonists can be injected into muscle, the bloodstream, and/or directly into the liver. Pharmaceutical formulations can be prepared as injectable formulations or as topical formulations to be delivered to the muscles by transdermal transport.

For intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of the expression vectors and/or the miRNA antagonists as a free acid (DNA contains acidic phosphate groups) or a pharmacologically acceptable salt can be prepared in water suitably mixed with a surfactant such as hydroxypropylcellulose. A dispersion of the expression vectors and/or the miRNA antagonists can also be prepared in glycerol, liquid polyethylene glycols and mixtures thereof and in oils.

Under ordinary conditions of storage and use, these preparations contain a preservative to prevent the growth of microorganisms.

The expression vectors and/or the miRNA antagonists to be used can be utilized in liquid or freeze-dried form (in combination with one or more suitable preservatives and/or protective agents to protect the virus during the freeze-drying process). For gene therapy (e.g., of neurological disorders which may be ameliorated by a specific gene product) a therapeutically effective dose of the recombinant virus expressing the therapeutic protein is administered to a host in need of such treatment. The use of the expression vectors and/or the miRNA antagonists disclosed herein in the manufacture of a medicament for inducing immunity in, or providing gene therapy to, a host is within the scope of the present application.

In instances where human dosages for the expression vectors and/or the miRNA antagonists have been established for at least some condition, those same dosages, or dosages that are between about 0.1% and 500%, more preferably between about 25% and 250% of the established human dosage can be used. Where no human dosage is established, as will be the case for newly-discovered pharmaceutical formulations, a suitable human dosage can be inferred from $ED_{50}$ or $ID_{50}$ values, or other appropriate values derived from in vitro or in vivo studies, as qualified by toxicity studies and efficacy studies in animals A therapeutically effective amount of the expression vectors and/or the miRNA antagonists can be administered to a subject at various points of time. For example, the expression vectors and/or the miRNA antagonists can be administered to the subject prior to, during, or after the infection by a virus. The expression vectors and/or the miRNA antagonists can also be administered to the subject prior to, during, or after the occurrence of a disease (e.g., cancer). In some embodiments, the expression vectors and/or the miRNA antagonists is administered to the subject during cancer remission. In some embodiments, the expression vectors and/or the miRNA antagonists is administered prior to infection by the virus for immunoprophylaxis.

Alternatively or in addition, the dosing frequency of the expression vectors and/or the miRNA antagonists can vary. For example, the expression vectors and/or the miRNA antagonists can be administered to the subject about once every week, about once every two weeks, about once every month, about one every six months, about once every year, about once every two years, about once every three years, about once every four years, about once every five years, about once every six years, about once every seven years, about once every eight years, about once every nine years, about once every ten years, or about once every fifteen years. In some embodiments, the expression vectors and/or the miRNA antagonists is administered to the subject at most about once every week, at most about once every two weeks, at most about once every month, at most about one every six months, at most about once every year, at most about once every two years, at most about once every three years, at most about once every four years, at most about once every five years, at most about once every six years, at most about once every seven years, at most about once every eight years, at most about once every nine years, at most about once every ten years, or at most about once every fifteen years.

In some embodiments, a pharmaceutical kit is provided, wherein the kit comprises: any of the forgoing the therapeutic compositions and pharmaceutical formulations, and written information (a) indicating that the formulation is useful for inhibiting, in myocardial cells, such as, for example cardiomyocytes, the function of a gene associated with the heart disease and/or (b) providing guidance on administration of the pharmaceutical formulation.

IV. Methods of the Disclosure

Some embodiments disclosed herein relate to a method for treating a cardiac disease in a subject. The method includes administering or providing to the subject a therapeutic composition suitable for the treatment of cardiac diseases, wherein (a) the therapeutic composition is a composition comprising a plurality of microRNA (miR) antagonists as disclosed herein; (b) the therapeutic composition comprises an expression cassette as disclosed herein; or (c) the therapeutic composition comprises a cloning or expression vector as disclosed herein.

Some embodiments of the disclosure relate to a method for promoting cardiac muscle regeneration in a subject. The method includes administering or providing to the subject a therapeutic composition, wherein (a) the therapeutic composition is a composition comprising a plurality of microRNA (miR) antagonists as disclosed herein; (b) the therapeutic composition comprises an expression cassette as disclosed herein; or (c) the therapeutic composition comprises a cloning or expression vector as disclosed herein.

In some embodiments, a method for treating a cardiac disease or promoting cardiac muscle regeneration in a subject as disclosed herein optionally includes a process of identifying or selecting the subject as having or suspected of having a cardiac disease. In some embodiments, the process of identifying or selecting is carried out prior to administration of all therapeutic compositions and therapeutic agents or therapies. In some embodiments, the process of identifying or selecting is carried out prior to administration of at least one of the therapeutic composition and therapeutic agent or therapy.

In some embodiments, the cardiac disease is myocardial infarction, ischemic heart disease, heart failure (e.g., congestive heart failure), ischemic cardiomyopathy, hypertrophic cardiomyopathy, restrictive cardiomyopathy, alcoholic cardiomyopathy, viral cardiomyopathy, tachycardia-mediated cardiomyopathy, stress-induced cardiomyopathy, amyloid cardiomyopathy, arrhythmogenic right ventricular dysplasia, left ventricular noncompaction, endocardial fibroelastosis, aortic stenosis, aortic regurgitation, mitral stenosis, mitral regurgitation, mitral prolapse, pulmonary stenosis, pulmonary stenosis, pulmonary regurgitation, tricuspid stenosis, tricuspid regurgitation, congenital disorder, genetic disorder, or a combination thereof. In some particular embodiments, the cardiac disease is myocardial infarction. In some other particular embodiments, the cardiac disease is Ischemic heart disease where cardiac muscle regeneration is required. In yet some other particular embodiments, the cardiac disease is Duchenne muscular dystrophy.

In another aspect, disclosed herein are embodiments of methods for modulating proliferation of a cardiomyocyte and/or muscle cell. The method includes (1) introducing into a cardiomyocyte a therapeutic composition, wherein (a) the therapeutic composition is a composition comprising a plurality of microRNA (miR) antagonists as disclosed herein; (b) the therapeutic composition comprises an expression cassette as disclosed herein; or (c) the therapeutic composition comprises a cloning or expression vector as disclosed herein; and (2) allowing the cardiomyocyte obtained from (1) to divide, thereby modulating proliferation of the cardiomyocyte or muscle cell. In some embodiments, the introduction of the therapeutic composition into the cardiomyocyte includes transfecting the cardiomyocyte and/or muscle cell with at least one expression cassette or at least one viral vector comprising a nucleic acid sequence encoding the plurality of miR antagonists. In some embodiments, the method further includes measuring the proliferation of the cardiomyocyte and/or muscle cell. In some embodiments, the proliferation of the cardiomyocyte and/or muscle cell is increased compared to a control cardiomyocyte and/or muscle cell lacking the nucleic acid sequence encoding the plurality of miR antagonists.

In some embodiments of the methods disclosed herein, the administration step can be performed on cells in cell-culture (i.e., ex-vivo) or on cells in a living body. Accordingly, in some embodiments, the cardiomyocyte and/or muscle cell is in vivo. In some other embodiments, the cardiomyocyte and/or muscle is ex vivo. In some embodiments, the cardiomyocyte and/or muscle is of a human subject. In some embodiments, the human subject is selected or identified as suffering from a cardiac disease.

In some embodiments of the methods disclosed herein, where the therapeutic composition or pharmaceutical formulation includes expression cassettes or vectors comprising nucleotide sequences encoding a plurality of the miR antagonists as disclosed herein, the plurality of miR antagonists can be encoded by one or more expression cassettes or vectors. In some embodiments, the plurality of miR antagonists is encoded by a single expression cassette or vector. In some embodiments, the plurality of miR antagonists is encoded by 2, 3, 4, 5, 6, or more expression cassettes or vectors. In some embodiments, the plurality of miR antagonists can be encoded by the same type of expression cassette or vector. In some embodiments, the plurality of miR antagonists can be encoded by different types of expression cassette or vector.

In some embodiments of the methods disclosed herein, where the therapeutic composition or pharmaceutical formulation includes a cloning vector or expression vector, the vector can be derived from viruses, plasmids, cosmids, phages, or any combination thereof. In some embodiments, the vector is an integrating vector. In some embodiments, the vector is a viral vector. In some embodiments, the viral vector is a lentiviral vector or an adeno-associated viral (AAV) vector. In some embodiments, the viral vector is an adeno-associated viral (AAV) vector. In some embodiments, the viral vector is an AAV2/9 vector.

In one aspect, disclosed herein are embodiments of methods for increasing proliferation of a heart cell and/or increasing the expression and/or activity of proteins involved in muscle structure and/or function and/or regeneration. The method includes contacting or providing the heart cell with a combination of (1) a therapeutic composition, wherein (a) the therapeutic composition is a composition comprising a plurality of microRNA (miR) antagonists as disclosed herein; (b) the therapeutic composition comprises an expression cassette as disclosed herein; or (c) the therapeutic composition comprises a cloning or expression vector as disclosed herein; and (2) at least one additional therapeutic agent or therapy. In a related aspect, some embodiments disclosed herein relate to methods for inhibiting or reducing expression of a target microRNA (miR). The method includes contacting or providing the heart cell with a combination of (1) a therapeutic composition, wherein (a) the therapeutic composition is a composition comprising a plurality of microRNA (miR) antagonists as disclosed herein; (b) the therapeutic composition comprises an expression cassette as disclosed herein; or (c) the therapeutic composition comprises a cloning or expression vector as disclosed herein; and (2) at least one additional therapeutic agent or therapy. In the methods according to the foregoing aspects, the heart cell can generally be any heart cell. Non-limiting examples of heart cell suitable for the methods disclosed herein include cardiac fibroblasts, cardiac myocytes, endothelial cells, and vascular smooth muscle cells (VSMCs). In some embodiment, the heart cell is a cardiomyocyte or a skeletal muscle cell. In some embodiments, the heart cell is a cardiomyocyte. In some embodiments, the (miR) target gene is a gene associated with a cardiac disease.

In yet another aspect, disclosed herein are embodiments of methods for treating a muscular dystrophy (MD) disorder, comprising administering or providing to the subject a therapeutic composition, wherein (a) the therapeutic composition is a composition comprising a plurality of microRNA (miR) antagonists as disclosed herein; (b) the therapeutic composition comprises an expression cassette as disclosed herein; or (c) the therapeutic composition comprises a cloning or expression vector as disclosed herein, and wherein the administration of the therapeutic composition is performed in combination with an effective amount of at least one additional therapeutic agent or at least one additional therapy to provide a combination therapy. In some embodiments, wherein the muscular dystrophy disorder is associated with Amyotrophic Lateral Sclerosis (ALS), Charcot-Marie-Tooth Disease (CMT), Congenital Muscular Dystrophy (CMD), Duchenne Muscular Dystrophy (DMD), Emery-Dreifuss Muscular Dystrophy (EDMD), Inherited and Endocrine Myopathies, Metabolic Diseases of Muscle, Mitochondrial Myopathies (MM), Myotonic Muscular Dystrophy (MMD), Spinal-Bulbar Muscular Atrophy (SBMA), or a combination thereof.

V. Combination Therapies

In some embodiments, the therapeutic compositions and pharmaceutical formulations including the microRNA antagonists disclosed herein, such as those provided in the Sequence Listing, or those including a combination of the microRNA antagonists disclosed herein, or an expression cassette comprising a nucleotide sequence encoding one or more microRNA antagonists disclosed herein, or a vector comprising one or more of such expression cassettes, can be used in combination with one or more additional therapeutic agents. In some embodiments, the therapeutic compositions and pharmaceutical formulations including the microRNA antagonists disclosed herein, such as those provided in the Sequence Listing, or those including a combination of the microRNA antagonists disclosed herein, or an expression cassette comprising a nucleotide sequence encoding one or more microRNA antagonists disclosed herein, or a vector comprising one or more of such expression cassettes, can be used in combination with one or more therapeutic therapies.

Generally, any therapeutic approach pharmacological or non-pharmacological for muscular dystrophies can be suitably employed as additional therapeutic agents and therapies in the methods disclosed herein. Examples of additional therapeutic agents and therapies that can be used in combination with the microRNA antagonists disclosed herein, or a composition or formulation that include a combination of the microRNA antagonists disclosed herein, or an expression cassette comprising a nucleotide sequence encoding one or more microRNA antagonists disclosed herein, or a vector comprising one or more of such expression cassettes, include, but are not limited to, Idebenone, Eplerenone, VECTTOR, AVI-4658, Ataluren/PTC124/Translarna, BMN044/PRO044, CAT-1004, any gene therapy for MD including MicroDystrophin AAV gene therapy (SGT-001), Galectin-1 therapy (SB-002), LTBB4 (SB-001), rAAV2.5-

CMV-minidystrophin, glutamine, NFKB inhibitors, sarcoglycan, delta (35 kDa dystrophin-associated glycoprotein), insulin like growth factor-1 (IGF-1) expression, genome editing through the CRISPR/Cas9 system, any gene delivery therapy aimed at reintroducing a functional recombinant version of the dystrophin gene, Exon skipping therapeutics, read-through strategies for nonsense mutations, cell-based therapies, utrophin upregulation, myostatin inhibition, anti-inflammatories/anti-oxidants, mechanical support devices, any standard therapy for muscular dystrophy, and combinations thereof.

Additional therapeutic agents useful for the methods of the present disclosure also include, but are not limited to, anti-platelet therapy, thrombolysis, primary angioplasty, Heparin, magnesium sulphate, Insulin, aspirin, cholesterol lowering drugs, angiotensin-receptor blockers (ARBs) and angiotensin-converting enzyme (ACE) inhibitors. In particular, ACE inhibitors have clear benefits when used to treat patients with chronic heart failure and high-risk acute myocardial infarction; this is possibly because they inhibit production of inflammatory cytokines by angiotensin II. A non-limiting listing of additional therapeutic agents and therapies includes ACE inhibitors, such as Captopril, Enalapril, Lisinopril, or Quinapril; Angiotensin II receptor blockers, such as Valsartan; Beta-blockers, such as Carvedilol, Metoprolol, and bisoprolol; Vasodilators (via NO), such as Hydralazine, Isosorbide dinitrate, and Isosorbide mononitrate; Statins, such as Simvastatin, Atrovastatin, Fluvastatin, Lovastatin, Rosuvastatin or pravastatin; Anticoagulation drugs, such as Aspirin, Warfarin, or Heparin; or Inotropic agents, such as Dobutamine, Dopamine, Milrinone, Amrinone, Nitroprusside, Nitroglycerin, or nesiritide; Cardiac Glycosides, such as Digoxin; Antiarrhythmic agents, such as Calcium channel blockers, for example, Verapamil and Diltiazem or Class III antiarrhythmic agents, for example, Amiodarone, Sotalol or, defetilide; Diuretics, such as Loop diuretics, for example, Furosemide, Bumetanide, or Torsemide, Thiazide diuretics, for example, hydrochlorothiazide, Aldosterone antagonists, for example, Spironolactone or eplerenone. Alternatively or in addition, other treatments of cardiac disease are also suitable, such as Pacemakers, Defibrillators, Mechanical circulatory support, such as Counterpulsation devices (intraaortic balloon pump or non-invasive counterpulsation), Cardiopulmonary assist devices, or Left ventricular assist devices; Surgery, such as cardiac transplantation, heart-lung transplantation, or heart-kidney transplantation; or immunosuppressive agents, such as Myocophnolate mofetil, Azathiorine, Cyclosporine, Sirolimus, Tacrolimus, Corticosteroids Antithymocyte globulin, for example, Thymoglobulin or ATGAM, OKT3, IL-2 receptor antibodies, for example, Basilliximab or Daclizumab are also suitable.

In some embodiments, at least one of the additional therapeutic agents or therapies includes a biologic drug. In some embodiments, the at least one additional therapeutic agent or therapy comprises a gene therapy or therapeutic gene modulation agent. As used herein, therapeutic gene modulation refers to the practice of altering the expression of a gene at one of various stages, with a view to alleviate some form of ailment. It differs from gene therapy in that gene modulation seeks to alter the expression of an endogenous gene, for example through the introduction of a gene encoding a novel modulatory protein, whereas gene therapy concerns the introduction of a gene whose product aids the recipient directly. Modulation of gene expression can be mediated at the level of transcription by DNA-binding agents, which can be for example, artificial transcription factors, small molecules, or synthetic oligonucleotides. Alternatively or in addition, it can also be mediated post-transcriptionally through RNA interference.

The therapeutic compositions, pharmaceutical formulations disclosed herein and the additional therapeutic agents or therapies can be further formulated into final pharmaceutical preparations suitable for specific intended uses. In some embodiments, the therapeutic composition and the additional therapeutic agent or therapy are administered in a single formulation. In some embodiments, each of the therapeutic composition and the additional therapeutic agent or therapy is administered in a separate formulation. In some embodiments of the methods disclosed herein, the therapeutic composition and/or the additional therapeutic agent or therapy is administered to the subject in a single dose. In some embodiments, the therapeutic composition and/or the additional therapeutic agent or therapy is administered to the subject in multiple dosages. In some embodiments, the dosages are equal to one another. In some embodiments, the dosages are different from one another. In some embodiments, the therapeutic composition and/or the additional therapeutic agent or therapy is administered to the subject in gradually increasing dosages over time. In some embodiments, the therapeutic composition and/or the additional therapeutic agent or therapy is administered in gradually decreasing dosages over time.

The order of the administration of the therapeutic compositions and pharmaceutical formulations, with one or more additional therapeutic agent or therapy, can vary. In some embodiments, a therapeutic composition or pharmaceutical formulation disclosed herein can be administered prior to the administration of all additional therapeutic agent or therapy. In some embodiments, a therapeutic composition or pharmaceutical formulation disclosed herein can be administered prior to at least one additional therapeutic agent or therapy. In some embodiment, a therapeutic composition or pharmaceutical formulation disclosed herein can be administered concomitantly with one or more additional therapeutic agent or therapy. In yet still other embodiments, a therapeutic composition or pharmaceutical formulation disclosed herein can be administered subsequent to the administration of at least one additional therapeutic agent or therapy. In some embodiments, a therapeutic composition or pharmaceutical formulation disclosed herein can be administered subsequent to the administration of all additional therapeutic agent or therapy. In yet some embodiments, a therapeutic composition or pharmaceutical formulation disclosed herein and at least one additional therapeutic agent or therapy are administered in rotation (e.g., cycling therapy). For examples, in some embodiments, a therapeutic composition or pharmaceutical formulation disclosed herein and at least one additional therapeutic agent or therapy are cyclically administered to a subject. Cycling therapy involves the administration of a first active agent or therapy for a period of time, followed by the administration of a second active agent or therapy for a period of time and repeating this sequential administration. Cycling therapy can reduce the development of resistance to one or more therapies, avoid or reduce the side effects of one or more therapies, and/or improve the efficacy of treatment.

In some embodiments, intermittent therapy is an alternative to continuous therapy. For example, intermittent therapy can be used for a period of 6 months on, followed by a period of 6 months off. In some embodiments, one or more therapeutic agents or therapies are provided for one month on, followed by one month off. In some embodiments, one or more therapeutic agents or therapies are provided for three months on, followed by three months off. Accordingly, one or more of the therapeutic compositions or pharmaceutical formulations disclosed herein can be provided before, during and/or after administering one or more additional therapeutic agents or therapies, as described above.

All publications and patent applications mentioned in this specification are herein incorporated by reference to the same extent as if each individual publication or patent application was specifically and individually indicated to be incorporated by reference.

No admission is made that any reference cited herein constitutes prior art. The discussion of the references states what their authors assert, and the applicant reserves the right to challenge the accuracy and pertinence of the cited documents. It will be clearly understood that, although a number of information sources, including scientific journal articles, patent documents, and textbooks, are referred to herein, this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

EXAMPLES

Additional embodiments are disclosed in further detail in the following examples, which are not in any way intended to limit the scope of this disclosure or the claims.

Example 1

Design of Inhibitory Oligonucleotides for Specific microRNAs

This Example demonstrates the design and composition of synthetic oligonucleotides that can be used as antagonists of miR-99a-5p, miR-100-5p, Let-7a-5p, and Let-7c-5p.

Nucleotide sequences of the following human microRNAs were analyzed: miR-99a-5p, miR-100-5p, Let-7a-5p and Let-7c-5p. The sequences of these microRNAs and the sequences of the complementary antagonists are shown in Table 5 below. The bases highlighted in bold font correspond to base differences between let-7a-5p and let-7c-5p, or between miR-99a-5p and miR-100-5p. The seed sequence of all microRNAs is generally considered to be bases 2-8 starting from the 5' end. Without wishing to be bound by any particular theory, the nucleobases within the seed sequence of a microRNA are believed to be the bases that make the biggest contribution to deciding which mRNAs will be targeted by the microRNA. In the sequences listed in Table 5 below, the seed sequences are underlined.

TABLE 5

Nucleotide sequences of human miR-99-5p, miR-100-5p, Let-7a-5p, and Let-7c-5p and the complementary inhibitory sequences that can be incorporated into any suitable vectors such as, for example, viral vector for cardiac muscle generation.

```
>hsa-let-7a-5p MIMAT0000062
5'-UGA GGU AGU AGG UUG UAU AGUU-3'  Sense       (SEQ ID NO: 1)
3'-ACU CCA UCA UCC AAC AUA UCAA-5'  Anti-sense  (SEQ ID NO: 2)

>hsa-let-7c-5p MIMAT0000064
5'-UGA GGU AGU AGG UUG UAU GGUU-3'  Sense       (SEQ ID NO: 3)
3'-ACU CCA UCA UCC AAC AUA CCAA-5'  Anti-sense  (SEQ ID NO: 4)

>hsa-miR-99a-5p MIMAT0000097
5'-AAC CCG UAG AUC CGA UCU UGUG-3'  Sense       (SEQ ID NO: 5)
3'-UUG GGC AUC UAG GCU AGA ACAC-5'  Anti-sense  (SEQ ID NO: 6)

>hsa-miR-100-5p MIMAT0000098
5'-AAC CCG UAG AUC CGA ACU UGUG-3'  Sense       (SEQ ID NO: 7)
3'-UUG GGC AUC UAG GCU UGA ACAC-5'  Anti-sense  (SEQ ID NO: 8)
```

To further assess the sequence conservation of the corresponding microRNA homologs from different mammalian species were also examined. As shown in Table 6 below, the nucleotide sequences of miR-99a-5p, miR-100-5p, Let-7a-5p and Let-7c-5p from different mammalian species were observed to exhibit high degrees of sequence homology. The nucleotide sequences of Let-7a-5p are 100% homologous across all species analyzed. The nucleotide sequences of Let-7c-5p are also 100% homologous across all species analyzed. The sequence of miR-99a-5p from dog lacks nucleobase #, otherwise all other sequences are homologous. Dog is missing miR-100 miRNA, otherwise all other sequences are homologous.

TABLE 6

Sequence homology of miR-99a-5p, miR-100-5p, Let-7a-5p and Let-7c-5p homologs. Dre: *Danio rerio* (zebrafish), Hsa: *Homo sapiens* (human), Ptr : *Pan troglodytes* (chimpanzee), Cfa: *Canis familiaris* (dog), Ssc: *Sus scrofa* (minipig), Rno: *Rattus norvegicus* (rat), Mmu: *Mus musculus* (mouse).

| | | | |
|---|---|---|---|
| dre-let-7a-5p | UGAGGUAGUAGGUUGUAUAGUU | | (SEQ ID NO: 9) |
| mmu-let-7a-5p | UGAGGUAGUAGGUUGUAUAGUU | | (SEQ ID NO: 10) |
| rno-let-7a-5p | UGAGGUAGUAGGUUGUAUAGUU | | (SEQ ID NO: 11) |
| ssc-let-7a-5p | UGAGGUAGUAGGUUGUAUAGUU | | (SEQ ID NO: 12) |
| ptr-let-7a-5p | UGAGGUAGUAGGUUGUAUAGUU | | (SEQ ID NO: 13) |
| hsa-let-7a-5p | UGAGGUAGUAGGUUGUAUAGUU | | (SEQ ID NO: 14) |
| cfa-let-7a-5p | UGAGGUAGUAGGUUGUAUAGUU | | (SEQ ID NO: 15) |
| dre-let-7c-5p | UGAGGUAGUAGGUUGUAUGGUU | | (SEQ ID NO: 16) |
| mmu-let-7c-5p | UGAGGUAGUAGGUUGUAUGGUU | | (SEQ ID NO: 17) |
| rno-let-7c-5p | UGAGGUAGUAGGUUGUAUGGUU | | (SEQ ID NO: 18) |
| ssc-let-7c-5p | UGAGGUAGUAGGUUGUAUGGUU | | (SEQ ID NO: 19) |
| ptr-let-7c-5p | UGAGGUAGUAGGUUGUAUGGUU | | (SEQ ID NO: 20) |
| hsa-let-7c-5p | UGAGGUAGUAGGUUGUAUGGUU | | (SEQ ID NO: 21) |
| cfa-let-7c-5p | UGAGGUAGUAGGUUGUAUGGUU | | (SEQ ID NO: 22) |
| dre-miR-99a-5p | AACCCGUAGAUCCGAUCUUGUG | 22 | (SEQ ID NO: 23) |
| mmu-miR-99a-5p | AACCCGUAGAUCCGAUCUUGUG | 22 | (SEQ ID NO: 24) |
| rno-miR-99a-5p | AACCCGUAGAUCCGAUCUUGUG | 22 | (SEQ ID NO: 25) |
| cfa-miR-99a | AACCCGUAGAUCCGAUCUUGU | 21 | (SEQ ID NO: 26) |
| ssc-miR-99a | AACCCGUAGAUCCGAUCUUGUG | 22 | (SEQ ID NO: 27) |
| ptr-miR-99a | AACCCGUAGAUCCGAUCUUGUG | 22 | (SEQ ID NO: 28) |
| hsa-miR-99a-5p | AACCCGUAGAUCCGAUCUUGUG | 22 | (SEQ ID NO: 29) |
| dre-miR-100-5p | AACCCGUAGAUCCGAACUUGUG | | (SEQ ID NO: 30) |
| mmu-miR-100-5p | AACCCGUAGAUCCGAACUUGUG | | (SEQ ID NO: 31) |
| rno-miR-100-5p | AACCCGUAGAUCCGAACUUGUG | | (SEQ ID NO: 32) |
| ssc-miR-100 | AACCCGUAGAUCCGAACUUGUG | | (SEQ ID NO: 33) |
| ptr-miR-100 | AACCCGUAGAUCCGAACUUGUG | | (SEQ ID NO: 34) |
| hsa-miR-100-5p | AACCCGUAGAUCCGAACUUGUG | | (SEQ ID NO: 35) |

A total of twenty (20) anti-miR oligonucleotide compounds were designed, including ten for the let-7a-5p/let-7c-5p family and ten for the miR-99a-5p/miR-100-5p family. Two anti-miR designs targeting Let-7c-5p are JRX0100, JRX0102 and could be used to inhibit Let-7a-5p. Two anti-miR designs targeting Let-7a-5p are JRX0101 and JRX0103 and could be used to inhibit Let-7a-5p. Six anti-miR designs targeting both let-7a-5p and Let-7c-5p are JRX0104, JRX0105, JRX0106, JRX0107, JRX0108, and JRX0109. Five anti-miR designs targeting miR-100a are JRX0110, JRX0113, JRX0115, JRX0117, and JRX0119. Five anti-miR designs targeting miR-99a are JRX0111, JRX0112, JRX0114, JRX0116, and JRX0118. In this experiment, the designs used locked nucleic acid (LNA) chemistry modifications (+), in which the 2'-O-oxygen is bridged to the 4' position via a methylene linker to form a rigid bicycle, locked into a C3'-endo (RNA) sugar conformation allowing for resistance to nuclease degradation and extremely high affinity for its complementary RNA base. These modifications were particularly incorporated at each end of the molecules as designated by (+) in the sequences in TABLE 7 for stability, by e.g. enhancing resistance to exonucleases, and in the region complementary to the seed to increase affinity for their targeted miR and thus increased potency as a microRNA inhibitor. The backbone of the anti-miRs is phosphorothioate (indicated by * in Table 7 below) to enable a broad distribution in animals. This type of backbone functions by steric blockade of a specific microRNA in the RISC complex. The anti-miR oligonucleotide compounds were carefully kept relatively short, to avoid the possible of forming heteroduplexes, but long enough to bind plasma proteins efficiently and keep them from being filtered out of circulation in the kidneys and thus improve their biodistribution properties. A summary of 20 anti-miR designs and their respective target microRNAs is shown in Table 7 below.

As indicated in Table 7, some of the miR-7 family anti-miRs are 100% homologous to both let-7c-5p and c isoforms of interest and will inhibit both members. In contrast, the miR-99a-5p and miR-100 family anti-miRs are each only 100% homologous to one of the family members due to the position of the one base that is different in these miRs. However, in reality all of the anti-miRs designed for each of the two families can inhibit both members of the family of interest because, similarly to target recognition, the seed region (bases 2-8) is the most important region for determining anti-miR activity.

TABLE 7

Summary of twenty anti-miR designs disclosed herein

| Name | Target | Length | No. LNAs PLUS | Stretch of DNA | No. LNAs in Seed * | Nomenclature/ Sequence/Structure | Nomenclature/ Sequence/ Structure | SEQ ID NO |
|---|---|---|---|---|---|---|---|---|
| JRX0100 | let-7c | 19 | 9 | 3 | 5 | +C*+C*A*T*+A*C*A*A*+C*C*T*A*+C*T*+A*C*+C*+T*+C | CCATACAACCTACTACCTC | 36 |
| JRX0101 | let-7a | 19 | 9 | 3 | 5 | +C*+T*A*T*A*+C*A*A*C*+C*T*A*+C*+T*+A*C*+C*+T*+C | CTATACAACCTACTACCTC | 37 |
| JRX0102 | let-7c | 18 | 9 | 3 | 5 | +C*+A*T*A*C*A*+A*C*C*T*A*+C*T*+A*+C*C*+T*+C | CATACAACCTACTACCTC | 38 |
| JRX0103 | let-7a | 18 | 9 | 3 | 5 | +T*+A*T*A*C*+A*A*C*+C*T*A*C*+T*+A*+C*C*+T*+C | TATACAACCTACTACCTC | 39 |
| JRX0104 | let-7a/c | 17 | 9 | 3 | 5 | +A*T*A*C*A*+A*C*C*+T*A*+C*T*+A*+C*C*+T*+C | ATACAACCTACTACCTC | 40 |
| JRX0105 | let-7a/c | 17 | 9 | 3 | 5 | +A*+T*A*C*A*+A*C*C*T*A*+C*T*+A*C*+C*+T*+C | ATACAACCTACTACCTC | 41 |
| JRX0106 | let-7a/c | 16 | 8 | 3 | 5 | +T*+A*C*A*A*+C*C*T*A*+C*T*+A*+C*C*+T*+C | TACAACCTACTACCTC | 42 |
| JRX0107 | let-7a/c | 16 | 8 | 3 | 5 | +T*+A*C*A*A*+C*C*T*A*+C*T*+A*C*+C*+T*+C | TACAACCTACTACCTC | 43 |
| JRX0108 | let-7a/c | 15 | 8 | 3 | 5 | +A*+C*A*A*C*+C*T*A*+C*T*+A*+C*C*+T*+C | ACAACCTACTACCTC | 44 |
| JRX0109 | let-7a/c | 15 | 9 | 3 | 6 | +A*+C*A*A*+C*C*T*A*+C*+T*+A*C*+C*+T*+C | ACAACCTACTACCTC | 45 |
| JRX0110 | miR-100 | 19 | 9 | 3 | 5 | +C*+A*A*G*+T*T*C*G*+G*A*T*C*+T*A*+C*G*+G*+G*+T | CAAGTTCGGATCTACGGGT | 46 |
| JRX0111 | miR-99 | 19 | 9 | 3 | 5 | +C*+A*A*G*A*+T*C*G*G*+A*T*C*+T*+A*C*G*+G*+G*+T | CAAGATCGGATCTACGGGT | 47 |
| JRX0112 | miR-99 | 18 | 9 | 3 | 5 | +A*+A*G*+A*T*C*G*+G*A*T*C*+T*+A*+C*G*+G*+G*+T | AAGATCGGATCTACGGGT | 48 |
| JRX0113 | miR-100 | 18 | 9 | 3 | 5 | +A*+A*G*T*T*+C*G*G*+A*T*C*T*+A*+C*G*+G*+G*+T | AAGTTCGGATCTACGGGT | 49 |
| JRX0114 | miR-99 | 17 | 9 | 3 | 5 | +A*+G*A*T*C*+G*G*A*+T*C*+T*A*+C*G*+G*+G*+T | AGATCGGATCTACGGGT | 50 |
| JRX0115 | miR-100 | 17 | 9 | 3 | 5 | +A*+G*T*T*C*+G*G*+A*T*C*+T*A*+C*G*+G*+G*+T | AGTTCGGATCTACGGGT | 51 |
| JRX0116 | miR-99 | 16 | 8 | 3 | 5 | +G*+A*T*C*G*+G*A*T*C*+T*A*+C*+G*G*+G*+T | GATCGGATCTACGGGT | 52 |
| JRX0117 | miR-100 | 16 | 8 | 3 | 5 | +G*+T*T*C*G*+G*A*T*C*+T*A*+C*G*+G*+G*+T | GTTCGGATCTACGGGT | 53 |
| JRX0118 | miR-99 | 15 | 8 | 3 | 5 | +A*+T*C*G*+G*+A*T*C*+T*A*+C*+G*+G*+T | ATCGGATCTACGGGT | 54 |
| JRX0119 | miR-100 | 15 | 9 | 3 | 6 | +T*+T*C*G*+G*A*T*C*+T*+A*+C*G*+G*+G*+T | TTCGGATCTACGGGT | 55 |

As described in further detail below, the inhibitory activity of these synthetic anti-miRs can be subsequently assessed by using a commercially reporter vector system, pMIR-REPORT™ miRNA Expression Reporter Vector System, made available by Applied Biosystems® (see., e.g., FIG. 3) (Part Number AM5795, Applied Biosystems). In this system, microRNA binding sites of interest are inserted the multiple cloning sites located downstream of the coding sequence of the reporter luciferase.

Example 2

Design of Adeno-Viral Vector JBT-miR1

This Example summarizes experimental results illustrating the design of a modified hairpin Zip construct and vector expressing inhibitory sequences of the microRNAs miR-99a, miR-100-5p, miR-Let-7a-5p, and miR-Let-7c-5p using RNAi technology. In this experiment, RNAi technology was implemented within a target cell in the form of a base-pair short hairpin (sh) RNA (shRNA), which is processed into an approximately 20 base pair small interfering RNA or through the endogenous miR pathway. A small hairpin RNA or short hairpin RNA (shRNA) is typically defined as an artificial RNA molecule with a tight hairpin turn that can be used to silence target gene expression via RNA interference (RNAi). To evaluate the potential therapeutic use of anti-miR-99/100 and anti-Let-7a/c to regenerate cardiac muscle in the murine heart, two recombinant viruses expressing complementary inhibitory sequences to Let-7a/c and miR-99/100 were made by AAV2 Inverted Terminal Repeat (ITR) sequences cross packaged into AAV9 capsids (AAV2/9). The AAV2/9 serotype has clear cardiac tropism. Viral delivery of complementary sequences to miRs is a common approach. In this experiment, AAV vectors were selected as being optimal in cardiovascular gene therapy since they a) contain no viral protein-coding sequences to stimulate an immune response, b) do not require active cell division for expression to occur and c) have a significant advantage over adenovirus vectors because of their stable, long-term expression of recombinant genes in cardiomyocytes in vivo.

In this experiment, a modified hairpin Zip construct expressing (1) the Let-7a-5p and miR-99a-5p inhibitory sequences under the H1 promoter and U6 promoter, respectively; and (2) Let-7c-5p and miR-100-5p inhibitory sequences under the regulation of the H1 promoter and U6 promoter, respectively. A summary of the nucleotide sequences of anti-miR antagonists and loop sequence inserted into the pAV-4in1shRNA-GFP vector to generate the viral vector JBT-miR1 is provided in Table 8 below. In this experiment, the nucleotide sequences encoding the foregoing antagonists were cloned in the pAV-4in 1 shRNA-GFP vector (FIG. 1). The nucleotide sequences corresponding to the four miR inhibitory sequences were inserted into the pAV-4in1shRNA-GFP vector between the ITR sites of the vector and specifically within the BamH1 and HindIII cloning site, and were separated by a loop sequence, TGTGCTT (SEQ ID NO: 56). In the resulting vector, expression of each inhibitory sequence was regulated by alternate human U6 promoter or the H1 promoter driving the expression of a short hairpin RNA (shRNA) against miR-99a-5p, 100, Let-7a-5p and Let-7c.

As shown in FIG. 1, also inserted into the vector was a CMV promoter driving the expression of a Green Fluorescent Protein (GFP) reporter, which in turn allows for detection in various tissues for preclinical studies, followed by a Simian virus 40 (SV40) sequence which is a polyomavirus binding site that initiates DNA replication at the origin of replication allowing for replication of in mammalian cells expressing SV40 large T. It is contemplated however that, these sequences can also be suitably removed from vectors designed for use in human drugs.

Vector genomes with AAV2 ITR sequences were cross-packaged into AAV9 capsids via triple transfection of AAV-293 cells (J. Fraser Wright, Human Gene Therapy, 20:698-706, July 2009), and then purified by iodixanol gradient centrifugation. Titers of the AAV vectors, which is defined as viral genomes (vg)/ml, were then determined by a qPCR-based assay. In this experiments, the following primers were used for amplifying the mouse U6 promoter: 5'-TCGCACA-GACTTGTGGGAGAA-3' (SEQ ID NO: 57) (forward) and 5' CGCACATTAAGCCTCTATAGTTACTAGG-3' (SEQ ID NO: 58) (reverse).

Known copy numbers of plasmids carrying the corresponding expression cassettes were used to construct standard curves for quantification. The virus was manufactured and sequenced by Vigene Biosciences Inc. (Rockville, Md.) using manufacturer's recommended safety precautions and procedures.

TABLE 8

Summary of the nucleotide sequences of anti-miR antagonists and loop sequence inserted into the BamH1 and HindIII cloning site of the pAV-4in1 shRNA-GFP vector to generate the viral vector JBT-miR1.

| Target | Hairpin | SEQ ID NO |
| --- | --- | --- |
| let-7a-5p | GTGAGGTAGTAGGTTGTATAGTTTCAAGAGAAC TATACAACCTACTACCTCATTTTT | 59 |
| miR-99a-5p | GAACCCGTAGATCCGATCTTGTGTCAAGAGCAC AAGATCGGATCTACGGGTTTTTT | 60 |
| (H1-)let-7a-5p & (U6)-miR-99a-5p | GTGAGGTAGTAGGTTGTATAGTTTCAAGAGAAC TATACAACCTACTACCTCATTTTTGAGCTCAAAA AAACCCGTAGATCCGATCTTGTGCTCTTGACACA AGATCGGATCTACGGGTTC | 61 |
| let-7c-5p | GTGAGGTAGTAGGTTGTATGGTTTCAAGAGAAC CATACAACCTACTACCTCATTTTT | 62 |
| miR-100-5p | GAACCCGTAGATCCGAACTTGTGTCAAGAGCAC AAGTTCGGATCTACGGGTTTTTT | 63 |

TABLE 8-continued

Summary of the nucleotide sequences of anti-miR antagonists and loop sequence inserted into the BamH1 and HindIII cloning site of the pAV-4in1 shRNA-GFP vector to generate the viral vector JBT-miR1.

| Target | Hairpin | SEQ ID NO |
|---|---|---|
| (H1-)let-7C-5p & (U6)-miR-100-5p | GTGAGGTAGTAGGTTGTATGGTTTCAAGAGAAC CATACAACCTACTACCTCATTTTTGAGCTCAAAA AAACCCGTAGATCCGAACTTGTGCTCTTGACAC AAGTTCGGATCTACGGGTTC | 64 |

The nucleotide sequence of the JBT-miR1 viral vector design is set forth at SEQ ID NO: 85 in the Sequence Listing.

As described in Example 1 above, a total of twenty (20) anti-miR oligonucleotide compounds were designed. The sequences of these anti-miR oligonucleotide compounds are shown in Table 9 below. Any combination of the sequences of anti-miR oligonucleotide compounds disclosed in Table 9 below can be inserted into the BamH1 and HindIII cloning site of the pAV-4in1shRNA-GFP vector to generate other viral delivery systems for miR-99a, miR-100-5p, Let-7a-5p and Let-7c-5p inhibition.

The nucleotide sequence of the JBT-miR1 viral vector design is set forth at SEQ ID NO: 85 in the Sequence Listing.

Example 3

Inhibitory Activity of Viral Vector JBT-miR1 in Myocardium In Vivo

This Example summarizes experimental results demonstrating that the viral vector JBT-miR1 constructed as

TABLE 9

| Target | Length | No. LNAs PLUS | Stretch of DNA | No. LNAs in Seed * | Sequence | SEQ ID NO |
|---|---|---|---|---|---|---|
| let-7c | 19 | 9 | 3 | 5 | CCATACAACCTACTACCTC | 65 |
| let-7a | 19 | 9 | 3 | 5 | CTATACAACCTACTACCTC | 66 |
| let-7c | 18 | 9 | 3 | 5 | CATACAACCTACTACCTC | 67 |
| let-7a | 18 | 9 | 3 | 5 | TATACAACCTACTACCTC | 68 |
| let-7a/c | 17 | 9 | 3 | 5 | ATACAACCTACTACCTC | 69 |
| let-7a/c | 17 | 9 | 3 | 5 | ATACAACCTACTACCTC | 70 |
| let-7a/c | 16 | 8 | 3 | 5 | TACAACCTACTACCTC | 71 |
| let-7a/c | 16 | 8 | 3 | 5 | TACAACCTACTACCTC | 72 |
| let-7a/c | 15 | 8 | 3 | 5 | ACAACCTACTACCTC | 73 |
| let-7a/c | 15 | 9 | 3 | 6 | ACAACCTACTACCTC | 74 |
| miR-100 | 19 | 9 | 3 | 5 | CAAGTTCGGATCTACGGGT | 75 |
| miR-99 | 19 | 9 | 3 | 5 | CAAGATCGGATCTACGGGT | 76 |
| miR-99 | 18 | 9 | 3 | 5 | AAGATCGGATCTACGGGT | 77 |
| miR-100 | 18 | 9 | 3 | 5 | AAGTTCGGATCTACGGGT | 78 |
| miR-99 | 17 | 9 | 3 | 5 | AGATCGGATCTACGGGT | 79 |
| miR-100 | 17 | 9 | 3 | 5 | AGTTCGGATCTACGGGT | 80 |
| miR-99 | 16 | 8 | 3 | 5 | GATCGGATCTACGGGT | 81 |
| miR-100 | 16 | 8 | 3 | 5 | GTTCGGATCTACGGGT | 82 |
| miR-99 | 15 | 8 | 3 | 5 | ATCGGATCTACGGGT | 83 |
| miR-100 | 15 | 9 | 3 | 6 | TTCGGATCTACGGGT | 84 | described in Example 2 can decrease late gadolinium enhancement of the LV in CD1 mice.

In this experiment, CD1 mice were anesthetized with Ketamine (100 mg/kg) and Xylazine (10 mg/kg) and intubated with a pressure ventilator (Kent Scientific, CT). Throughout the procedure, the animal was intubated via the trachea, and mechanically ventilated with room air (respiratory rate 55-65 breaths/min, tidal volume 2.5 ml) (Model 687—Harvard Apparatus). A skin incision was made from the midsternal line toward the left armpit, and the chest opened with a 1-cm lateral cut along the left side of the sternum, cutting between the 3rd and 4th ribs to expose the LV. The ascending aorta and main pulmonary artery would be then identified and the LAD located between the left and right ventricles (RV). LAD occlusion was performed by tying an 8-0 PROLENE® suture ligature on a piece of PE-10 tubing. Blanching of the territory of perfusion of the LAD, along with acute ST segment elevation on limb-lead EKG leads, and a whitening of the LV would certify vessel occlusion.

JBT-miR1 or control virus was then administered at a dose of 6×1011 vg/mouse diluted in 60 µl of saline by intracardiac injection into the myocardium bordering the infarct zone using an insulin syringe with incorporated 30-gauge needle. The mice were left for 3 weeks and then subject to cardiac MRI. As shown in Table 10, it was observed that mice transformed with JBT-miR1 were found to decrease late gadolinium enhancement of the LV in CD1 mice with permanent LAD ligation 3 weeks following an intracardiac injection of JBT-miR1 compared with a virus expressing GFP.

TABLE 10

| ID | BW (g) | AAV | LV Mass (mg) | LGE MI Size (% LV mass) |
|---|---|---|---|---|
| GFP Control | | | | |
| 10 | 36 | GFP Control | 162.5 | 10.68 |
| 11 | 36 | GFP Control | 165.9 | 27.59 |
| Mean | 36 | | 164.2 | 19.14 |
| SD | 0 | | 2.4 | 11.96 |
| JBT | | | | |
| 13 | 39 | JBT | 204.0 | 14.31 |
| 14 | 36 | JBT | 156.8 | 10.90 |
| Mean | 38 | | 180.4 | 12.61 |
| SD | 2 | | 33.4 | 2.41 |

Figure 2A:
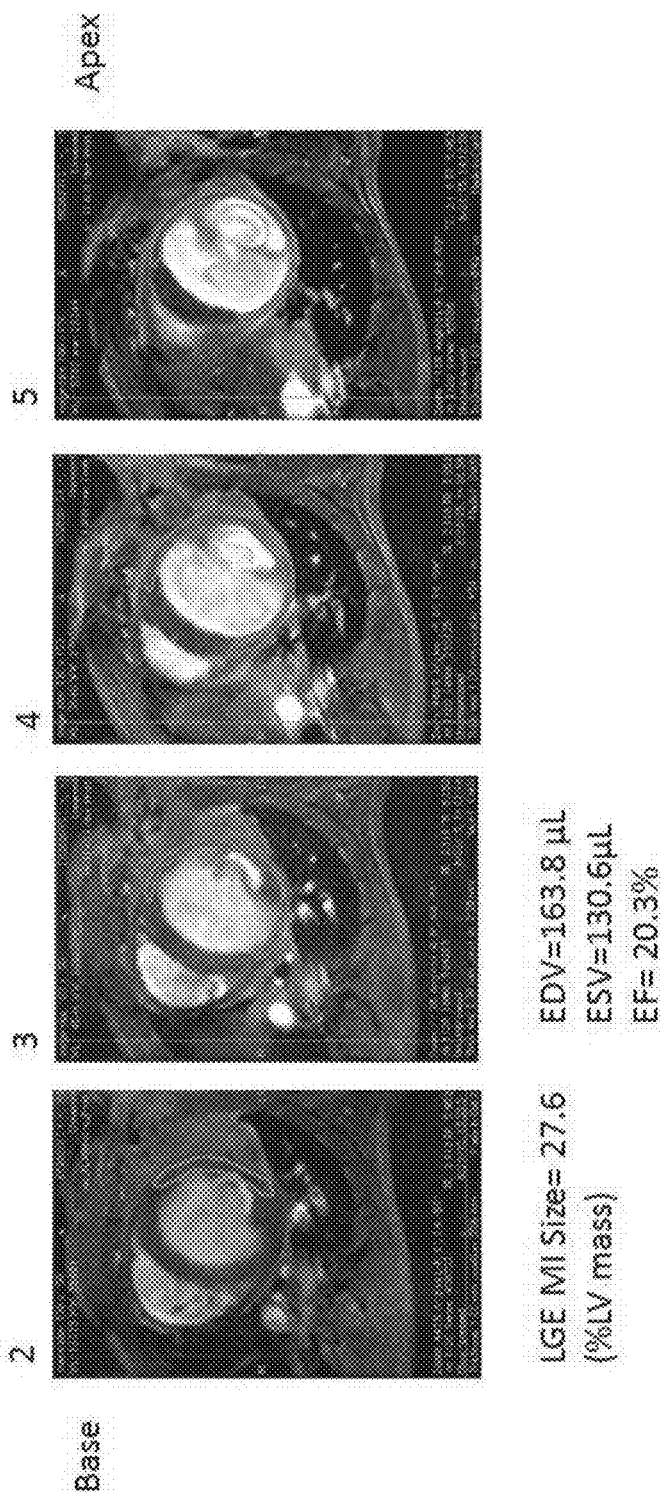
FIGS. 2A-2B pictorially summarize the results of cardiac MRI imaging experiments in which the cardiac MRI images of control GFP virus (FIG. 2A) versus JBT-miR1 (FIG. 2B) were observed to decrease late gadolinium enhancement of the Left Ventricle (LV) in CD1 mice with permanent LAD ligation 3 weeks following an intracardiac injection of JBT-miR1 when compared with a virus expressing GFP.
Figure 2B:
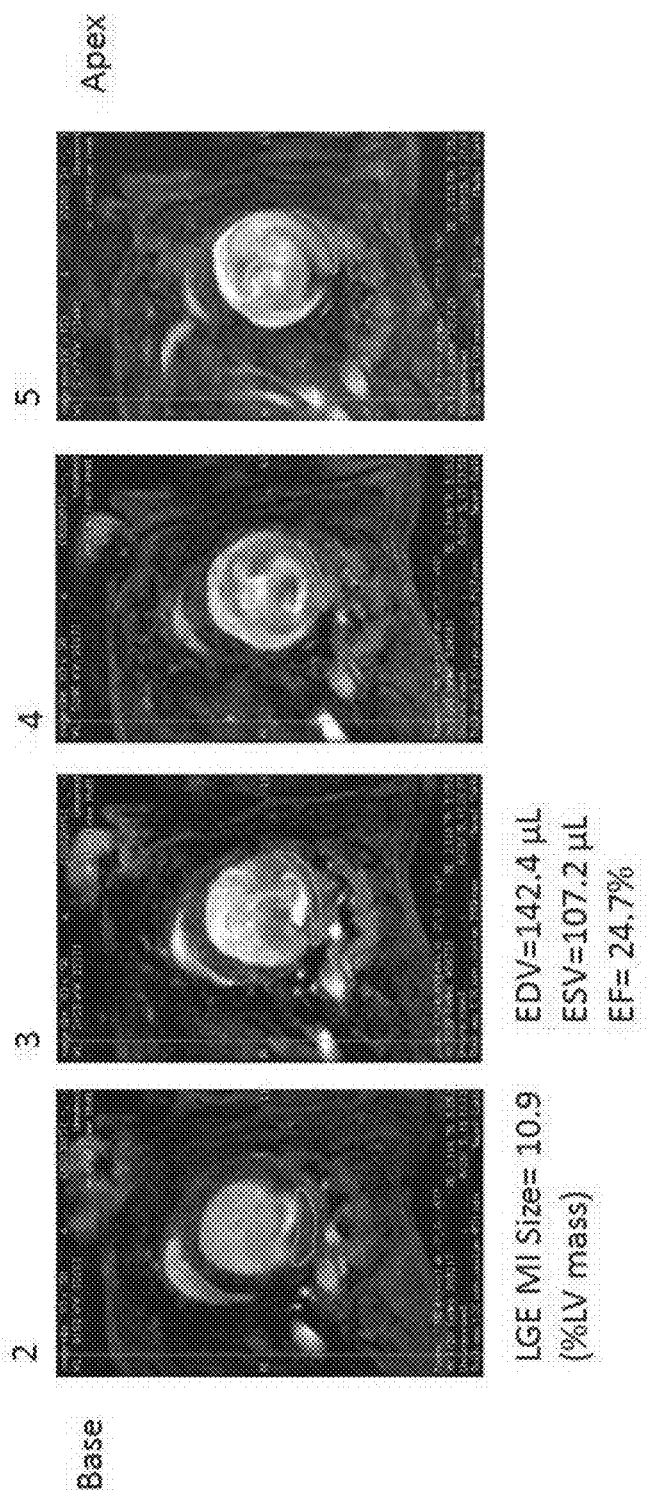

FIGS. 2A-2B pictorially summarize the results of cardiac MRI imaging experiments in which the cardiac MRI images of control GFP virus (FIG. 2A) versus JBT-miR1 (FIG. 2B) were demonstrated to decrease late gadolinium enhancement of the LV in CD1 mice with permanent LAD ligation 3 weeks following an intracardiac injection of vector JBT-miR1 when compared with a virus expressing GFP. For this model male, CD1 mice (8-12 weeks of age) weighing ~30-40 grams were subject to permanent ischemia as before. In this experiment, MRI was performed on a horizontal Bruker Biospec® 7T/20 MRI system (Bruker, Germany) on anesthetized mice (SA Instruments, NY). For end-diastolic (ED) and end-systolic (ES) images, volumetric data were determined from the product of compartment area and slice thickness (1 mm). LVED and ES volumes (EDV and ESV) were calculated from the summation of all slices and the EF derived. EDV multiplied by myocardial specific gravity, γ (1.055 g/cm3) calculates LV mass. MI size: ED images of each slice were selected for scar delineation. The sizes of the contrast-enhanced areas in the MR images were plotted against the corresponding areas obtained from TTC staining. Infarction size was expressed as the % of LV mass.

As illustrated in Table 11, two-dimensional (2D) echocardiography analysis showed a significant increase in cardiac output of CD1 mice with permanent LAD ligation 3 weeks following an intracardiac injection of JBT-miR1 compared with a virus expressing GFP. In this experiment, 2D-Echo was performed on anesthetized mice on Day 5 and Day 14 and day 21 by using a Hewlett-Packard/Phillips 5500 machine and a 15-MHz transducer.

TABLE 11

| | | Cardiac Output (µL/min) | | |
|---|---|---|---|---|
| ID | Type | 5 Day | 2 Week | 3 Week |
| 10 | AAV-GFP | 11537.2 | 7951.7 | 12984.0 |
| 11 | AAV-GFP | 16287.7 | 9265.4 | 15015.0 |
| 12 | AAV-GFP | 10833.1 | 13410.9 | 10848.0 |
| Mean | | 12886.0 | 10209.3 | 12949.0 |
| SD | | 2966.9 | 2849.4 | 2083.7 |
| 13 | AAV-JBT-miR1 | 18893.2 | 22919.6 | 23414.6 |
| 14 | AAV-JBT-miR1 | 17134.0 | 13918.5 | 22494.0 |
| 16 | AAV-JBT-miR1 | 13492.2 | 14359.3 | 18612.0 |
| 17 | AAV-JBT-miR1 | 5670.0 | 8409.5 | 21129.6 |
| Mean | | 13797.4 | 14901.7 | 21412.6 |
| SD | | 5866.5 | 5991.6 | 2089.7 |
| Ttest | | | | |
| GFP vs. JBT | | 0.8001 | 0.2346 | 0.0044 |

Example 4

Design of Viral Vector JBT-miR2

This Example summarizes experimental results illustrating the design of another viral vector, named JBT-miR2, which expresses tough decoys (also known as TuDs) that can be superior to zips (JBT-miR1) (Takeshi et al. 2009). In brief, four 120-based oligonucleotide sequences were inserted into between the ITR sites of the vector and in the BamH1 and HindIII cloning site to generate the TuDs that can inhibit the let-7 and miR-99a-5p families when inserted into a viral delivery system. In the nucleotide sequences of the foregoing oligonucleotides shown below, bold characters correspond to the respective miR binding sites.

let-7a-5p
(SEQ ID NO: 86)
GACGGCGCTAGGATCATCAACAACTATACAACCAATGTACTACCTCACA

AGTATTCTGGTCACAGAATACAACAACTATACAACCAATGTACTACCTC

ACAAGATGATCCTAGCGCCGTC.

let-7a-5p Reverse Complement
(SEQ ID NO: 87)
GACGGCGCTAGGATCATCTTGTGAGGTAGTACATTGGTTGTATAGTTGT

TGTATTCTGTGACCAGAATACTTGTGAGGTAGTACATTGGTTGTATAGT

TGTTGATGATCCTAGCGCCGTC miR-99a-5p
(SEQ ID NO: 88)
GACGGCGCTAGGATCATCAACCACAAGATCGGAAATGTCTACGGGTACA

AGTATTCTGGTCACAGAATACAACCACAAGATCGGAAATGTCTACGGGT

ACAAGATGATCCTAGCGCCGTC

-continued miR-99a-5p Reverse Complement (SEQ ID NO: 89)
GACGGCGCTAGGATCATCTTGTACCCGTAGACATTTCCGATCTTGTGGT

TGTATTCTGTGACCAGAATACTTGTACCCGTAGACATTTCCGATCTTGT

GGTTGATGATCCTAGCGCCGTC.

In some experiments, restriction sites were added to the oligonucleotides which in turn facilitate their subcloning into the appropriate vectors. The 5' end of these sequences were cloned adjacent to the promoter sequence (e.g., the U6 promoter) and the 3' end was cloned against a PolII termination sequence (e.g., TTTTT).

Example 5

In Vitro Bioactivity of Anti-miR Oligonucleotides

This Example summarizes the results of the experiments performed to assess the activity of MicroRNA (miR) antagonists (anti-miRs) to let-7a/c and miR-99/100, ex vivo in rat neonatal ventricular myocytes and Hela cells, using the pMIR-REPORT™ miRNA Expression Reporter Vector System (Part Number AM5795, Applied Biosystems®). The pMIR-REPORT™ miRNA Expression Reporter Vector System consists of an experimental firefly luciferase reporter vector and an associated β-gal reporter control plasmid. By inserting predicted miRNA target sequences in the multiple cloning site located downstream of the coding sequence of the reporter, these vectors are often used to conduct accurate, quantitative evaluations of miRNA function. This system is also often used to evaluate siRNA target sites and to analyze the influence of 3' UTR sequences on gene expression.

Without being bound be any particular theory, it is believed that the unmodified pMIR-REPORT™ should have maximal luciferase activity when transfected in to Hela cells or rat neonatal ventricular cardiac myocytes. Stated differently, by inserting the predicted miRNA target sequences for miR-99 (Luciferase reporter 1, LUC 1), miR-100 (Luciferase reporter 2, LUC 2) and Let-7a-5p (Luciferase reporter 3, LUC 3) and Let-7c-5p (Luciferase reporter 4, LUC 4) into the multiple cloning site of the pMIR-REPORT™, the luciferase activity of the resulting vectors (LUC 1, LUC2, LUC3 and LUC 4) would be significantly less than the pMIR-REPORT™ alone.

The modified Luciferase miRNA Expression Reporter Vectors constructed as described above, i.e., pMIR-REPORT LUC 1, LUC 2, LUC 3 and LUC 4; can be used to conduct accurate, quantitative evaluations of miRNA function, such that inhibition of endogenous miR members in HeLa cells and cardiac myocytes would lead to a dose-dependent increase in luciferase activity compared to the LUC 1, LUC 2, LUC 3 and LUC 4 vectors alone.

Method

Complementary sequences to the microRNAs miR-99, miR-100, Let-7a-5p and Let-7c-5p were designed and cloned into the multiple cloning site of the pMIR-REPORT™ miRNA Expression Reporter Vector System. The resulting vectors were named LUC 1, LUC 2, LUC 3 and LUC 4 expression vectors, respectively. Hela cells were cultured in 96 well tissue culture plates and co-transfected with 50 ng/well of purified DNA of a modified LUC vector (i.e., LUC 1, LUC 2, LUC 3, or LUC 4 vector) and 10 ng/well of a Beta-Galactosidase (β-gal) reporter plasmid, together with increasing concentrations of anti-miRs (0-50 nM) for up to 5 hours using Lipofectamine® 2000 Reagent (Life Technologies). Similarly, neonatal rat ventricular cardiac myocytes were cultured in 24 well tissue culture plates and co-transfected with 500 ng/well of LUC 1, LUC 2, LUC 3, and LUC 4 DNA and 100 ng/well of β-gal reporter plasmid to confirm transfection efficiency. At forty-eight hours after transfection, the transfected cells were harvested and the cell lysates were assayed for Luciferase activity and β-gal activity. The luciferase activity was normalized to β-gal activity and expressed as fold activation over the LUC 1, LUC 2, LUC 3, and LUC 4 plasmids alone.

Figure 3:
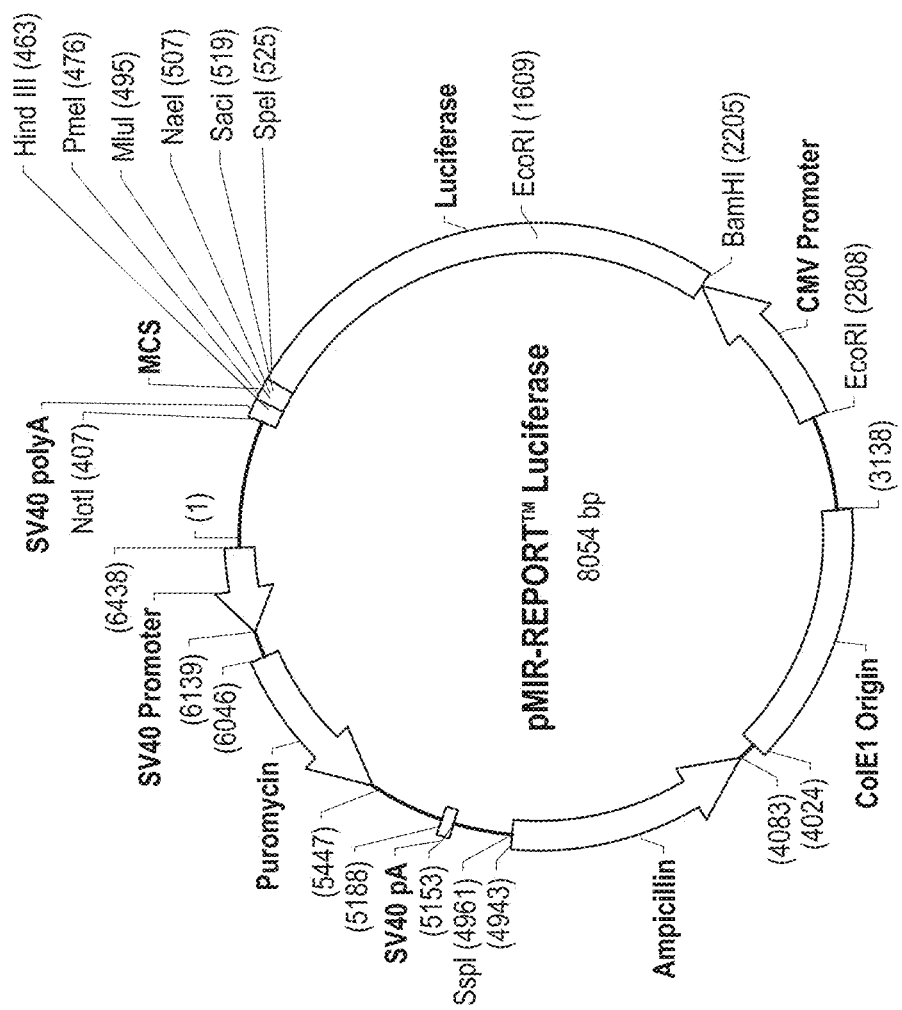
FIG. 3 is a schematic representation of a non-limiting exemplary pMIR-REPORT™ Luciferase miRNA expression reporter vector that contains a firefly luciferase reporter gene.

FIG. 3 schematically shows the pMIR-REPORT™ Luciferase miRNA expression reporter vector, which contains a firefly luciferase reporter gene under the control of a cauliflower virus (CMV) promoter/termination system. The 3' UTR of the luciferase gene contains a multiple cloning site for insertion of predicted miRNA binding targets or other nucleotide sequences. By inserting a predicted miRNA target sequence into the multiple cloning sites of the pMIR-REPORT vector, the luciferase reporter can be then subjected to regulation that mimics the miRNA target.

Figure 4:
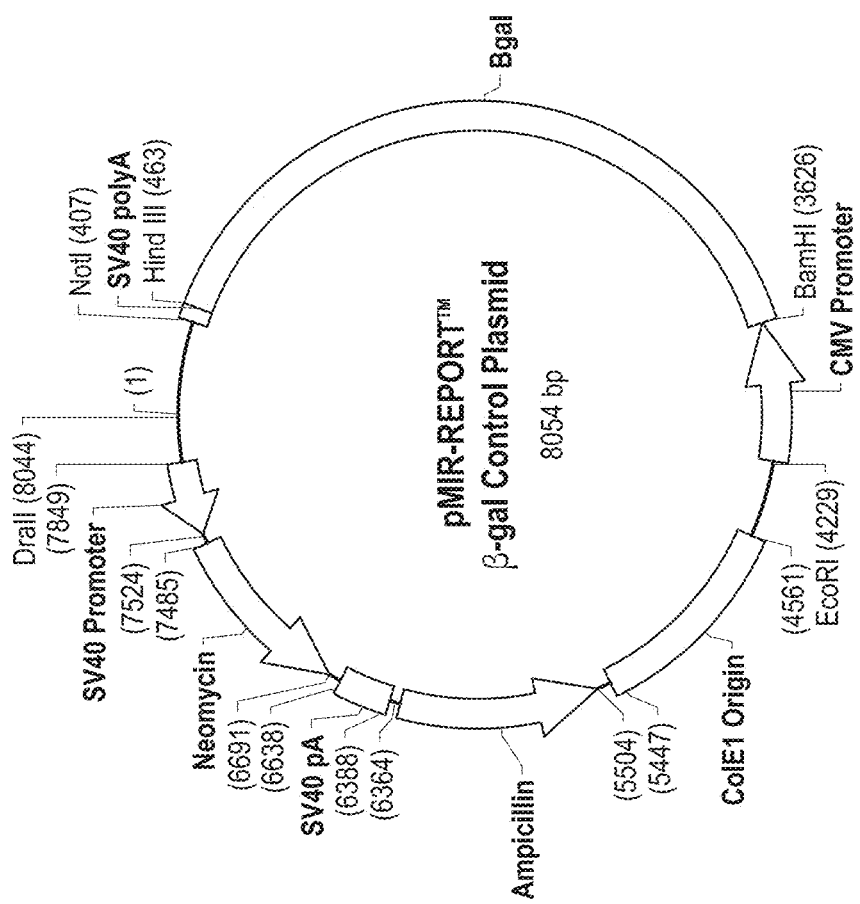
FIG. 4 is a schematic representation of a non-limiting exemplary pMIR-REPORT™ miRNA β-Galactosidase expression reporter vector that contains a β-Galactosidase reporter gene.

FIG. 4 schematically shows the pMIR-REPORT™ miRNA β-Galactosidase expression reporter vector carrying the reporter gene β-Galactosidase, which is designed for transfection normalization. Typically, β-gal expression from this control plasmid can be used to normalize variability due to differences in cell viability and transfection efficiency.

Construction of the pMIR-REPORT™ vectors for miR-99, miR-100, Let-7a-5p and let-7c:

The following oligonucleotides (in bold) were purchased from Integrated DNA Technologies (IDT), San Diego. Underlined are the miRNA binding sites corresponding to the sequences complementary with miRNA, which were subsequently inserted downstream of the coding sequence of the luciferase gene.

```
>hsa-miR-99a-5p MIMAT0000097
                                      (SEQ ID NO: 90)
5'-AAC CCG UAG AUC CGA UCU UGUG-3'

(SEQ ID NO: 91)
CACA AGA TCG GAT CTA CGG GTT

99a FORWARD PRIMER:
                                      (SEQ ID NO: 92)
5'-AACACTAGTCACAAGATCGGATCTACGGGTTAAGCTTGTT-3'

99a REVERSE PRIMER:
                                      (SEQ ID NO: 93)
5'-AACAAGCTTAACCCGUAGAUCCGAUCUUGUGACTAGTGTT-3'

>hsa-miR-100-5p MIMAT0000098
                                      (SEQ ID NO: 94)
5'-AAC CCG UAG AUC CGA ACU UGUG-3'

(SEQ ID NO: 95)
CACA AGT TCG GAT CTA CGG GTT

100 FORWARD PRIMER:
                                      (SEQ ID NO: 96)
5'-AACACTAGTCACAAGTTCGGATCTACGGGTTAAGCTTGTT-3'

100 REVERSE PRIMER:
                                      (SEQ ID NO: 97)
5'-AACAAGCTTAACCCGUAGAUCCGAACUUGUGACTAGTGTT-3'

>hsa-let-7a-5p MIMAT0000062
                                      (SEQ ID NO: 98)
5'-UGA GGU AGU AGG UUG UAU AGUU-3'

(SEQ ID NO: 99)
AACT ATA CAA CCT ACT ACC TCA
```

-continued

LET7A FORWARD PRIMER:
(SEQ ID NO: 100)
5'-AACACTAGTAACTATACAACCTACTACCTCAAAGCTTGTT-3'

LET7A REVERSE PRIMER:
(SEQ ID NO: 101)
5'-AACAAGCTTGAGGUAGUAGGUUGUAUAGUUACTAGTGTT-3'

>hsa-let-7c-5p MIMAT0000064
(SEQ ID NO: 102)
5'-UGA GGU AGU AGG UUG UAU GGUU-3'

(SEQ ID NO: 103)
AACC ATA CAA CCT ACT ACC TCA

LET7C FORWARD PRIMER:
(SEQ ID NO: 104)
5'-AACACTAGTAACCATACAACCTACTACCTCAAAGCTTGTT-3'

LET7C REVERSE PRIMER:
(SEQ ID NO: 105)
5'-AACAAGCTTGAGGUAGUAGGEUGUAUGGUEACTAGTGTT-3'

The vector contains the following ordered elements: 5'-luciferase-Multiple Cloning Site (MCS) allowing for inserting nucleotide sequences corresponding to desired miRNA binding sites into its 3'UTR. The MCS contains the following ordered restriction sites: 5'-SpeI-HindIII. The SpeI (ACTAGT) and HindIII (AAGCTT) were selected as the restriction enzymes because they both function well in the same buffer (NEB2). The oligonucleotides contains the following ordered elements: 5'-AAC-SpeI site-(miRNA binding site)-HindIII site-GTT-3'. The nucleotides AAC (and GTT) are extra nucleotides allowing restriction enzymes to bind more effectively.

The nucleotide sequences for the pMIR-REPORT™ Luciferase vectors for miR-99, miR-100, Let-7a-5p and Let-7c-5p (LUC1, LUC2, LUC3, and LUC4 respectively) are set forth in SEQ ID NOs: 106-109 of the Sequence Listing.

HELA TRANSFECTION: Hela cells were cultured in Minimum Essential Media with Earle's Balanced Salt Solution (HyClone™) supplemented with 2 mM L-glutamine, 1 mM sodium pyruvate, 1 nM Non-essential Amino Acids, and 10% FBS (PAA) and penicillin streptomycin. The cells were plated in serum-containing media without antibiotics in 96-well plates ($1 \times 10^4$ cells/well) 24 hours prior to transfection and were at a confluency of between 30-70% at the time of transfection.

Cells were then transfected with 50 ng/well of the LUC reporter plasmid and 10 ng/well of the n-gal reporter plasmid for 2 hours with 0.1, 1, 10 or 50 nanomol/L (nM) using Lipofectamine 2000 (Life Technologies, Cat #11668-019) according to the manufacturer's instructions using Opti-MEM® Medium and normal growth medium in a final volume of 200 µl/well. Reporter plasmids (pMIR-REPORT™ or LUC plasmid) were transfected alone.

A typical plate setup for Hela cells in 2×96 wells is shown below, where column 6 of each plate identifies the LUC vector used for transfection.

TABLE 12

| Plate 1 with Luciferase Reporter 1 miR-99 (LUC 1) and Luciferase Reporter 2 miR-100 (LUC2) | | | | | | | | | | | | |
|---|---|---|---|---|---|---|---|---|---|---|---|---|
| JRX0- | | 1 | 2 | 3 | 4 | 5 | 6 | 7 | 8 | 9 | 10 | 11 | 12 |
| 0.1 n | A | 111 | 112 | 114 | 116 | 118 | LUC 1 | 111 | 112 | 114 | 116 | 118 | Lipo |
| 1 | B | 111 | 112 | 114 | 116 | 118 | LUC 1 | 111 | 112 | 114 | 116 | 118 | Lipo |
| 10 | C | 111 | 112 | 114 | 116 | 118 | LUC 1 | 111 | 112 | 114 | 116 | 118 | Lipo |
| 50 | D | 111 | 112 | 114 | 116 | 118 | LUC 1 | 111 | 112 | 114 | 116 | 118 | Lipo |
| 0.1 nM | E | 110 | 113 | 115 | 117 | 119 | LUC 2 | 110 | 113 | 115 | 117 | 119 | pMIR |
| 1 | F | 110 | 113 | 115 | 117 | 119 | LUC 2 | 110 | 113 | 115 | 117 | 119 | pMIR |
| 10 | G | 110 | 113 | 115 | 117 | 119 | LUC 2 | 110 | 113 | 115 | 117 | 119 | pMIR |
| 50 | H | 110 | 113 | 115 | 117 | 119 | LUC 2 | 110 | 113 | 115 | 117 | 119 | pMIR |

TABLE 13

| Plate 2 with Luciferase Reporter 3 Let-7a-5p (LUC 3) and Luciferase Reporter 4 Let-7c-5p (LUC4) | | | | | | | | | | | | |
|---|---|---|---|---|---|---|---|---|---|---|---|---|
| JRX0- | 1 | 2 | 3 | 4 | 5 | 6 | 7 | 8 | 9 | 10 | 11 | 12 |
| 0.1 nM A | 101 | 103 | 104 (10 nM) | 105 (10 nM) | 106 (10 nM) | LUC 3 | 107 (10 nM) | 108 (10 nM) | 109 (10 nM) | 101 | 103 | Lipo |
| 1 B | 101 | 103 | 104 (10 nM) | 105 (10 nM) | 106 (10 nM) | LUC 3 | 107 (10 nM) | 108 (10 nM) | 109 (10 nM) | 101 | 103 | Lipo |
| 10 C | 101 | 103 | 104 (50 nM) | 105 (50 nM) | 106 (50 nM) | LUC 3 | 107 (50 nM) | 108 (50 nM) | 109 (50 nM) | 101 | 103 | Lipo |
| 5 D | 101 | 103 | 104 (50 nM) | 105 (50 nM) | 106 (50 nM) | LUC 3 | 107 (50 nM) | 108 (50 nM) | 109 (50 nM) | 101 | 103 | Lipo |
| 0.1 nM E | 100 | 102 | 104 (10 nM) | 105 (10 nM) | 106 (10 nM) | LUC 4 | 107 (10 nM) | 108 (10 nM) | 109 (10 nM) | 100 | 102 | pMIR |
| 1 F | 100 | 102 | 104 (10 nM) | 105 (10 nM) | 106 (10 nM) | LUC 4 | 107 (10 nM) | 108 (10 nM) | 109 (10 nM) | 100 | 102 | pMIR |
| 10 G | 100 | 102 | 104 (50 nM) | 105 (50 nM) | 106 (50 nM) | LUC 4 | 107 (50 nM) | 108 (50 nM) | 109 (50 nM) | 100 | 102 | pMIR |
| 50 H | 100 | 102 | 104 (50 nM) | 105 (50 nM) | 106 (50 nM) | LUC 4 | 107 (50 nM) | 108 (50 nM) | 109 (50 nM) | 100 | 102 | pMIR |

CARDIAC MYOCYTE TRANSFECTION: neonatal rat cardiomyocytes were isolated and plated on Primaria™ coated plates at density of 80,000 cells per well (24 well). Twenty-four hours after plating the cells were transfected with 500 ng/well of the LUC reporter plasmid and 100 ng/well of the β-gal reporter plasmid for 5 hours with 0.1, 1, 3, 10 or 50 nanomol/L (nM) using Lipofectamine® 2000 (Life Technologies, Cat #11668-019) according to the manufacturer's instructions using Opti-MEM® Medium and normal growth medium in a final volume of 600 μl/well. Reporter plasmids (pMIR-REPORT™ or LUC plasmid) were transfected alone.

A typical plate setup for cardiac myocytes was as follows:

| Plate 1 Luciferase Reporter 1 (LUC1) miR-99 | | | | | | |
|---|---|---|---|---|---|---|
| 0 nM | LUC 1 | LUC 1 | 114 (3 nM) | 116 (3 nM) | LUC 1 (3 nM) | Lipo |
| 0.1 nM | JRX0111 | JRX0112 | JRX0114 | JRX0116 | JRX0118 | Lipo |
| 10 nM | JRX0111 | JRX0112 | JRX0114 | JRX0116 | JRX0118 | pMIR |
| 50 nM | JRX0111 | JRX0112 | JRX0114 | JRX0116 | JRX0118 | pMIR |

| Plate 2 Luciferase Reporter 2 (LUC 2) miR-100 | | | | | | |
|---|---|---|---|---|---|---|
| 0 nM | LUC 2 | LUC 2 | JRX0115 (3 nM) | JRX0117(3 nM) | JRX0119(3 nM) | Lipo |
| 0.1 nM | JRX0110 | JRX0113 | JRX0115 | JRX0117 | JRX0119 | Lipo |
| 10 nM | JRX0110 | JRX0113 | JRX0115 | JRX0117 | JRX0119 | pMIR |
| 50 nM | JRX0110 | JRX0113 | JRX0115 | JRX0117 | JRX0119 | pMIR |

| Plate 3 Luciferase Reporter 3 (LUC 3) let-7a | | | | | | |
|---|---|---|---|---|---|---|
| 0 nM | LUC 3 | LUC 3 | 104(3 nm) | 106(3 nM) | 108(3 nM) | Lipo |
| 0.1 nM | JRX0101 | 103 | 104(10 nm) | 106(10 nm) | 108(10 nM) | Lipo |
| 10 nM | JRX0101 | 103 | 105(3 nm) | 107(3 nM) | 109(3 nM) | pMIR |
| 50 nM | JRX0101 | 103 | 105(10 nm) | 107(10 nM) | 109(10 nM) | pMIR |

| Plate 4 Luciferase Reporter 4 (LUC 4) let07c | | | | | | |
|---|---|---|---|---|---|---|
| 0 nM | LUC 4 | LUC 4 | JRX0104(3 nm) | JRX0106(3 nM) | JRX0108(3 nM) | Lipo |
| 0.1 nM | JRX0100 | JRX0102 | JRX0104(10 nm) | JRX0106(10 nm) | JRX0108(10 nM) | Lipo |
| 10 nM | JRX0100 | JRX0102 | JRX0105(3 nm) | JRX0107(10 nM) | JRX0109(3 nM) | pMIR |
| 50 nM | JRX0100 | JRX0102 | JRX0105(10 nm) | JRX0107(10 nM) | JRX0109(10 nM) | pMIR |

The above experiments were repeated.

Promoter Activity Assay

Cells were grown at 37° C. and harvested 48 hours post transfection for luciferase and β-gal assays in normal growth media using ONE-Glo™ Luc (Promega™ #E6110), Beta-Glo® Luc (Promega™ #E4720) and Glo Lysis Buffer (Promega™ #E2661). Luciferase activity was measured using the BioTek Synergy™ HT. Promoter activity was expressed as Fold over the Luciferase 1, 2, 3 or 4 plasmid alone and was normalized to β-gal activity levels.

Statistical Analysis

Luciferase activity was normalized to β-gal and the data were expressed as fold activation of the respective LUC vector alone. The fold data for the Hela experiments represent a single experiment. The experiments were repeated to confirm the results. The fold date from the two separate cardiac myocyte experiments were combined since the cells were cultured and transfected on the same day. The data are presented at Mean Standard Deviation. Graphs were drawn using GraphPad Prism 7 software with the normalized fold increase in luciferase activity (x-axis) against the log-10 M concentration of anti-miR (y-axis).

Results

Figure 5:
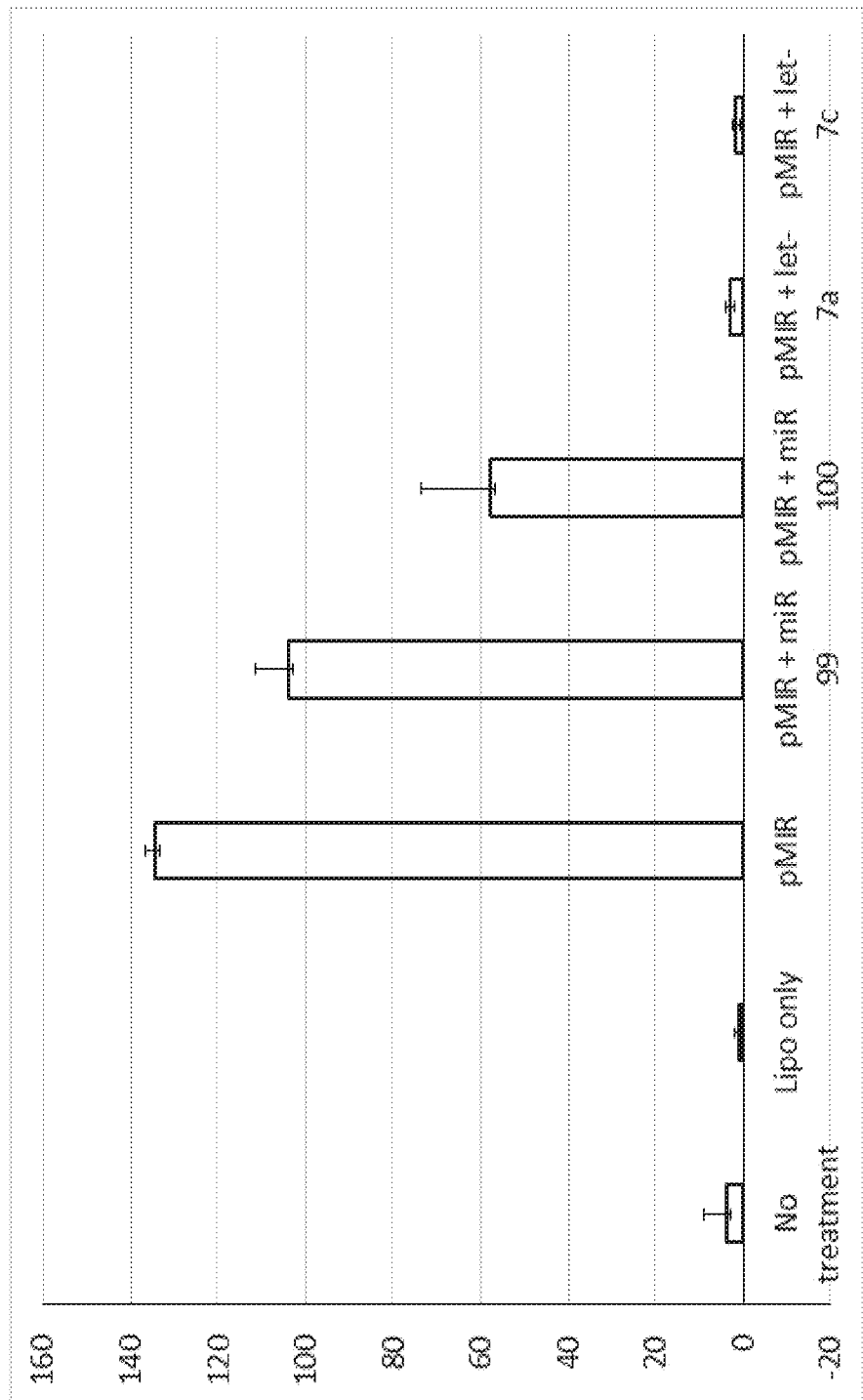
FIG. 5 is a schematic summary of the results of experiments performed in Hela cells, demonstrating that the endogenous miRs (Let-7a-5p miR-99a, miR-100-5p, miR-Let-7c5p, miR-Let-7a-5p) within Hela cells can bind to the respective LUC reporter constructs described in Example 5 below, and repress luciferase activity.

A test experiment on the Luciferase constructs was conducted to confirm that Luciferase Construct 1 (LUC 1, miR-99), Luciferase Construct 2 (LUC 2, miR-100), Luciferase Construct 3 (LUC 3, let-7a), and Luciferase Construct 4 (LUC 4, let-7c), had significantly less luciferase activity compared to the unmodified pMIR-REPORT Vector, suggesting that the endogenous miRs (Let-7a-5p miR-99a, miR-100-5p, miR-Let-7c5p, miR-Let-7a-5p) within Hela cells can bind to the respective LUC construct and repress luciferase activity. In this experiment, Hela cells were transfected with each of the LUC constructs and then treated with the corresponding anti-miRs. It was contemplated that the anti-miRs would compete with their corresponding endogenous microRNA in Hela cells. The unmodified pMIR-REPORT™ were observed to provide maximal luciferase activity when transfected in to Hela cells or rat neonatal ventricular cardiac myocytes. By inserting the predicted miRNA target sequences in the multiple cloning site for miR-99 (Luciferase reporter 1, LUC 1), miR-100 (Luciferase reporter 2, LUC 2) and Let-7a-5p (Luciferase reporter 3, LUC 3) and Let-7c-5p (Luciferase reporter 4, LUC 4), luciferase activity was significantly less than the pMIR-REPORT™ alone. The modified pMIR-REPORT LUC 1, LUC 2, LUC 3 and LUC 4 Luciferase miRNA Expression Reporter Vectors can be used to conduct accurate, quantitative evaluations of miRNA function, such that inhibition of endogenous miR members in HeLa cells and cardiac myocytes would lead to a dose-dependent increase in luciferase activity compared to the LUC 1, LUC 2, LUC 3 and LUC 4 vectors alone. Without being bound to any particular theory, it was believed anti-miRs act via steric blockade of a specific microRNA in the RISC complex and increase the corresponding Luciferase promoter activity. The result of this test experiment is schematically summarized in FIG. 5.

Figure 6:
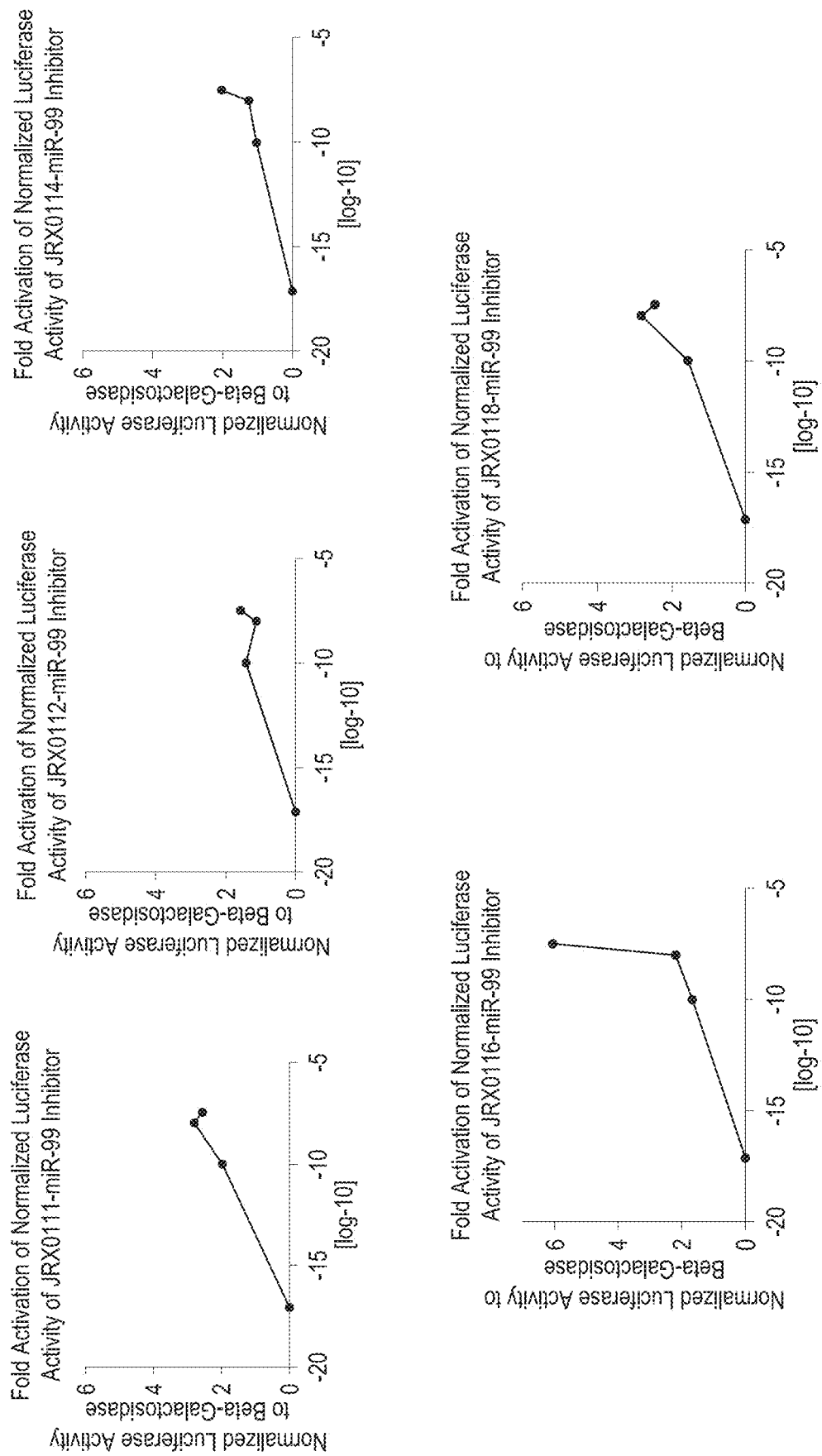
FIG. 6 is a schematic summary of the results of experiments performed in Hela cells, illustrating that JRX0111, JRX0112, JRX0114, JRX0116, JRX0118 miR-99a (miR-99) anti-miRs were found to increase Luciferase Construct 1 (LUC 1, miR-99a) activity in a dose-dependent manner (Log-10 M) which contained a miR binding sequence complementary to miR-99a cloned into the multiple cloning site of pMIR-REPORT™ Luciferase (pMIR).

In a subsequent experiment performed with Hela cells, it was observed that JRX0111, JRX0112, JRX0114, JRX0116, JRX0118 miR-99a anti-miRs increased Luciferase Construct 1 (LUC 1, miR-99) activity in a dose-dependent manner (FIG. 6).

Figure 7:
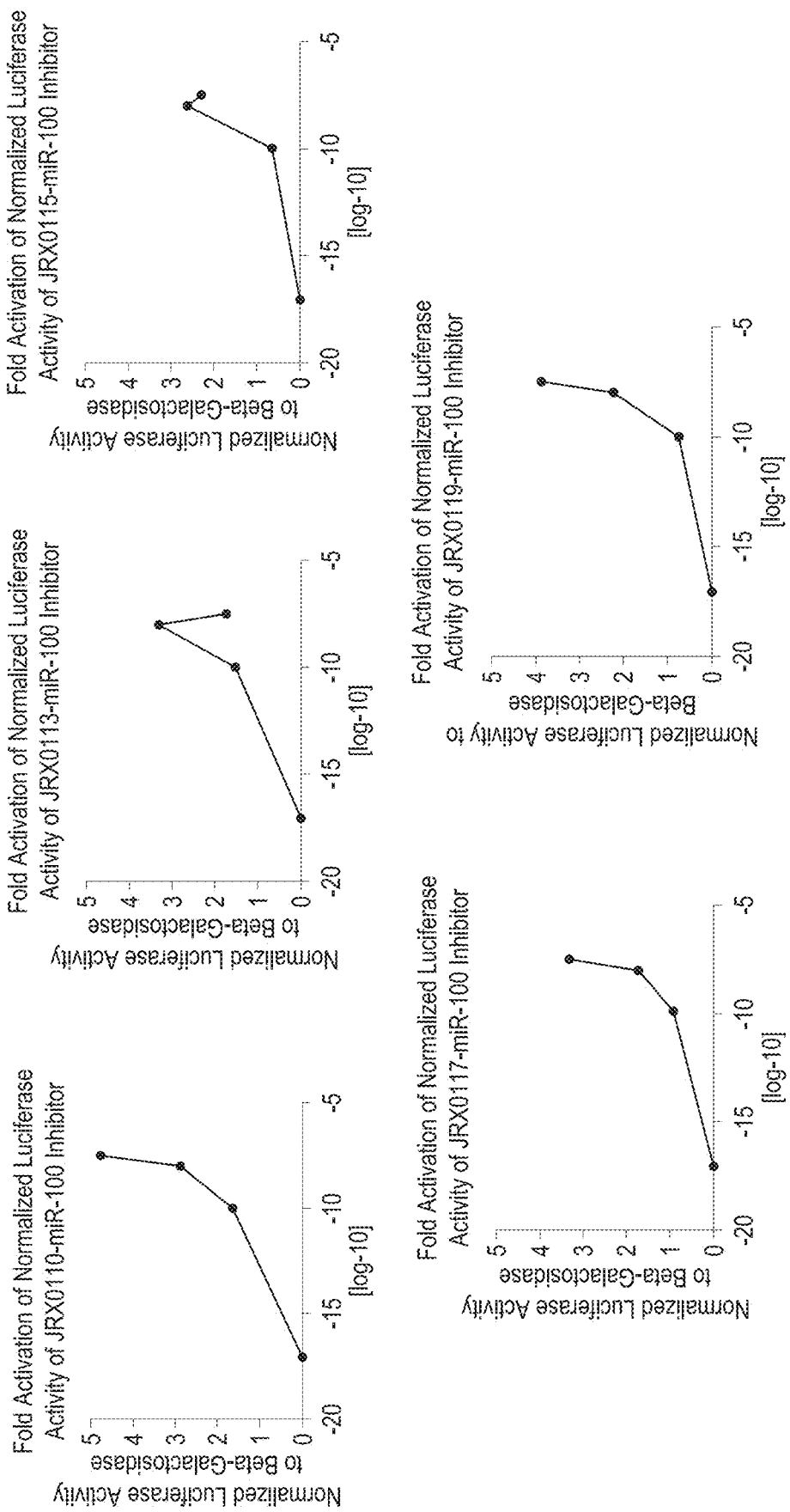
FIG. 7 is a schematic summary of the results of experiments performed in Hela cells, demonstrating that JRX0110, JRX0113, JRX0115, JRX0117, JRX0119 miR-100-5p anti-miRs were observed to increase Luciferase Construct 2 (LUC 2, miR-100-5p) activity in a dose-dependent manner (Log-10 M) which contained a miR binding sequence complementary to miR-100-5p cloned into the multiple cloning site of pMIR-REPORT™ Luciferase (pMIR).

In a similar manner, as shown in FIG. 7, JRX0110, JRX0113, JRX0115, JRX0117, JRX0119 miR-100-5p anti-miRs were observed to increase Luciferase Construct 2 (LUC 2, miR-100) activity in Hela cells in a dose-dependent manner.

Figure 8A:
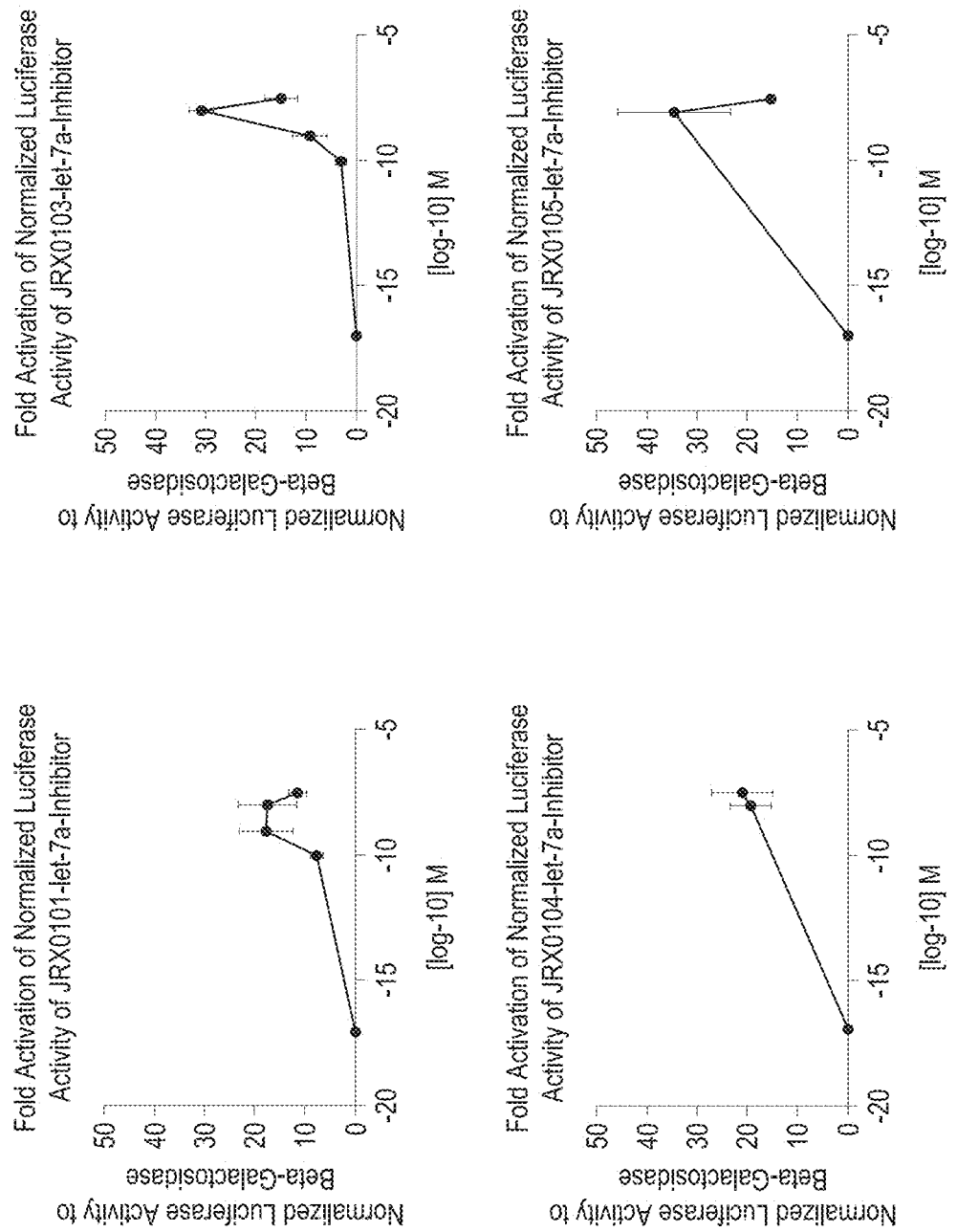
FIGS. 8A-8B schematically summarize the results of experiments performed in Hela cells, demonstrating that JRX0101, JRX0103, JRX0104, JRX0105, JRX0106, JRX0107, JRX0108, JRX0109 Let-7a-5p miR-Let-7a-5p anti-miRs were found to increase Luciferase Construct 3 (LUC 3, let-7a) activity in a dose-dependent manner (Log-10 M). LUC 3 contained a miR binding sequence complementary to miR-Let-7a-5p cloned into the multiple cloning site of pMIR-REPORT™ Luciferase (pMIR).
Figure 8B:
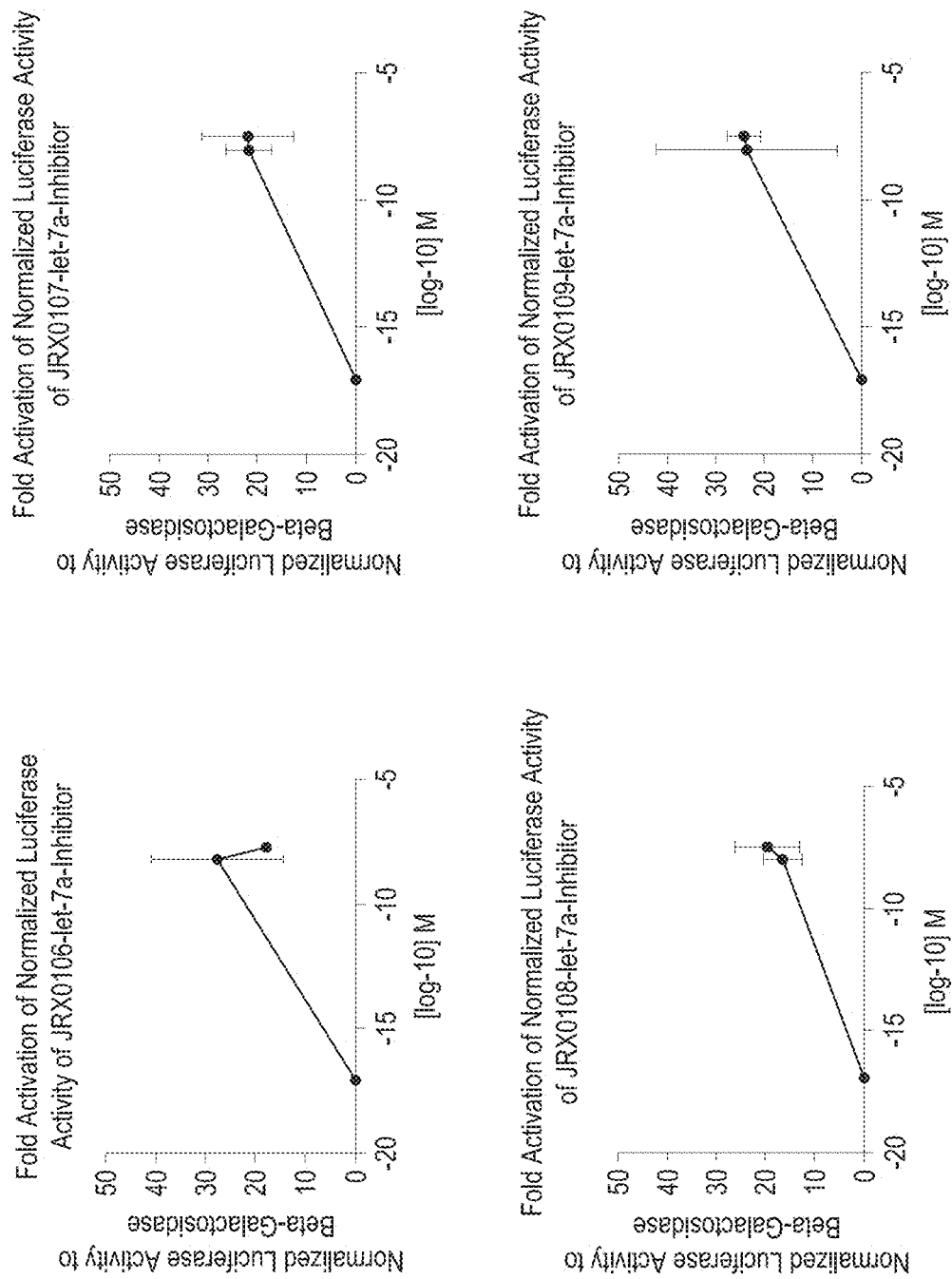
Figure 9A:
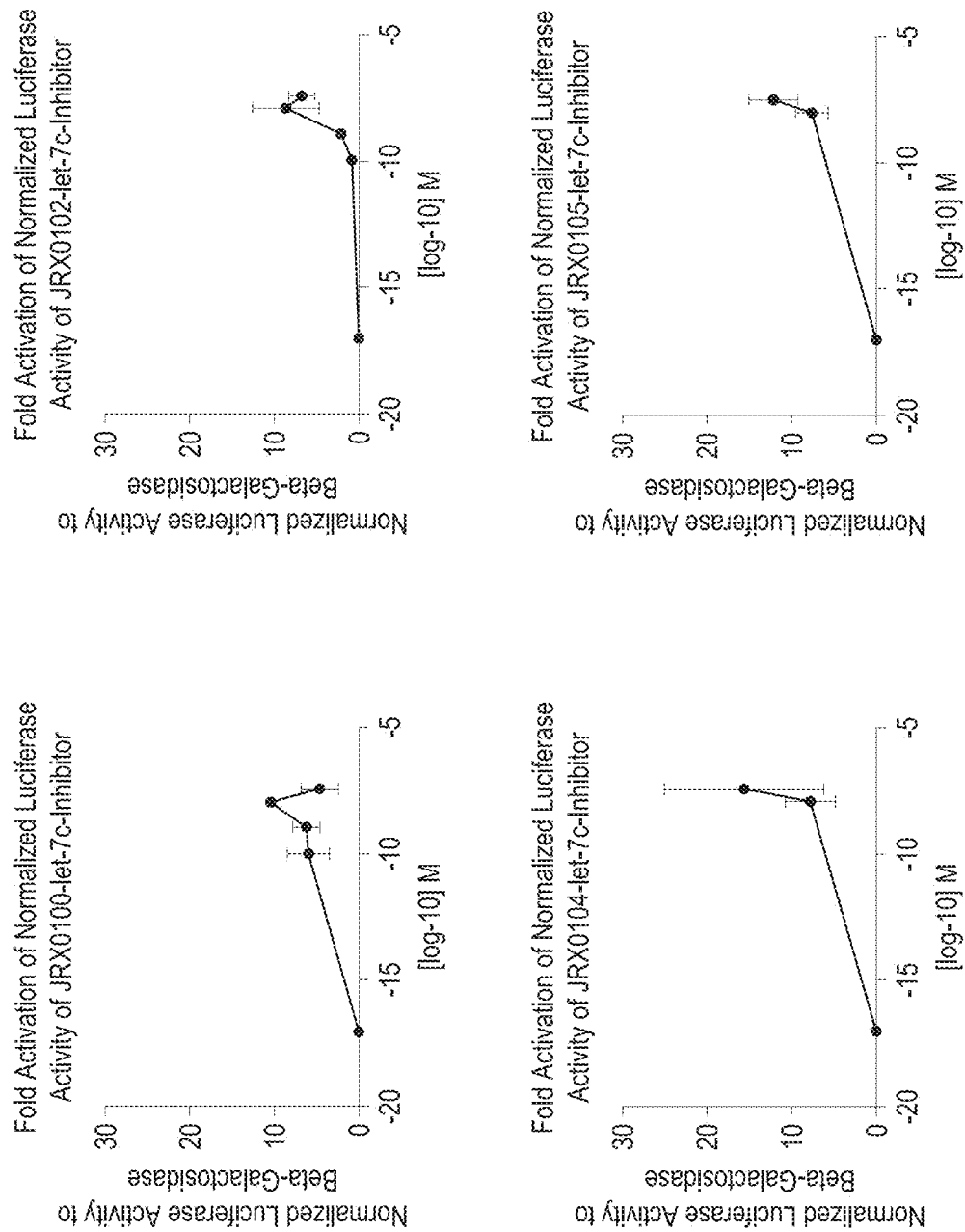
FIGS. 9A-9B schematically summarize of the results of experiments performed in Hela cells, demonstrating that JRX0100, JRX0102, JRX0104, JRX0105, JRX0106, JRX0107, JRX0108, JRX0109 Let-7c-5p miR-Let-7c5p anti-miRs were observed to increase Luciferase Construct 4 (LUC 4, let-7c) activity in a dose-dependent manner (Log-10 M). LUC 4 contained a miR binding sequence complementary to miR-Let-7c5p cloned into the multiple cloning site of pMIR-REPORT™ Luciferase (pMIR).
Figure 9B:
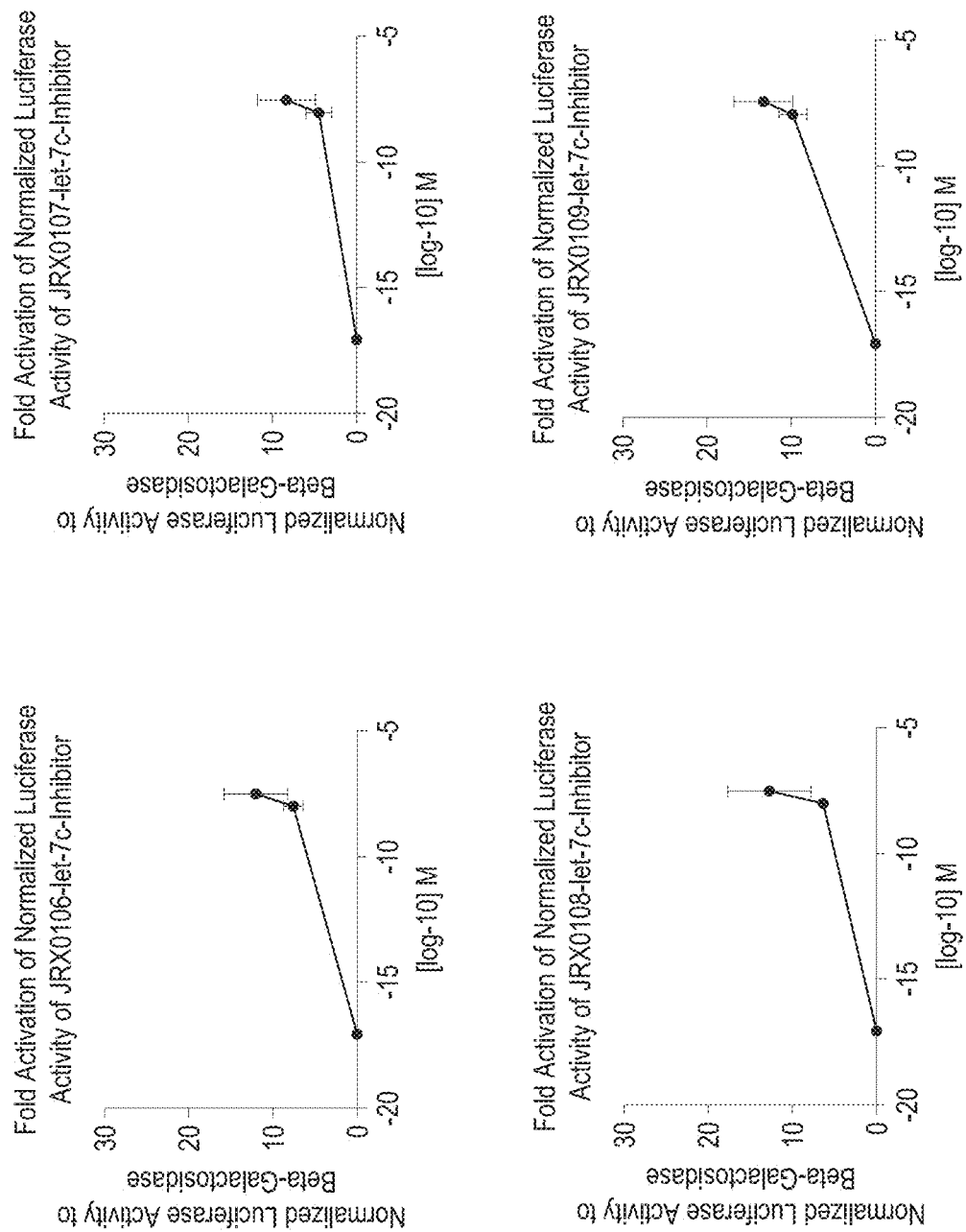

Similarly, JRX0101, JRX0103, JRX0104, JRX0105, JRX0106, JRX0107, JRX0108, JRX0109 Let-7a-5p miR- Let-7a-5p anti-miRs were also found to increase Luciferase Construct 3 (LUC 3, let-7a) activity in Hela cells in a dose-dependent manner (FIGS. 8A-8B); and JRX0100, JRX0102, JRX0104, JRX0105, JRX0106, JRX0107, JRX0108, JRX0109 Let-7c-5p miR-Let-7c5p anti-miRs were observed to increase Luciferase Construct 4 (LUC 4, let-7c) activity in Hela cells in a dose-dependent manner (FIGS. 9A-9B).

Figure 10:
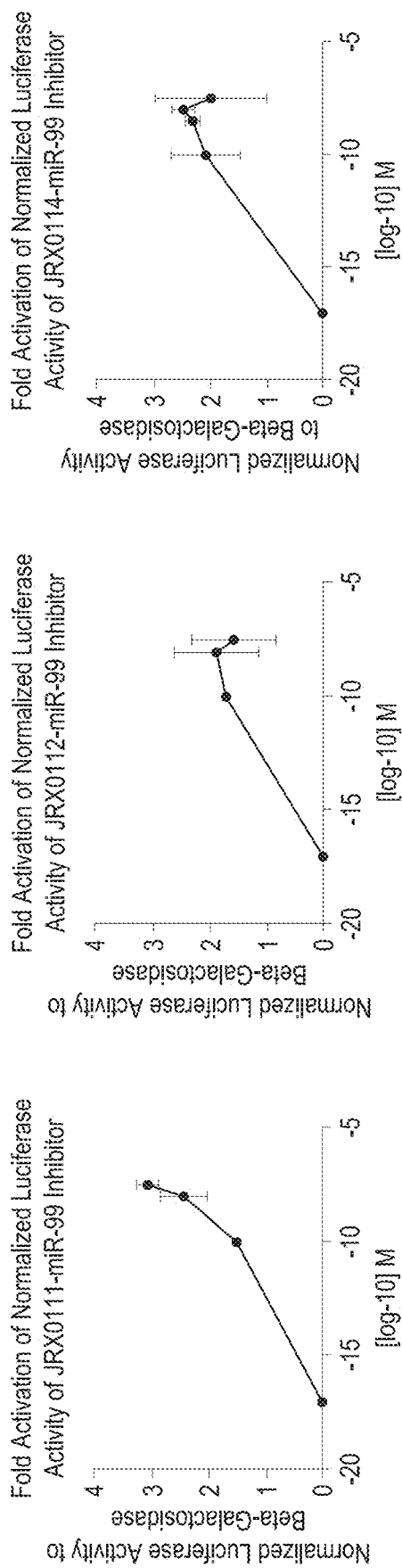
FIG. 10 is a schematic summary of the results of experiments performed in neonatal rat ventricular cardiac myocytes, demonstrating that experimental results demonstrating that JRX0111, JRX0112, JRX0114, JRX0116, JRX0118 miR-99a anti-miRs were observed to increase Luciferase Construct 1 (LUC 1, miR-99) activity in a dose-dependent manner (Log-10 M).
Figure 10:
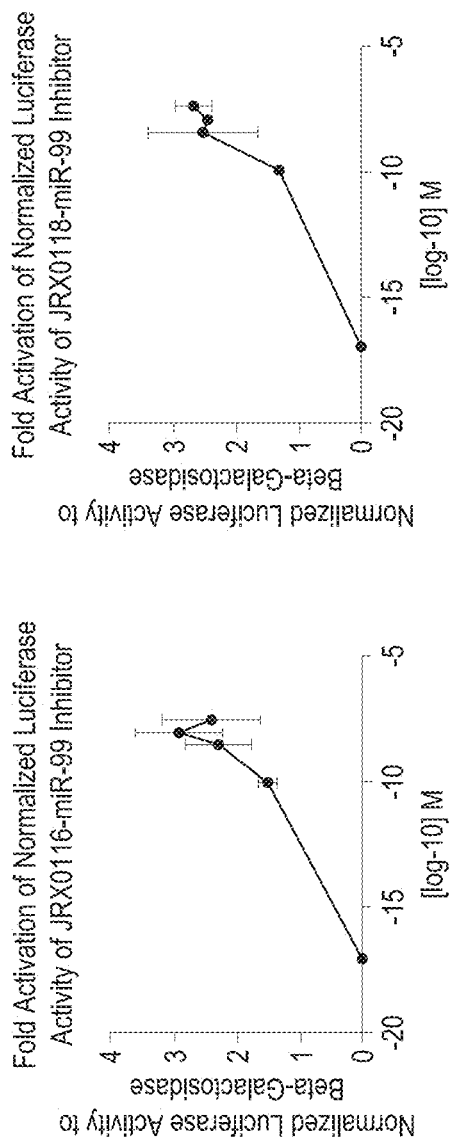
Figure 11:
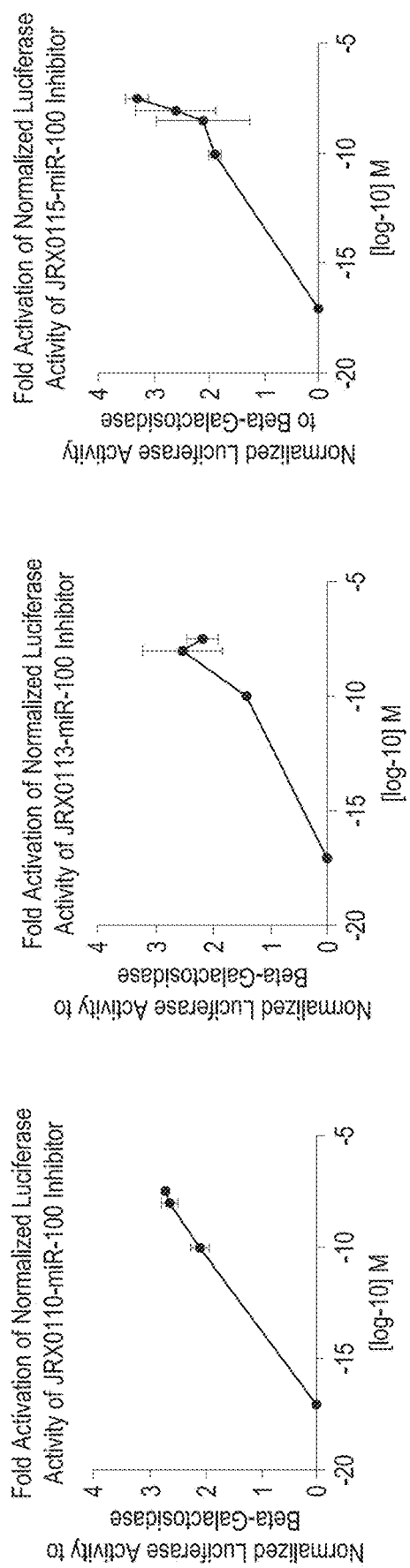
FIG. 11 is a schematic summary of the results of experiments performed in neonatal rat ventricular cardiac myocytes, demonstrating that JRX0110, JRX0113, JRX0115, JRX0117, JRX0119 miR-100-5p anti-miRs were observed to increase Luciferase Construct 2 (LUC 2, miR-100) activity in a dose-dependent manner (Log-10 M).
Figure 11:
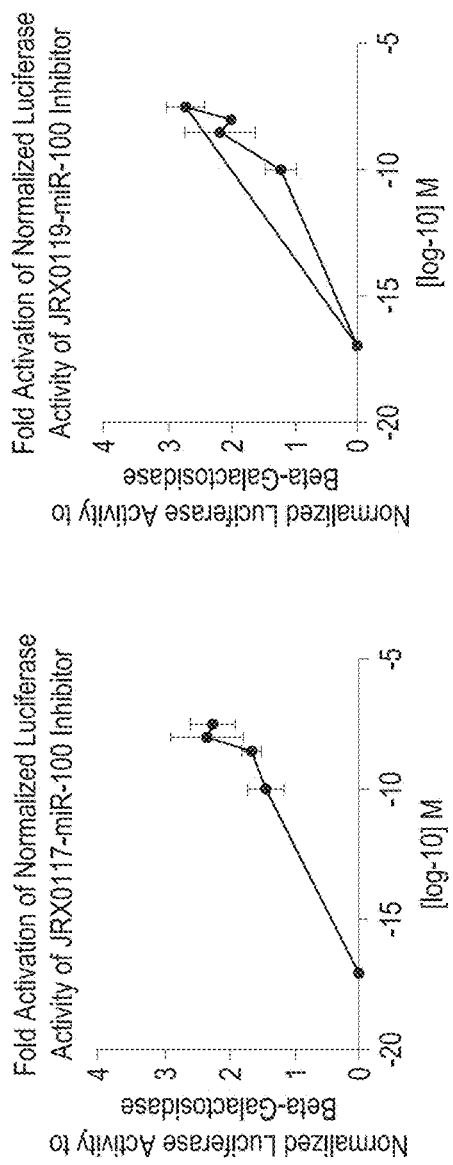
Figure 12A:
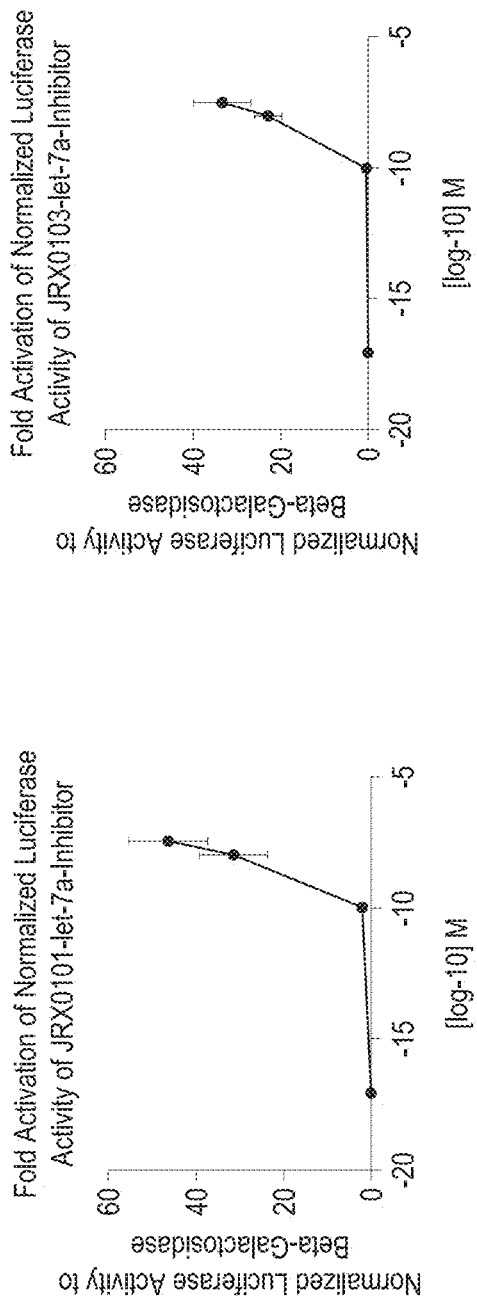
FIGS. 12A-12B schematically summarize the results of experiments performed in neonatal rat ventricular cardiac myocytes, demonstrating that JRX0101, JRX0103, JRX0104, JRX0105, JRX0106, JRX0107, JRX0108, JRX0109 Let-7a-5p miR-Let-7a-5p anti-miRs were found to increase Luciferase Construct 3 (LUC 3, let-7a) activity in a dose-dependent manner (Log-10 M).
Figure 12A:
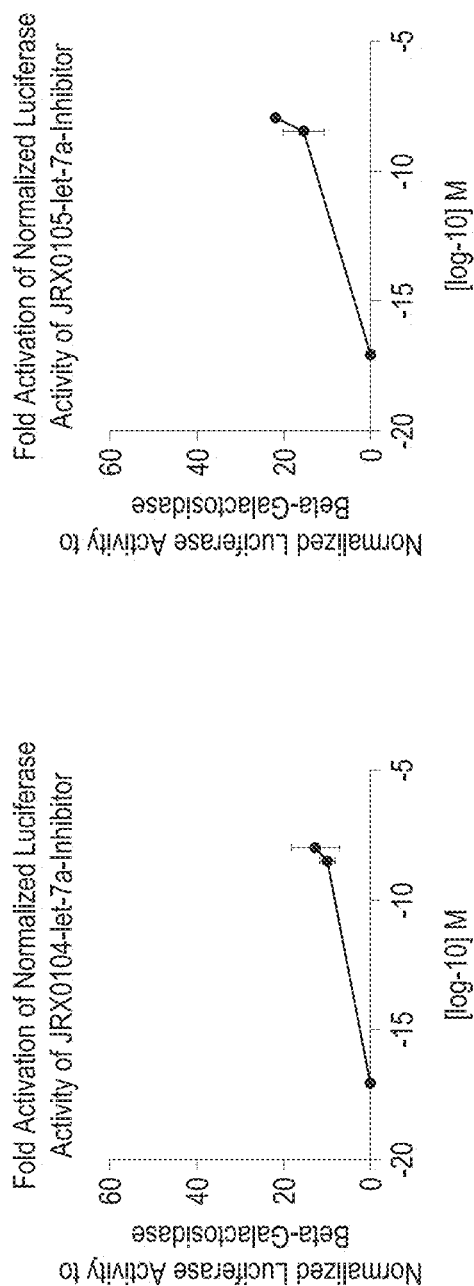
Figure 12B:
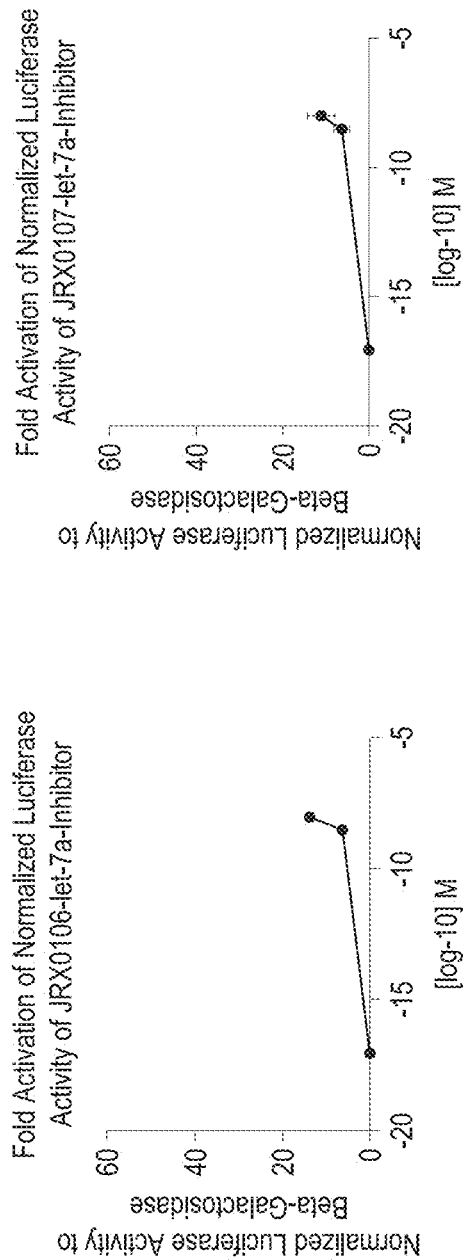
Figure 12B:
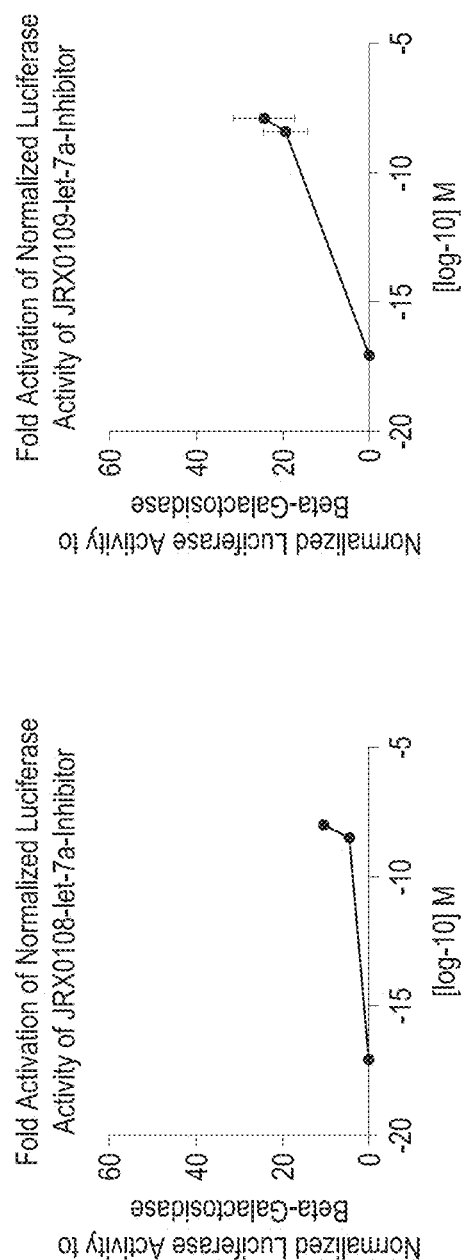
Figure 13A:
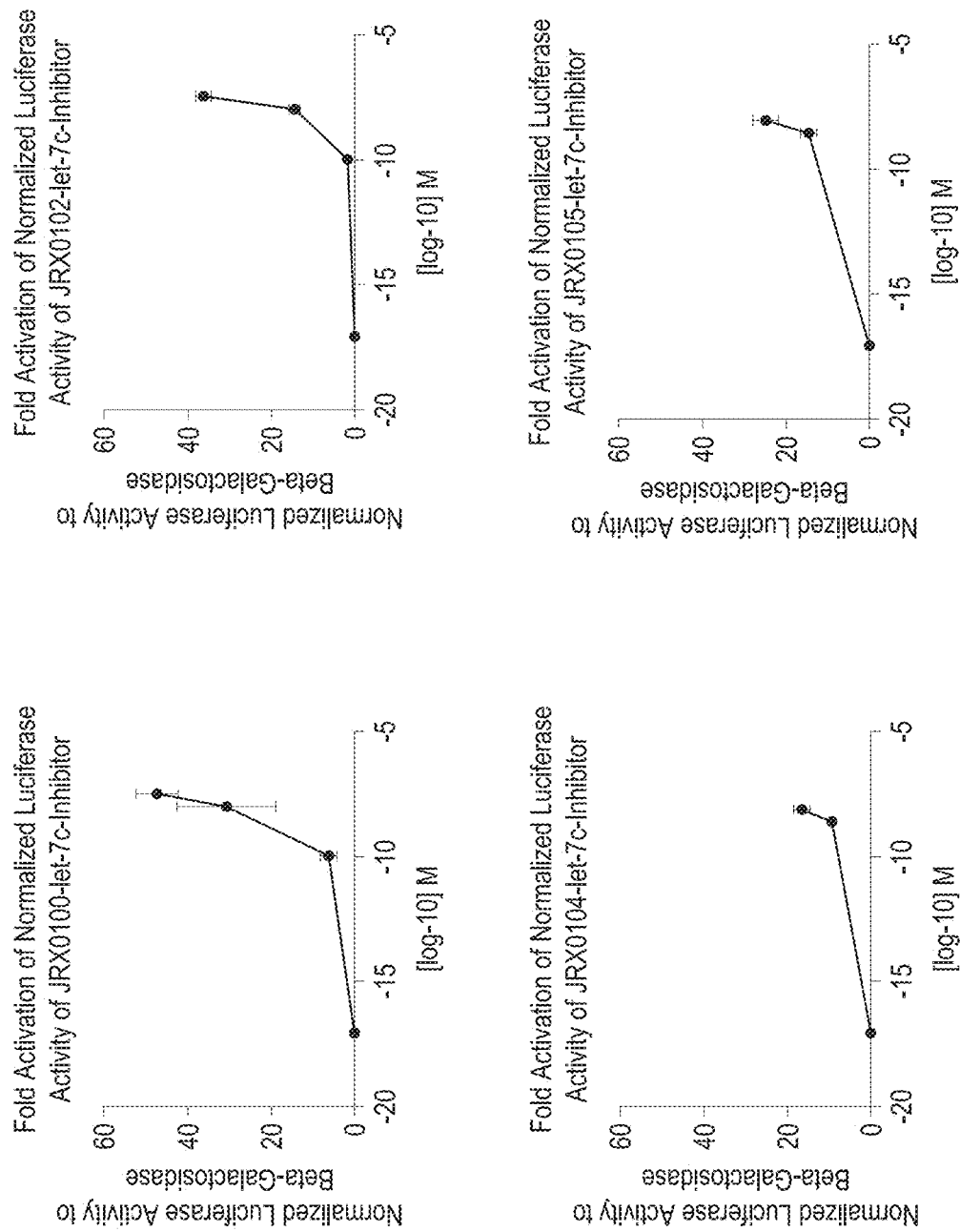
FIGS. 13A-13B schematically summarize the results of experiments performed in neonatal rat ventricular cardiac myocytes, demonstrating that JRX0100, JRX0102, JRX0104, JRX0105, JRX0106, JRX0107, JRX0108, JRX0109 Let-7c-5p miR-Let-7c5p anti-miRs were observed to increase Luciferase Construct 4 (LUC 4, let-7c) activity in a dose-dependent manner (Log-10 M).
Figure 13B:
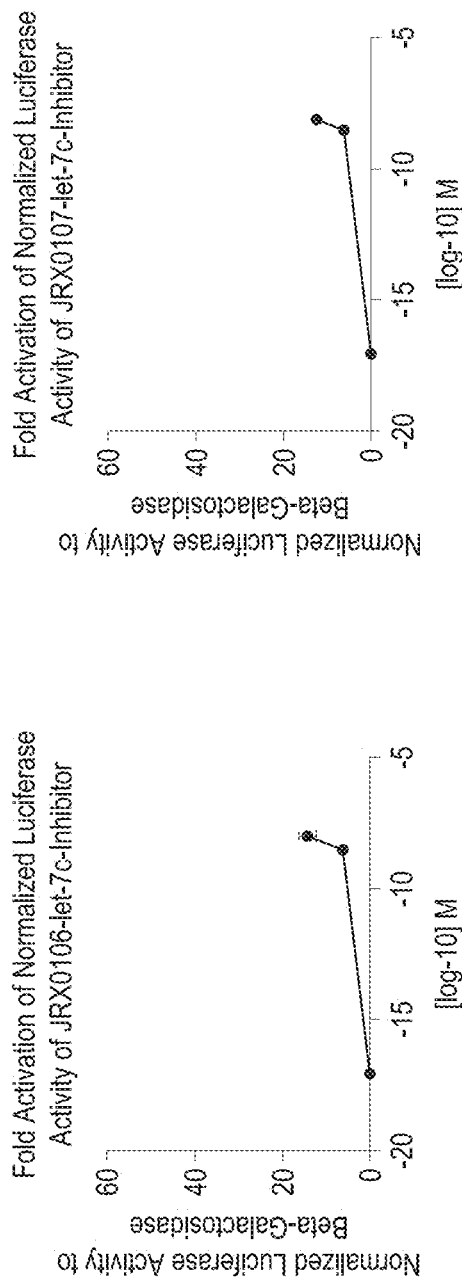
Figure 13B:
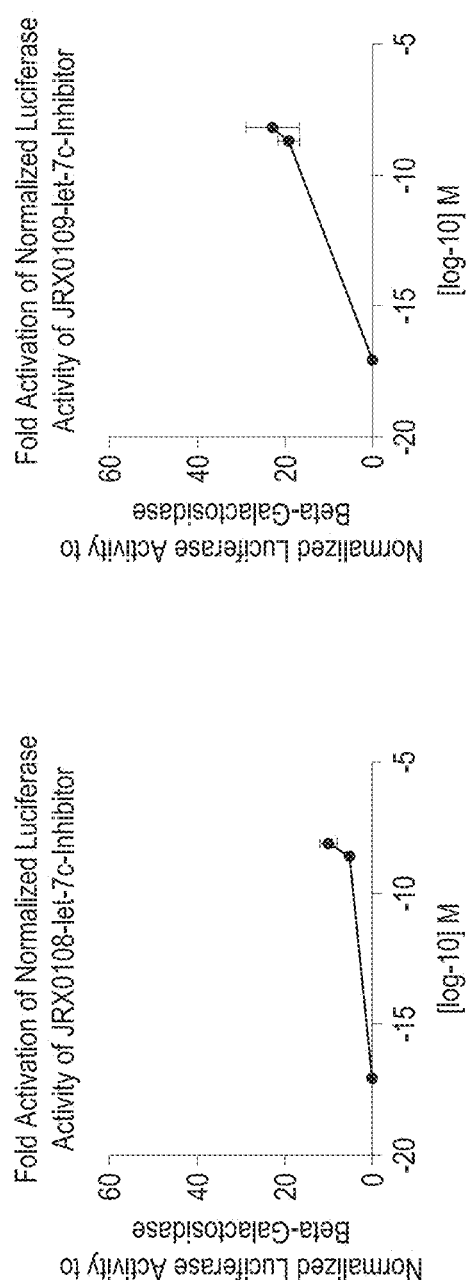

In various experiments performed with neonatal rat ventricular cardiac myocytes, JRX0111, JRX0112, JRX0114, JRX0116, JRX0118 miR-99a anti-miRs were observed to increase Luciferase Construct 1 (LUC 1, miR-99) activity in a dose-dependent manner (FIG. 10); JRX0110, JRX0113, JRX0115, JRX0117, JRX0119 miR-100-5p anti-miRs were observed to increase Luciferase Construct 2 (LUC 2, miR-100) activity in a dose-dependent manner (FIG. 11); JRX0101, JRX0103, JRX0104, JRX0105, JRX0106, JRX0107, JRX0108, JRX0109 Let-7a-5p miR-Let-7a-5p anti-miRs were observed to increase Luciferase Construct 3 (LUC 3, let-7a) activity in a dose-dependent manner (FIGS. 12A-12B) and JRX0100, JRX0102, JRX0104, JRX0105, JRX0106, JRX0107, JRX0108, JRX0109 Let-7c-5p miR-Let-7c5p anti-miRs were also found to increase Luciferase Construct 4 (LUC 4, let-7c) activity in a dose-dependent manner (FIGS. 13A-13B).

CONCLUSION

Taken together, the experimental data presented above confirm the potency, specificity and activity of the specified anti-miRs. The modified plasmids LUC 1, LUC 2, LUC 3 and LUC 4 were found to exhibit significantly less luciferase activity compared to the pMIR-REPORT™ empty plasmid. It was further observed that each antagonist from the corresponding miR family dose dependently activated their respective LUC reporter plasmid. In addition, it appears that the anti-miRs designed to inhibit the following microRNAs miR-99, miR-100, Let-7a-5p, and Let-7c-5p bound to their specific target mRNA with varying efficiency in both cell types tested.

All of the references disclosed herein, including but not limited to journal articles, textbooks, patents and patent applications, are hereby incorporated by reference for the subject matter discussed herein and in their entireties. Throughout this disclosure, various information sources are referred to and incorporated by reference. The information sources include, for example, scientific journal articles, patent documents, textbooks, and World Wide Web browser-inactive page addresses. The reference to such information sources is solely for the purpose of providing an indication of the general state of the art at the time of filing. While the contents and teachings of each and every one of the information sources can be relied on and used by one of skill in the art to make and use the embodiments disclosed herein, any discussion and comment in a specific information source should no way be considered as an admission that such comment was widely accepted as the general opinion in the field.

What is claimed is:

1. A composition, comprising:
(a) at least one miR-99a-5p antagonist comprising a chemically modified nucleotide sequence selected from the group consisting of:
SEQ ID NO: 47 wherein nucleotides 1, 2, 6, 10, 13, 14 and 17-19 of SEQ ID NO: 47 are locked nucleic acids (LNAs),
SEQ ID NO: 48 wherein nucleotides 1, 2, 4, 8, 15, 17 and 18 of SEQ ID NO: 48 are LNAs,
SEQ ID NO: 50 wherein nucleotides 1, 2, 6, 9, 11, 13, 14, 16 and 17 of SEQ ID NO: 50 are LNAs,
SEQ ID NO: 52 wherein nucleotides 1, 2, 6, 10, 13, 15 and 16 of SEQ ID NO: 52 are LNAs, and
SEQ ID NO: 54 wherein nucleotides 1, 2, 6, 9, 11, 12, 14 and 15 of SEQ ID NO: 54 are LNAs;
(b) at least one miR-100-5p antagonist comprising a chemically modified nucleotide sequence selected from the group consisting of:
SEQ ID NO: 46 wherein nucleotides 1, 2, 5, 9, 13, 15 and 17-19 of SEQ ID NO: 46 are LNAs,
SEQ ID NO: 49 wherein nucleotides 1, 2, 6, 9, 13, 15, 17 and 18 of SEQ ID NO: 49 are LNAs,
SEQ ID NO: 51 wherein nucleotides 1, 2, 6, 11, 13 and 15-17 of SEQ ID NO: 51 are LNAs,
SEQ ID NO: 53 wherein nucleotides 1, 2, 6, 10 and 14-16 of SEQ ID NO: 53 are LNAs, and
SEQ ID NO: 55 wherein nucleotides 1, 2, 5, 9-11 and 13-15 of SEQ ID NO: 55 are LNAs;
(c) at least one miR-Let-7a-5p antagonist comprising a chemically modified nucleotide sequence selected from the group consisting of:
SEQ ID NO: 37 wherein nucleotides 1, 2, 6, 10, 13, 14, and 17-19 of SEQ ID NO: 37 are LNAs,
SEQ ID NO: 39 wherein nucleotides 1, 2, 6, 9, 13-15, 17 and 18 of SEQ ID NO: 39 are LNAs,
SEQ ID NO: 40 wherein nucleotides 1, 6, 9, 11, 13 and 17 of SEQ ID NO: 40 are LNAs,
SEQ ID NO: 41 wherein nucleotides 1, 2, 6, 8, 11, 13, and 15-17 of SEQ ID NO: 41 are LNAs,
SEQ ID NO: 42 wherein nucleotides 1, 2, 6, 10, 13, 15 and 16 of SEQ ID NO: 42 are LNAs,
SEQ ID NO: 43 wherein nucleotides 1, 2, 6, 10 and 14-16 of SEQ ID NO: 43 are LNAs,
SEQ ID NO: 44 wherein nucleotides 1, 2, 6, 9, 11 and 15 of SEQ ID NO: 44 are LNAs, and
SEQ ID NO: 45 wherein nucleotides 1, 2, 5, 9-11 and 13-15 of SEQ ID NO: 45 are LNAs; or
(d) at least one miR-Let-7c-5p antagonist comprising a chemically modified sequence selected from the group consisting of:
SEQ ID NO: 36 wherein nucleotides 1, 2, 5, 9, 13, 15, and 17-19 of SEQ ID NO: 36 are LNAs,
SEQ ID NO: 38 wherein nucleotides 1, 2, 7, 12, 14, 15, and 17 of SEQ ID NO: 38 are LNAs, SEQ ID NO: 40 wherein nucleotides 1, 6, 9, 11, 13 and 17 of SEQ ID NO: 40 are LNAs, SEQ ID NO: 41 wherein nucleotides 1, 2, 6, 8, 11, 13, and 15-17 of SEQ ID NO: 41 are LNAs, SEQ ID NO: 42 wherein nucleotides 1, 2, 6, 10, 13, 15 and 16 of SEQ ID NO: 42 are LNAs, SEQ ID NO: 43 wherein nucleotides 1, 2, 6, 10 and 14-16 of SEQ ID NO: 43 are LNAs, SEQ ID NO: 44 wherein nucleotides 1, 2, 6, 9, 11 and 15 of SEQ ID NO: 44 are LNAs, and SEQ ID NO: 45 wherein nucleotides 1, 2, 5, 9-11 and 13-15 of SEQ ID NO: 45 are LNAs;

wherein each of SEQ ID Nos: 36-55 comprises phosphorothioate internucleoside linkages.

2. The composition of claim 1, comprising:
(a) an miR-99a-5p antagonist comprising one of chemically modified nucleotide sequences of SEQ ID NOs: 47, 48, 50, 52, and 54;
(b) an miR-100-5p antagonist comprising one of chemically modified nucleotide sequences of SEQ ID Nos: 46, 49, 51, 53, and 55;
(c) a miR-Let-7a-5p antagonist comprising one of chemically modified nucleotide sequences of SEQ ID Nos: 37 and 39-45; and
(d) a miR-Let-7c-5p antagonist comprising one of chemically modified sequences of SEQ ID Nos: 36, 38, and 40-45.

3. A pharmaceutical composition, comprising:
a plurality of miR antagonists of claim 2; and
a pharmaceutically acceptable excipients, diluents, adjuvants, or stabilizers.

4. A method for promoting cardiac muscle regeneration or for treating a cardiac disease in a subject, comprising administering to a subject in need thereof a pharmaceutical composition of claim 3.

5. The method of claim 4, wherein the subject in need thereof is a human subject suffering from a cardiac disease.

6. The method of claim 5, wherein the cardiac disease is a congenital cardiac disease.

7. The method of claim 5, wherein the cardiac disease is selected from the group consisting of myocardial infarction, ischemic heart disease, dilated cardiomyopathy, heart failure, ischemic cardiomyopathy, hypertrophic cardiomyopathy, restrictive cardiomyopathy, alcoholic cardiomyopathy, viral cardiomyopathy, tachycardia-mediated cardiomyopathy, stress-induced cardiomyopathy, amyloid cardiomyopathy, arrhythmogenic right ventricular dysplasia, left ventricular noncompaction, endocardial fibroelastosis, aortic stenosis, aortic regurgitation, mitral stenosis, mitral regurgitation, mitral prolapse, pulmonary stenosis, pulmonary regurgitation, tricuspid stenosis, and tricuspid regurgitation.

8. The method of claim 4, further comprising administering to the subject in need thereof one or more additional therapeutic therapies or agents.

9. The method of claim 8, wherein at least one of the one or more additional therapeutic therapies or agents comprises Idebenone; Eplerenone; an electrical nerve stimulator; AVI-4658; Ataluren; BMN044/PRO044; CAT-1004; MicroDystrophin AAV Gene Therapy (SGT-001); Galectin-1 Therapy (SB-002); LTBB4 (SB-001); rAAV2.5-CMV-minidystrophin; Glutamine; NFKB inhibitors; Sarcoglycan, delta (35 kDa dystrophin-associated glycoprotein); insulin like growth factor-1 (IGF-1); and combinations thereof.

10. The method of claim 8, wherein the pharmaceutical composition and at least one of the one or more additional therapeutic therapies or agents are administered to the subject sequentially or in rotation.

11. A pharmaceutical composition, comprising:
a composition of claim 1; and
a pharmaceutically acceptable excipients, diluents, adjuvants, or stabilizers.

12. A method for promoting cardiac muscle regeneration or for treating a cardiac disease in a subject, comprising administering to a subject in need thereof a pharmaceutical composition of claim 11.

13. The method of claim 12, wherein the subject in need thereof is a human subject suffering from a cardiac disease.

14. The method of claim 13, wherein the cardiac disease is a congenital cardiac disease.

15. The method of claim 13, wherein the cardiac disease is selected from the group consisting of myocardial infarction, ischemic heart disease, dilated cardiomyopathy, heart failure, ischemic cardiomyopathy, hypertrophic cardiomyopathy, restrictive cardiomyopathy, alcoholic cardiomyopathy, viral cardiomyopathy, tachycardia-mediated cardiomyopathy, stress-induced cardiomyopathy, amyloid cardiomyopathy, arrhythmogenic right ventricular dysplasia, left ventricular noncompaction, endocardial fibroelastosis, aortic stenosis, aortic regurgitation, mitral stenosis, mitral regurgitation, mitral prolapse, pulmonary stenosis, pulmonary regurgitation, tricuspid stenosis, and tricuspid regurgitation.

16. The method of claim 12, further comprising administering to the subject in need thereof one or more additional therapeutic therapies or agents.

17. The method of claim 16, wherein at least one of the one or more additional therapeutic therapies or agents comprises Idebenone; Eplerenone; an electrical nerve stimulator; AVI-4658; Ataluren; BMN044/PRO044; CAT-1004; Micro-Dystrophin AAV Gene Therapy (SGT-001); Galectin-1 Therapy (SB-002); LTBB4 (SB-001); rAAV2.5-CMV-minidystrophin; Glutamine; NFKB inhibitors; Sarcoglycan, delta (35 kDa dystrophin-associated glycoprotein); insulin like growth factor-1 (IGF-1); and combinations thereof.

18. The method of claim 16, wherein the pharmaceutical composition and at least one of the one or more additional therapeutic therapies or agents are administered to the subject sequentially or in rotation.

\* \* \* \* \*

SEQUENCE LISTING

```
<160> NUMBER OF SEQ ID NOS: 109

<210> SEQ ID NO 1
<211> LENGTH: 22
<212> TYPE: RNA
<213> ORGANISM: Artificial Sequence
<220> FEATURE:
<223> OTHER INFORMATION: hsa-let-7a-5p MIMAT0000062 Sense

<400> SEQUENCE: 1
ugagguagua gguuguauag uu                                            22

<210> SEQ ID NO 2
<211> LENGTH: 22
<212> TYPE: RNA
<213> ORGANISM: Artificial Sequence
<220> FEATURE:
<223> OTHER INFORMATION: hsa-let-7a-5p MIMAT0000062 Anti-sense

<400> SEQUENCE: 2
acuccaucau ccaacauauc aa                                            22

<210> SEQ ID NO 3
<211> LENGTH: 22
<212> TYPE: RNA
<213> ORGANISM: Artificial Sequence
<220> FEATURE:
<223> OTHER INFORMATION: hsa-let-7c-5p MIMAT0000064 Sense

<400> SEQUENCE: 3
ugagguagua gguuguaugg uu                                            22

<210> SEQ ID NO 4
<211> LENGTH: 22
<212> TYPE: RNA
```

<213> ORGANISM: Artificial Sequence
<220> FEATURE:
<223> OTHER INFORMATION: hsa-let-7c-5p MIMAT0000064 Anti-sense

<400> SEQUENCE: 4
acuccaucau ccaacauacc aa                                    22

<210> SEQ ID NO 5
<211> LENGTH: 22
<212> TYPE: RNA
<213> ORGANISM: Artificial Sequence
<220> FEATURE:
<223> OTHER INFORMATION: hsa-miR-99a-5p MIMAT0000097 Sense

<400> SEQUENCE: 5
aacccguaga uccgaucuug ug                                    22

<210> SEQ ID NO 6
<211> LENGTH: 22
<212> TYPE: RNA
<213> ORGANISM: Artificial Sequence
<220> FEATURE:
<223> OTHER INFORMATION: hsa-miR-99a-5p MIMAT0000097 Anti-sense

<400> SEQUENCE: 6
uugggcaucu aggcuagaac ac                                    22

<210> SEQ ID NO 7
<211> LENGTH: 22
<212> TYPE: RNA
<213> ORGANISM: Artificial Sequence
<220> FEATURE:
<223> OTHER INFORMATION: hsa-miR-100-5p MIMAT0000098 Sense

<400> SEQUENCE: 7
aacccguaga uccgaacuug ug                                    22

<210> SEQ ID NO 8
<211> LENGTH: 22
<212> TYPE: RNA
<213> ORGANISM: Artificial Sequence
<220> FEATURE:
<223> OTHER INFORMATION: hsa-miR-100-5p MIMAT0000098 Anti-sense

<400> SEQUENCE: 8
uugggcaucu aggcuugaac ac                                    22

<210> SEQ ID NO 9
<211> LENGTH: 22
<212> TYPE: RNA
<213> ORGANISM: Danio rerio
<220> FEATURE:
<221> NAME/KEY: misc_feature
<222> LOCATION: (0)...(0)
<223> OTHER INFORMATION: dre-let-7a-5p

<400> SEQUENCE: 9
ugagguagua gguuguauag uu                                    22

<210> SEQ ID NO 10
<211> LENGTH: 22
<212> TYPE: RNA
<213> ORGANISM: Mus musculus
<220> FEATURE:
<221> NAME/KEY: misc_feature
<222> LOCATION: (0)...(0)
<223> OTHER INFORMATION: mmu-let-7a-5p -continued

```
<400> SEQUENCE: 10
ugagguagua gguuguauag uu                                              22

<210> SEQ ID NO 11
<211> LENGTH: 22
<212> TYPE: RNA
<213> ORGANISM: Rattus norvegicus
<220> FEATURE:
<221> NAME/KEY: misc_feature
<222> LOCATION: (0)...(0)
<223> OTHER INFORMATION: rno-let-7a-5p

<400> SEQUENCE: 11
ugagguagua gguuguauag uu                                              22

<210> SEQ ID NO 12
<211> LENGTH: 22
<212> TYPE: RNA
<213> ORGANISM: Sus scrofa
<220> FEATURE:
<221> NAME/KEY: misc_feature
<222> LOCATION: (0)...(0)
<223> OTHER INFORMATION: ssc-let-7a-5p

<400> SEQUENCE: 12
ugagguagua gguuguauag uu                                              22

<210> SEQ ID NO 13
<211> LENGTH: 22
<212> TYPE: RNA
<213> ORGANISM: Pan troglodytes
<220> FEATURE:
<221> NAME/KEY: misc_feature
<222> LOCATION: (0)...(0)
<223> OTHER INFORMATION: ptr-let-7a-5p

<400> SEQUENCE: 13
ugagguagua gguuguauag uu                                              22

<210> SEQ ID NO 14
<211> LENGTH: 22
<212> TYPE: RNA
<213> ORGANISM: Homo sapiens
<220> FEATURE:
<221> NAME/KEY: misc_feature
<222> LOCATION: (0)...(0)
<223> OTHER INFORMATION: hsa-let-7a-5p

<400> SEQUENCE: 14
ugagguagua gguuguauag uu                                              22

<210> SEQ ID NO 15
<211> LENGTH: 22
<212> TYPE: RNA
<213> ORGANISM: Canis familiaris
<220> FEATURE:
<221> NAME/KEY: misc_feature
<222> LOCATION: (0)...(0)
<223> OTHER INFORMATION: cfa-let-7a-5p

<400> SEQUENCE: 15
ugagguagua gguuguauag uu                                              22

<210> SEQ ID NO 16
<211> LENGTH: 22
<212> TYPE: RNA
```

```
<213> ORGANISM: Danio rerio
<220> FEATURE:
<221> NAME/KEY: misc_feature
<222> LOCATION: (0)...(0)
<223> OTHER INFORMATION: dre-let-7c-5p

<400> SEQUENCE: 16
ugagguagua gguuguaugg uu                                              22

<210> SEQ ID NO 17
<211> LENGTH: 22
<212> TYPE: RNA
<213> ORGANISM: Mus musculus
<220> FEATURE:
<221> NAME/KEY: misc_feature
<222> LOCATION: (0)...(0)
<223> OTHER INFORMATION: mmu-let-7c-5p

<400> SEQUENCE: 17
ugagguagua gguuguaugg uu                                              22

<210> SEQ ID NO 18
<211> LENGTH: 22
<212> TYPE: RNA
<213> ORGANISM: Rattus norvegicus
<220> FEATURE:
<221> NAME/KEY: misc_feature
<222> LOCATION: (0)...(0)
<223> OTHER INFORMATION: rno-let-7c-5p

<400> SEQUENCE: 18
ugagguagua gguuguaugg uu                                              22

<210> SEQ ID NO 19
<211> LENGTH: 22
<212> TYPE: RNA
<213> ORGANISM: Sus scrofa
<220> FEATURE:
<221> NAME/KEY: misc_feature
<222> LOCATION: (0)...(0)
<223> OTHER INFORMATION: ssc-let-7c-5p

<400> SEQUENCE: 19
ugagguagua gguuguaugg uu                                              22

<210> SEQ ID NO 20
<211> LENGTH: 22
<212> TYPE: RNA
<213> ORGANISM: Pan troglodytes
<220> FEATURE:
<221> NAME/KEY: misc_feature
<222> LOCATION: (0)...(0)
<223> OTHER INFORMATION: ptr-let-7c-5p

<400> SEQUENCE: 20
ugagguagua gguuguaugg uu                                              22

<210> SEQ ID NO 21
<211> LENGTH: 22
<212> TYPE: RNA
<213> ORGANISM: Homo sapiens
<220> FEATURE:
<221> NAME/KEY: misc_feature
<222> LOCATION: (0)...(0)
<223> OTHER INFORMATION: hsa-let-7c-5p

<400> SEQUENCE: 21
ugagguagua gguuguaugg uu                                              22
```

-continued

```
<210> SEQ ID NO 22
<211> LENGTH: 22
<212> TYPE: RNA
<213> ORGANISM: Canis familiaris
<220> FEATURE:
<221> NAME/KEY: misc_feature
<222> LOCATION: (0)...(0)
<223> OTHER INFORMATION: cfa-let-7c-5p

<400> SEQUENCE: 22
ugagguagua gguuguaugg uu                                              22

<210> SEQ ID NO 23
<211> LENGTH: 22
<212> TYPE: RNA
<213> ORGANISM: Danio rerio
<220> FEATURE:
<221> NAME/KEY: misc_feature
<222> LOCATION: (0)...(0)
<223> OTHER INFORMATION: dre-miR-99a-5p

<400> SEQUENCE: 23
aacccguaga uccgaucuug ug                                              22

<210> SEQ ID NO 24
<211> LENGTH: 22
<212> TYPE: RNA
<213> ORGANISM: Mus musculus
<220> FEATURE:
<221> NAME/KEY: misc_feature
<222> LOCATION: (0)...(0)
<223> OTHER INFORMATION: mmu-miR-99a-5p

<400> SEQUENCE: 24
aacccguaga uccgaucuug ug                                              22

<210> SEQ ID NO 25
<211> LENGTH: 22
<212> TYPE: RNA
<213> ORGANISM: Rattus norvegicus
<220> FEATURE:
<221> NAME/KEY: misc_feature
<222> LOCATION: (0)...(0)
<223> OTHER INFORMATION: rno-miR-99a-5p

<400> SEQUENCE: 25
aacccguaga uccgaucuug ug                                              22

<210> SEQ ID NO 26
<211> LENGTH: 21
<212> TYPE: RNA
<213> ORGANISM: Canis familiaris
<220> FEATURE:
<221> NAME/KEY: misc_feature
<222> LOCATION: (0)...(0)
<223> OTHER INFORMATION: cfa-miR-99a

<400> SEQUENCE: 26
aacccguaga uccgaucuug u                                               21

<210> SEQ ID NO 27
<211> LENGTH: 22
<212> TYPE: RNA
<213> ORGANISM: Sus scrofa
<220> FEATURE:
<221> NAME/KEY: misc_feature
<222> LOCATION: (0)...(0)
```

<223> OTHER INFORMATION: ssc-miR-99a

<400> SEQUENCE: 27
aacccguaga uccgaucuug ug                                              22

<210> SEQ ID NO 28
<211> LENGTH: 22
<212> TYPE: RNA
<213> ORGANISM: Pan troglodytes
<220> FEATURE:
<221> NAME/KEY: misc_feature
<222> LOCATION: (0)...(0)
<223> OTHER INFORMATION: ptr-miR-99a

<400> SEQUENCE: 28
aacccguaga uccgaucuug ug                                              22

<210> SEQ ID NO 29
<211> LENGTH: 22
<212> TYPE: RNA
<213> ORGANISM: Homo sapiens
<220> FEATURE:
<221> NAME/KEY: misc_feature
<222> LOCATION: (0)...(0)
<223> OTHER INFORMATION: hsa-miR-99a-5p

<400> SEQUENCE: 29
aacccguaga uccgaucuug ug                                              22

<210> SEQ ID NO 30
<211> LENGTH: 22
<212> TYPE: RNA
<213> ORGANISM: Danio rerio
<220> FEATURE:
<221> NAME/KEY: misc_feature
<222> LOCATION: (0)...(0)
<223> OTHER INFORMATION: dre-miR-100-5p

<400> SEQUENCE: 30
aacccguaga uccgaacuug ug                                              22

<210> SEQ ID NO 31
<211> LENGTH: 22
<212> TYPE: RNA
<213> ORGANISM: Mus musculus
<220> FEATURE:
<221> NAME/KEY: misc_feature
<222> LOCATION: (0)...(0)
<223> OTHER INFORMATION: mmu-miR-100-5p

<400> SEQUENCE: 31
aacccguaga uccgaacuug ug                                              22

<210> SEQ ID NO 32
<211> LENGTH: 22
<212> TYPE: RNA
<213> ORGANISM: Rattus norvegicus
<220> FEATURE:
<221> NAME/KEY: misc_feature
<222> LOCATION: (0)...(0)
<223> OTHER INFORMATION: rno-miR-100-5p

<400> SEQUENCE: 32
aacccguaga uccgaacuug ug                                              22

<210> SEQ ID NO 33
<211> LENGTH: 22

```
<212> TYPE: RNA
<213> ORGANISM: Sus scrofa
<220> FEATURE:
<221> NAME/KEY: misc_feature
<222> LOCATION: (0)...(0)
<223> OTHER INFORMATION: ssc-miR-100

<400> SEQUENCE: 33
aacccguaga uccgaacuug ug                                              22

<210> SEQ ID NO 34
<211> LENGTH: 22
<212> TYPE: RNA
<213> ORGANISM: Pan troglodytes
<220> FEATURE:
<221> NAME/KEY: misc_feature
<222> LOCATION: (0)...(0)
<223> OTHER INFORMATION: ptr-miR-100

<400> SEQUENCE: 34
aacccguaga uccgaacuug ug                                              22

<210> SEQ ID NO 35
<211> LENGTH: 22
<212> TYPE: RNA
<213> ORGANISM: Homo sapiens
<220> FEATURE:
<221> NAME/KEY: misc_feature
<222> LOCATION: (0)...(0)
<223> OTHER INFORMATION: hsa-miR-100-5p

<400> SEQUENCE: 35
aacccguaga uccgaacuug ug                                              22

<210> SEQ ID NO 36
<211> LENGTH: 19
<212> TYPE: DNA
<213> ORGANISM: Artificial Sequence
<220> FEATURE:
<223> OTHER INFORMATION: JRX0100

<400> SEQUENCE: 36
ccatacaacc tactacctc                                                  19

<210> SEQ ID NO 37
<211> LENGTH: 19
<212> TYPE: DNA
<213> ORGANISM: Artificial Sequence
<220> FEATURE:
<223> OTHER INFORMATION: JRX0101

<400> SEQUENCE: 37
ctatacaacc tactacctc                                                  19

<210> SEQ ID NO 38
<211> LENGTH: 18
<212> TYPE: DNA
<213> ORGANISM: Artificial Sequence
<220> FEATURE:
<223> OTHER INFORMATION: JRX0102

<400> SEQUENCE: 38
catacaacct actacctc                                                   18

<210> SEQ ID NO 39
<211> LENGTH: 18
<212> TYPE: DNA
```

```
<213> ORGANISM: Artificial Sequence
<220> FEATURE:
<223> OTHER INFORMATION: JRX0103

<400> SEQUENCE: 39
tatacaacct actacctc                                               18

<210> SEQ ID NO 40
<211> LENGTH: 17
<212> TYPE: DNA
<213> ORGANISM: Artificial Sequence
<220> FEATURE:
<223> OTHER INFORMATION: JRX0104

<400> SEQUENCE: 40
atacaaccta ctacctc                                                17

<210> SEQ ID NO 41
<211> LENGTH: 17
<212> TYPE: DNA
<213> ORGANISM: Artificial Sequence
<220> FEATURE:
<223> OTHER INFORMATION: JRX0105

<400> SEQUENCE: 41
atacaaccta ctacctc                                                17

<210> SEQ ID NO 42
<211> LENGTH: 16
<212> TYPE: DNA
<213> ORGANISM: Artificial Sequence
<220> FEATURE:
<223> OTHER INFORMATION: JRX0106

<400> SEQUENCE: 42
tacaacctac tacctc                                                 16

<210> SEQ ID NO 43
<211> LENGTH: 16
<212> TYPE: DNA
<213> ORGANISM: Artificial Sequence
<220> FEATURE:
<223> OTHER INFORMATION: JRX0107

<400> SEQUENCE: 43
tacaacctac tacctc                                                 16

<210> SEQ ID NO 44
<211> LENGTH: 15
<212> TYPE: DNA
<213> ORGANISM: Artificial Sequence
<220> FEATURE:
<223> OTHER INFORMATION: JRX0108

<400> SEQUENCE: 44
acaacctact acctc                                                  15

<210> SEQ ID NO 45
<211> LENGTH: 15
<212> TYPE: DNA
<213> ORGANISM: Artificial Sequence
<220> FEATURE:
<223> OTHER INFORMATION: JRX0109

<400> SEQUENCE: 45
acaacctact acctc                                                  15
```

<210> SEQ ID NO 46
<211> LENGTH: 19
<212> TYPE: DNA
<213> ORGANISM: Artificial Sequence
<220> FEATURE:
<223> OTHER INFORMATION: JRX0110

<400> SEQUENCE: 46
caagttcgga tctacgggt                    19

<210> SEQ ID NO 47
<211> LENGTH: 19
<212> TYPE: DNA
<213> ORGANISM: Artificial Sequence
<220> FEATURE:
<223> OTHER INFORMATION: JRX0111

<400> SEQUENCE: 47
caagatcgga tctacgggt                    19

<210> SEQ ID NO 48
<211> LENGTH: 18
<212> TYPE: DNA
<213> ORGANISM: Artificial Sequence
<220> FEATURE:
<223> OTHER INFORMATION: JRX0112

<400> SEQUENCE: 48
aagatcggat ctacgggt                     18

<210> SEQ ID NO 49
<211> LENGTH: 18
<212> TYPE: DNA
<213> ORGANISM: Artificial Sequence
<220> FEATURE:
<223> OTHER INFORMATION: JRX0113

<400> SEQUENCE: 49
aagttcggat ctacgggt                     18

<210> SEQ ID NO 50
<211> LENGTH: 17
<212> TYPE: DNA
<213> ORGANISM: Artificial Sequence
<220> FEATURE:
<223> OTHER INFORMATION: JRX0114

<400> SEQUENCE: 50
agatcggatc tacgggt                      17

<210> SEQ ID NO 51
<211> LENGTH: 17
<212> TYPE: DNA
<213> ORGANISM: Artificial Sequence
<220> FEATURE:
<223> OTHER INFORMATION: JRX0115

<400> SEQUENCE: 51
agttcggatc tacgggt                      17

<210> SEQ ID NO 52
<211> LENGTH: 16
<212> TYPE: DNA
<213> ORGANISM: Artificial Sequence
<220> FEATURE:

<223> OTHER INFORMATION: JRX0116

<400> SEQUENCE: 52
gatcggatct acgggt                                                           16

<210> SEQ ID NO 53
<211> LENGTH: 16
<212> TYPE: DNA
<213> ORGANISM: Artificial Sequence
<220> FEATURE:
<223> OTHER INFORMATION: JRX0117

<400> SEQUENCE: 53
gttcggatct acgggt                                                           16

<210> SEQ ID NO 54
<211> LENGTH: 15
<212> TYPE: DNA
<213> ORGANISM: Artificial Sequence
<220> FEATURE:
<223> OTHER INFORMATION: JRX0118

<400> SEQUENCE: 54
atcggatcta cgggt                                                            15

<210> SEQ ID NO 55
<211> LENGTH: 15
<212> TYPE: DNA
<213> ORGANISM: Artificial Sequence
<220> FEATURE:
<223> OTHER INFORMATION: JRX0119

<400> SEQUENCE: 55
ttcggatcta cgggt                                                            15

<210> SEQ ID NO 56
<211> LENGTH: 7
<212> TYPE: DNA
<213> ORGANISM: Artificial Sequence
<220> FEATURE:
<223> OTHER INFORMATION: Loop sequence

<400> SEQUENCE: 56 tgtgctt                                                                      7

<210> SEQ ID NO 57
<211> LENGTH: 21
<212> TYPE: DNA
<213> ORGANISM: Artificial Sequence
<220> FEATURE:
<223> OTHER INFORMATION: Forward primer for mouse U6 promoter

<400> SEQUENCE: 57
tcgcacagac ttgtgggaga a                                                     21

<210> SEQ ID NO 58
<211> LENGTH: 28
<212> TYPE: DNA
<213> ORGANISM: Artificial Sequence
<220> FEATURE:
<223> OTHER INFORMATION: Reverse primer mouse U6 promoter

<400> SEQUENCE: 58
cgcacattaa gcctctatag ttactagg                                              28

-continued

```
<210> SEQ ID NO 59
<211> LENGTH: 57
<212> TYPE: DNA
<213> ORGANISM: Artificial Sequence
<220> FEATURE:
<223> OTHER INFORMATION: let-7a-5p sequence in vector JBT-miR1

<400> SEQUENCE: 59
gtgaggtagt aggttgtata gtttcaagag aactatacaa cctactacct cattttt         57

<210> SEQ ID NO 60
<211> LENGTH: 57
<212> TYPE: DNA
<213> ORGANISM: Artificial Sequence
<220> FEATURE:
<223> OTHER INFORMATION: miR-99a-5p sequence in vector JBT-miR1

<400> SEQUENCE: 60
gaacccgtag atccgatctt gtgtcaagag cacaagatcg gatctacggg ttttttt         57

<210> SEQ ID NO 61
<211> LENGTH: 120
<212> TYPE: DNA
<213> ORGANISM: Artificial Sequence
<220> FEATURE:
<223> OTHER INFORMATION: (H1-)let-7a-5p & (U6)-miR-99a-5p in vector
      JBT-miR1

<400> SEQUENCE: 61
gtgaggtagt aggttgtata gtttcaagag aactatacaa cctactacct cattttt gag     60 ctcaaaaaaa cccgtagatc cgatcttgtg ctcttgacac aagatcggat ctacgggttc     120

<210> SEQ ID NO 62
<211> LENGTH: 57
<212> TYPE: DNA
<213> ORGANISM: Artificial Sequence
<220> FEATURE:
<223> OTHER INFORMATION: let-7c-5p sequence in vector JBT-miR1

<400> SEQUENCE: 62
gtgaggtagt aggttgtatg gtttcaagag aaccatacaa cctactacct cattttt         57

<210> SEQ ID NO 63
<211> LENGTH: 57
<212> TYPE: DNA
<213> ORGANISM: Artificial Sequence
<220> FEATURE:
<223> OTHER INFORMATION: miR-100-5p sequence in vector JBT-miR1

<400> SEQUENCE: 63
gaacccgtag atccgaactt gtgtcaagag cacaagttcg gatctacggg ttttttt         57

<210> SEQ ID NO 64
<211> LENGTH: 120
<212> TYPE: DNA
<213> ORGANISM: Artificial Sequence
<220> FEATURE:
<223> OTHER INFORMATION: (H1-)let-7C-5p & (U6)-miR-100-5p in vector
      JBT-miR1

<400> SEQUENCE: 64
gtgaggtagt aggttgtatg gtttcaagag aaccatacaa cctactacct cattttt gag     60 ctcaaaaaaa cccgtagatc cgaacttgtg ctcttgacac aagttcggat ctacgggttc     120

<210> SEQ ID NO 65
```

```
<211> LENGTH: 19
<212> TYPE: DNA
<213> ORGANISM: Artificial Sequence
<220> FEATURE:
<223> OTHER INFORMATION: let-7c inhibitor sequence

<400> SEQUENCE: 65
ccatacaacc tactacctc                                                 19

<210> SEQ ID NO 66
<211> LENGTH: 19
<212> TYPE: DNA
<213> ORGANISM: Artificial Sequence
<220> FEATURE:
<223> OTHER INFORMATION: let-7a inhibitor sequence

<400> SEQUENCE: 66
ctatacaacc tactacctc                                                 19

<210> SEQ ID NO 67
<211> LENGTH: 18
<212> TYPE: DNA
<213> ORGANISM: Artificial Sequence
<220> FEATURE:
<223> OTHER INFORMATION: let-7c inhibitor sequence

<400> SEQUENCE: 67
catacaacct actacctc                                                  18

<210> SEQ ID NO 68
<211> LENGTH: 18
<212> TYPE: DNA
<213> ORGANISM: Artificial Sequence
<220> FEATURE:
<223> OTHER INFORMATION: let-7a inhibitor sequence

<400> SEQUENCE: 68
tatacaacct actacctc                                                  18

<210> SEQ ID NO 69
<211> LENGTH: 17
<212> TYPE: DNA
<213> ORGANISM: Artificial Sequence
<220> FEATURE:
<223> OTHER INFORMATION: let-7a/c inhibitor sequence

<400> SEQUENCE: 69
atacaaccta ctacctc                                                   17

<210> SEQ ID NO 70
<211> LENGTH: 17
<212> TYPE: DNA
<213> ORGANISM: Artificial Sequence
<220> FEATURE:
<223> OTHER INFORMATION: let-7a/c inhibitor sequence

<400> SEQUENCE: 70
atacaaccta ctacctc                                                   17

<210> SEQ ID NO 71
<211> LENGTH: 16
<212> TYPE: DNA
<213> ORGANISM: Artificial Sequence
<220> FEATURE:
<223> OTHER INFORMATION: let-7a/c inhibitor sequence

<400> SEQUENCE: 71
```

```
tacaacctac tacctc                                              16

<210> SEQ ID NO 72
<211> LENGTH: 16
<212> TYPE: DNA
<213> ORGANISM: Artificial Sequence
<220> FEATURE:
<223> OTHER INFORMATION: let-7a/c inhibitor sequence

<400> SEQUENCE: 72
tacaacctac tacctc                                              16

<210> SEQ ID NO 73
<211> LENGTH: 15
<212> TYPE: DNA
<213> ORGANISM: Artificial Sequence
<220> FEATURE:
<223> OTHER INFORMATION: let-7a/c inhibitor sequence

<400> SEQUENCE: 73
acaacctact acctc                                               15

<210> SEQ ID NO 74
<211> LENGTH: 15
<212> TYPE: DNA
<213> ORGANISM: Artificial Sequence
<220> FEATURE:
<223> OTHER INFORMATION: let-7a/c inhibitor sequence

<400> SEQUENCE: 74
acaacctact acctc                                               15

<210> SEQ ID NO 75
<211> LENGTH: 19
<212> TYPE: DNA
<213> ORGANISM: Artificial Sequence
<220> FEATURE:
<223> OTHER INFORMATION: miR-100 inhibitor sequence

<400> SEQUENCE: 75
caagttcgga tctacgggt                                           19

<210> SEQ ID NO 76
<211> LENGTH: 19
<212> TYPE: DNA
<213> ORGANISM: Artificial Sequence
<220> FEATURE:
<223> OTHER INFORMATION: miR-99 inhibitor sequence

<400> SEQUENCE: 76
caagatcgga tctacgggt                                           19

<210> SEQ ID NO 77
<211> LENGTH: 18
<212> TYPE: DNA
<213> ORGANISM: Artificial Sequence
<220> FEATURE:
<223> OTHER INFORMATION: miR-99 inhibitor sequence

<400> SEQUENCE: 77
aagatcggat ctacgggt                                            18

<210> SEQ ID NO 78
<211> LENGTH: 18
<212> TYPE: DNA
```

```
<213> ORGANISM: Artificial Sequence
<220> FEATURE:
<223> OTHER INFORMATION: miR-100 inhibitor sequence

<400> SEQUENCE: 78
aagttcggat ctacgggt                                                 18

<210> SEQ ID NO 79
<211> LENGTH: 17
<212> TYPE: DNA
<213> ORGANISM: Artificial Sequence
<220> FEATURE:
<223> OTHER INFORMATION: miR-99 inhibitor sequence

<400> SEQUENCE: 79
agatcggatc tacgggt                                                  17

<210> SEQ ID NO 80
<211> LENGTH: 17
<212> TYPE: DNA
<213> ORGANISM: Artificial Sequence
<220> FEATURE:
<223> OTHER INFORMATION: miR-100 inhibitor sequence

<400> SEQUENCE: 80
agttcggatc tacgggt                                                  17

<210> SEQ ID NO 81
<211> LENGTH: 16
<212> TYPE: DNA
<213> ORGANISM: Artificial Sequence
<220> FEATURE:
<223> OTHER INFORMATION: miR-99 inhibitor sequence

<400> SEQUENCE: 81
gatcggatct acgggt                                                   16

<210> SEQ ID NO 82
<211> LENGTH: 16
<212> TYPE: DNA
<213> ORGANISM: Artificial Sequence
<220> FEATURE:
<223> OTHER INFORMATION: miR-100 inhibitor sequence

<400> SEQUENCE: 82
gttcggatct acgggt                                                   16

<210> SEQ ID NO 83
<211> LENGTH: 15
<212> TYPE: DNA
<213> ORGANISM: Artificial Sequence
<220> FEATURE:
<223> OTHER INFORMATION: miR-99 inhibitor sequence

<400> SEQUENCE: 83
atcggatcta cgggt                                                    15

<210> SEQ ID NO 84
<211> LENGTH: 15
<212> TYPE: DNA
<213> ORGANISM: Artificial Sequence
<220> FEATURE:
<223> OTHER INFORMATION: miR-100 inhibitor sequence

<400> SEQUENCE: 84
ttcggatcta cgggt                                                    15
```

<210> SEQ ID NO 85
<211> LENGTH: 6558
<212> TYPE: DNA
<213> ORGANISM: Artificial Sequence
<220> FEATURE:
<223> OTHER INFORMATION: viral vector JBT-miR1

<400> SEQUENCE: 85

```
cggcctcagt gagcgagcgc gcagagaggg agtggccaac tccatcacta ggggttcctg      60
cggccgcacg cgtctagtta ttaatagtaa tcgaattcgt gttactcata gcagatcacc     120
gctgctcgtc aactgaggcg cccaggcagt caggggactt cgtcgcccgg cctcagtgag     180
cgagcgcgca gcgagggagt ggcccacttc atcactaggc gttcctgcgg ccgcacgcgt     240
ctagttcact catagtaatc gaacttcgcg ttactcataa cagtgaacgc tgacgtcatc     300
aacccgctcc aaggaatcgc gggcccagtg tcactaggcg gggaacaccc agcgcgcgtg     360
cgccctggca ggaagatggc tgcgaggac aggggagtgg cgccccgcaa tattttccat      420
gtcggctatg tgttcttggg aaatcaccat aaacgtgaaa tgtctttgga tttgggaatc     480
ttataagttt ctgtatgaga ccactcggat ccgtgaggta gtaggttgta tagtttcaag     540
agaactatac aacctactac ctcattttg agctcaaaaa aaacccgtag atccgatctt      600
gtgctcttga cacaagatcg gatctacggg tttcggtgtt cgcgtccttt ccacaagata     660
tataaaccca agaaatcgaa atactttcaa gttacggtaa gcatatgata gtccatttta     720
aaacataatt ttaaaactgc aaactaccca agaaattatt actttctacg tcacgtattt     780
tgtactaata tctttgtgtt tacagtcaaa ttaattctaa ttatctctct aacagccttg     840
tatcgtatat gcaaatatga aggaatcatg ggaaataggc cctcttcctg cccgaccttc     900
tgtcccctcc accccacgtc gacattaatg aagcttggcg actagtaata ctgtaatagt     960
aatcaattac ggggtcatta gttcatagcc catatatgga gttccgcgtt acataactta    1020
cggtaaatgg cccgcctggc tgaccgccca acgaccccg cctatatgca tggccccagg     1080
aaatcggaaa tagttcaagt tacggtaagc atatgatagt ccattttaaa acattatttt    1140
aaaactgcaaa ctacccaaga aattatact ttctacgtca cgtattttgt actaatatct    1200
ttgtgtttac agtcaaatta ttctaattat ctctcctaac agccttgtat cgtatatgca    1260
aatatgaacg gaatcatggg aaataggccc tcttcctgcc cgaccttctg tcccctccac    1320
cccacgtcga cgacaggatt ggtgacagag aacgctgacg tcatcaaccc gctccaagga    1380
atcgcgggcc cagtgtcact aggcgggaac acccagcgcg cgtgcgccct ggcaggaaga    1440
tggctgtgag ggacagggga gtggcgccct gcaatatttg catgtcgcta tgtgttctgg    1500
gaaatcacca taaacgtgaa atgtctttgg atttgggaat cttataagtt ctgtatgaga    1560
ccactcggat ccgtgaggt agtaggttgt atggtttcaa gagaaccata caacctacta    1620
cctcattttt gagctcaaaa aaaacccgt agatccgaac ttgtgctctt gacacaagtt    1680
cggatctacg ggttcggtgt tcgcgtcctt tccacaagat atataaaccc aagaaatcga    1740
aatactttca agttacggta agcatatgat agtccatttt aaaacataat tttaaaactg    1800
caaactaccc aagaaattat tactttctac gtcacgtatt ttgtactaat atctttgtgt    1860
ttacagtcaa attaattcta attatctctc taacagcctt gtatcgtata tgcaaatatg    1920
aaggaatcat gggaaatagg ccctcttcct gcccgacctt aagcttggcg actagtaata    1980
ctgtaatagt aatcaattac ggggtcatta gttcatagcc catatatgga gttccgcgtt    2040
```

-continued

```
acataactta cggtaaatgg cccgcctggc tgaccgccca acgaccccg ccccatgatg   2100 ccctagtaaa tggcccgcct ggctgaccgc caacgaccc ccgcccattg acgtcaataa   2160
tgacgtatgt tcccatagta acgccaatag ggactttcca ttgacgtcaa tgggtggagt   2220
atttacggta aactgcccac ttggcagtac atcaagtgta tcatatgcca agtacgcccc   2280
ctattgacgt caatgacggt aaatggcccg cctggcatta tgcccagtac atgaccttat   2340
gggactttcc tacttggcag tacatctacg tattagtcat cgctattacc atggtgatgc   2400
ggttttggca gtacatcaat gggcgtggat agcggtttga ctcacgggga tttccaagtc   2460 tccacccat tgacgtcaat gggagtttgt tttgcaccaa aatcaacggg actttccaaa   2520
atgtcgtaac aactccgccc cattgacgca aatgggcggt aggcgtgtac ggtgggaggt   2580
ctatataagc agagctggtt tagtgaaccg tcagatccgc tagagatccg gtaccgagga   2640
gatctgccgc cgcgatcgcc ggcgcgccag atctcacgct taactagcta gcggaccgac   2700
gcgtacgcgg ccgctcgaga tggtgagcaa gggcgaggag ctgttcaccg gggtggtgcc   2760
catcctggtc gagctggacg gcgacgtaaa cggccacaag ttcagcgtgt ccggcgaggg   2820
cgagggcgat gccacctacg gcaagctgac cctgaagttc atctgcacca ccggcaagct   2880
gcccgtgccc tggcccaccc tcgtgaccac cctgacctac ggcgtgcagt gcttcagccg   2940
ctaccccgac cacatgaagc agcacgactt cttcaagtcc gccatgcccg aaggctacgt   3000
ccaggagcgc accatcttct tcaaggacga cggcaactac aagacccgcg ccgaggtgaa   3060
gttcgagggc gacaccctgg tgaaccgcat cgagctgaag ggcatcgact tcaaggagga   3120
cggcaacatc ctggggcaca agctggagta caactacaac agccacaacg tctatatcat   3180
ggccgacaag cagaagaacg gcatcaaggt gaacttcaag atccgccaca acatcgagga   3240
cggcagcgtg cagctcgccg accactacca gcagaacacc cccatcggcg acggccccgt   3300
gctgctgccc gacaaccact acctgagcac ccagtccgcc ctgagcaaag accccaacga   3360
gaagcgcgat cacatggtcc tgctggagtt cgtgaccgcc gccgggatca ctctcggcat   3420
ggacgagctg tacaagtaag tcgaggatta aaggatgac gacgataaat cgtcgagca   3480 ccaccaccac caccactaat aaggtttatc cgatccaccg gatctagata agatatccga   3540
tccaccggat ctagataact gatcataatc agccatacca catttgtaga ggttttactt   3600
gctttaaaaa acctcccaca cctccccctg aacctgaaac ataaaatgaa tgcaattgtt   3660
gttgttaact tgtttattgc agcttataat ggttacaaat aaagcaatag catcacaaat   3720
ttcacaaata aagcattttt ttcactgcat tctagttgtg gtttgtccaa actcatcaat   3780
gtatcttaac gcggtaacca cgtgcggacc gagcggccgc aggaacccct agtgatggag   3840
ttggccactc cctctctgcg cgctcgctcg ctcactgagg ccgggcgacc aaaggtcgcc   3900
cgacgcccgg gctttgcccg gcggcctca gtgagcgagc gagcgcgcag ctgcctgcag   3960
gggcgcctga tgcggtattt tctccttacg catctgtgcg gtatttcaca ccgcatacgt   4020
caaagcaacc atagtacgcg ccctgtagcg gcgcattaag cgcggcgggt gtggtggtta   4080
cgcgcagcgt gaccgctaca cttgccagcg ccctagcgcc cgctcctttc gctttcttcc   4140
cttcctttct cgccacgttc gccggctttc ccgtcaagc tctaaatcgg gggctccctt   4200
tagggttccg atttagtgct ttacggcacc tcgaccccaa aaaacttgat ttgggtgatg   4260
gttcacgtag tgggccatcg ccctgataga cggtttttcg ccctttgacg ttggagtcca   4320
cgttctttaa tagtggactc ttgttccaaa ctggaacaac actcaaccct atctcgggct   4380
attcttttga tttataaggg attttgccga tttcggccta ttggttaaaa aatgagctga   4440
```

```
tttaacaaaa atttaacgcg aattttaaca aaatattaac gtttacaatt ttatggtgca    4500
ctctcagtac aatctgctct gatgccgcat agttaagcca gccccgacac ccgccaacac    4560
ccgctgacgc gccctgacgg gcttgtctgc tcccggcatc cgcttacaga caagctgtga    4620
ccgtctccgg gagctgcatg tgtcagaggt tttcaccgtc atcaccgaaa cgcgcgagac    4680
gaaagggcct cgtgatacgc ctatttttat aggttaatgt catgataata atggtttctt    4740
agacgtcagg tggcactttt cggggaaatg tgcgcggaac ccctatttgt ttatttttct    4800
aaatacattc aaatatgtat ccgctcatga caataaacc ctgataaatg cttcaataat    4860
attgaaaaag gaagagtatg agtattcaac atttccgtgt cgcccttatt ccctttttg     4920 cggcattttg ccttcctgtt tttgctcacc cagaaacgct ggtgaaagta aaagatgctg    4980
aagatcagtt gggtgcacga gtgggttaca tcgaactgga tctcaacagc ggtaagatcc    5040
ttgagagttt tcgccccgaa gaacgttttc caatgatgag cacttttaaa gttctgctat    5100
gtggcgcggt attatcccgt attgacgccg ggcaagagca actcggtcgc cgcatacact    5160
attctcagaa tgacttggtt gagtactcac cagtcacaga aaagcatctt acggatggca    5220
tgacagtaag agaattatgc agtgctgcca taaccatgag tgataacact gcggccaact    5280
tacttctgac aacgatcgga ggaccgaagg agctaaccgc ttttttgcac aacatggggg    5340
atcatgtaac tcgccttgat cgttgggaac cggagctgaa tgaagccata ccaaacgacg    5400
agcgtgacac cacgatgcct gtagcaatgg caacaacgtt gcgcaaacta ttaactggcg    5460
aactacttac tctagcttcc cggcaacaat taatagactg gatggaggcg gataaagttg    5520
caggaccact tctgcgctcg gcccttccgg ctggctggtt tattgctgat aaatctggag    5580
ccggtgagcg tgggtctcgc ggtatcattg cagcactggg gccagatggt aagccctccc    5640
gtatcgtagt tatctacacg acggggagtc aggcaactat ggatgaacga atagacaga    5700 tcgctgagat aggtgcctca ctgattaagc attggtaact gtcagaccaa gtttactcat    5760
atatacttta gattgattta aaacttcatt tttaatttaa aaggatctag gtgaagatcc    5820
tttttgataa tctcatgacc aaaatccctt aacgtgagtt ttcgttccac tgagcgtcag    5880
accccgtaga aaagatcaaa ggatcttctt gagatccttt ttttctgcgc gtaatctgct    5940
gcttgcaaac aaaaaaacca ccgctaccag cggtggtttg tttgccggat caagagctac    6000
caactctttt tccgaaggta actggcttca gcagagcgca gataccaaat actgtccttc    6060
tagtgtagcc gtagttaggc caccacttca agaactctgt agcaccgcct acatacctcg    6120
ctctgctaat cctgttacca gtggctgctg ccagtggcga taagtcgtgt cttaccgggt    6180
tggactcaag acgatagtta ccggataagg cgcagcggtc gggctgaacg gggggttcgt    6240
gcacacagcc cagcttggag cgaacgacct acaccgaact gagatacta cagcgtgagc    6300 tatgagaaag cgccacgctt cccgaaggga gaaaggcgga caggtatccg gtaagcggca    6360
gggtcggaac aggagagcgc acgagggagc ttccaggggg aaacgcctgg tatctttata    6420
gtcctgtcgg gtttcgccac ctctgacttg agcgtcgatt tttgtgatgc tcgtcagggg    6480
ggcggagcct atggaaaaac gccagcaacg cggccttttt acggttcctg gccttttgct    6540
ggccttttgc tcacatgt                                                  6558
```

<210> SEQ ID NO 86
<211> LENGTH: 120
<212> TYPE: DNA
<213> ORGANISM: Artificial Sequence
<220> FEATURE:

```
<223> OTHER INFORMATION: let-7a-5p sequence in vector JBT-miR2

<400> SEQUENCE: 86
gacggcgcta ggatcatcaa caactataca accaatgtac tacctcacaa gtattctggt    60
cacagaatac aacaactata caaccaatgt actacctcac aagatgatcc tagcgccgtc   120

<210> SEQ ID NO 87
<211> LENGTH: 120
<212> TYPE: DNA
<213> ORGANISM: Artificial Sequence
<220> FEATURE:
<223> OTHER INFORMATION: let-7a-5p Reverse Complement in vector JBT-miR2

<400> SEQUENCE: 87
gacggcgcta ggatcatctt gtgaggtagt acattggttg tatagttgtt gtattctgtg    60
accagaatac ttgtgaggta gtacattggt tgtatagttg ttgatgatcc tagcgccgtc   120

<210> SEQ ID NO 88
<211> LENGTH: 120
<212> TYPE: DNA
<213> ORGANISM: Artificial Sequence
<220> FEATURE:
<223> OTHER INFORMATION: miR-99a-5p sequence in vector JBT-miR2

<400> SEQUENCE: 88
gacggcgcta ggatcatcaa ccacaagatc ggaaatgtct acgggtacaa gtattctggt    60
cacagaatac aaccacaaga tcggaaatgt ctacgggtac aagatgatcc tagcgccgtc   120

<210> SEQ ID NO 89
<211> LENGTH: 120
<212> TYPE: DNA
<213> ORGANISM: Artificial Sequence
<220> FEATURE:
<223> OTHER INFORMATION: miR-99a-5p Reverse Complement in vector
      JBT-miR2

<400> SEQUENCE: 89
gacggcgcta ggatcatctt gtacccgtag acatttccga tcttgtggtt gtattctgtg    60
accagaatac ttgtacccgt agacatttcc gatcttgtgg ttgatgatcc tagcgccgtc   120

<210> SEQ ID NO 90
<211> LENGTH: 22
<212> TYPE: RNA
<213> ORGANISM: Artificial Sequence
<220> FEATURE:
<223> OTHER INFORMATION: hsa-miR-99a-5p MIMAT0000097

<400> SEQUENCE: 90
aacccguaga uccgaucuug ug                                              22

<210> SEQ ID NO 91
<211> LENGTH: 22
<212> TYPE: DNA
<213> ORGANISM: Artificial Sequence
<220> FEATURE:
<223> OTHER INFORMATION: hsa-miR-99a-5p MIMAT0000097 complementary
      sequence

<400> SEQUENCE: 91
cacaagatcg gatctacggg tt                                              22

<210> SEQ ID NO 92
<211> LENGTH: 40
```

```
<212> TYPE: DNA
<213> ORGANISM: Artificial Sequence
<220> FEATURE:
<223> OTHER INFORMATION: 99aFOR

<400> SEQUENCE: 92
aacactagtc acaagatcgg atctacgggt taagcttgtt                           40

<210> SEQ ID NO 93
<211> LENGTH: 40
<212> TYPE: DNA
<213> ORGANISM: Artificial Sequence
<220> FEATURE:
<223> OTHER INFORMATION: 99Arev

<400> SEQUENCE: 93
aacaagctta acccguagau ccgaucuugu gactagtgtt                           40

<210> SEQ ID NO 94
<211> LENGTH: 22
<212> TYPE: RNA
<213> ORGANISM: Artificial Sequence
<220> FEATURE:
<223> OTHER INFORMATION: hsa-miR-100-5p MIMAT0000098

<400> SEQUENCE: 94
aacccguaga uccgaacuug ug                                              22

<210> SEQ ID NO 95
<211> LENGTH: 22
<212> TYPE: DNA
<213> ORGANISM: Artificial Sequence
<220> FEATURE:
<223> OTHER INFORMATION: hsa-miR-100-5p MIMAT0000098 complementary
      sequence

<400> SEQUENCE: 95
cacaagttcg gatctacggg tt                                              22

<210> SEQ ID NO 96
<211> LENGTH: 40
<212> TYPE: DNA
<213> ORGANISM: Artificial Sequence
<220> FEATURE:
<223> OTHER INFORMATION: 100 FORWARD PRIMER

<400> SEQUENCE: 96
aacactagtc acaagttcgg atctacgggt taagcttgtt                           40

<210> SEQ ID NO 97
<211> LENGTH: 40
<212> TYPE: DNA
<213> ORGANISM: Artificial Sequence
<220> FEATURE:
<223> OTHER INFORMATION: 100 REVERSE PRIMER

<400> SEQUENCE: 97
aacaagctta acccguagau ccgaacuugu gactagtgtt                           40

<210> SEQ ID NO 98
<211> LENGTH: 22
<212> TYPE: RNA
<213> ORGANISM: Artificial Sequence
<220> FEATURE:
<223> OTHER INFORMATION: hsa-let-7a-5p MIMAT0000062

<400> SEQUENCE: 98
```

-continued ugagguagua gguuguauag uu                                              22

<210> SEQ ID NO 99
<211> LENGTH: 22
<212> TYPE: DNA
<213> ORGANISM: Artificial Sequence
<220> FEATURE:
<223> OTHER INFORMATION: hsa-let-7a-5p MIMAT0000062 complementary
      sequence

<400> SEQUENCE: 99
aactatacaa cctactacct ca                                              22

<210> SEQ ID NO 100
<211> LENGTH: 40
<212> TYPE: DNA
<213> ORGANISM: Artificial Sequence
<220> FEATURE:
<223> OTHER INFORMATION: LET7A FORWARD PRIMER

<400> SEQUENCE: 100
aacactagta actatacaac ctactacctc aaagcttgtt                            40

<210> SEQ ID NO 101
<211> LENGTH: 40
<212> TYPE: DNA
<213> ORGANISM: Artificial Sequence
<220> FEATURE:
<223> OTHER INFORMATION: LET7A REVERSE PRIMER

<400> SEQUENCE: 101
aacaagcttu gagguaguag guuguauagu uactagtgtt                            40

<210> SEQ ID NO 102
<211> LENGTH: 22
<212> TYPE: RNA
<213> ORGANISM: Artificial Sequence
<220> FEATURE:
<223> OTHER INFORMATION: hsa-let-7c-5p MIMAT0000064

<400> SEQUENCE: 102
ugagguagua gguuguaugg uu                                              22

<210> SEQ ID NO 103
<211> LENGTH: 22
<212> TYPE: DNA
<213> ORGANISM: Artificial Sequence
<220> FEATURE:
<223> OTHER INFORMATION: hsa-let-7c-5p MIMAT0000064 complementary
      sequence

<400> SEQUENCE: 103
aaccatacaa cctactacct ca                                              22

<210> SEQ ID NO 104
<211> LENGTH: 40
<212> TYPE: DNA
<213> ORGANISM: Artificial Sequence
<220> FEATURE:
<223> OTHER INFORMATION: LET7C FORWARD PRIMER

<400> SEQUENCE: 104
aacactagta accatacaac ctactacctc aaagcttgtt                            40

<210> SEQ ID NO 105

```
<211> LENGTH: 40
<212> TYPE: DNA
<213> ORGANISM: Artificial Sequence
<220> FEATURE:
<223> OTHER INFORMATION: LET7C REVERSE PRIMER

<400> SEQUENCE: 105
aacaagcttu gagguaguag guuguauggu uactagtgtt                    40

<210> SEQ ID NO 106
<211> LENGTH: 6436
<212> TYPE: DNA
<213> ORGANISM: Artificial Sequence
<220> FEATURE:
<223> OTHER INFORMATION: pMIR-REPORT-Luciferase_hsa-miR-99a

<400> SEQUENCE: 106
gacgaaagat tggtgtggaa agtccccagg ctccccagca ggcagaagta tgcaaagcat    60
gcatctcaat tagtcagcaa ccaggtgtgg aaagtcccca ggctcccag caggcagaag    120 tatgcaaagc atgcatctca attagtcagc aaccatagtc ccgcccctaa ctccgcccat   180
cccgccccta actccgccca gttccgccca ttctccgccc catggctgac taatttttttt  240 tatttatgca gaggccgagg ccgcctcggc ctctgagcta ttccagaagt agtgaggagg   300
cttttttgga ggcctaggct tttgcaaaaa gctagcttgc atgcctgcag gtcggccgcc   360
acgaccggtg ccgccaccat cccctgaccc acgcccctga cccctcacaa ggagacgacc   420
ttccatgacc gagtacaagc ccacggtgcg cctcgccacc gcgacgacg tccccgggc    480 cgtacgcacc ctcgccgccg cgttcgccga ctaccccgcc acgcgccaca ccgtcgaccc    540
ggaccgccac atcgagcggg tcaccgagct gcaagaactc ttcctcacgc gcgtcgggct   600
cgacatcggc aaggtgtggg tcgcggacga cggcgccgcg gtggcggtct ggaccacgcc   660
ggagagcgtc gaagcggggg cggtgttcgc cgagatcggc ccgcgcatgg ccgagttgag   720
cggttcccgg ctgccgcgc agcaacagat ggaaggcctc ctggcgccgc accgcccaa     780 ggagcccgcg tggttcctgg ccaccgtcgg cgtctcgccc gaccaccagg caagggtct    840 gggcagcgcc gtcgtgctcc ccggagtgga ggcggccgag cgcgccgggg tgcccgcctt   900
cctggagacc tccgcgcccc gcaacctccc cttctacgag cggctcggct tcaccgtcac    960
cgccgacgtc gaggtgcccg aaggaccgcg cacctggtgc atgacccgca agcccggtgc   1020
ctgacgcccg cccacgacc cgcagcgccc gaccgaaagg agcgcacgac cccatggctc   1080
cgaccgaagc cacccggggc ggccccgccg acccgcacc cgcccccgag gccaccgac     1140 tctagaggat cataatcagc cataccacat ttgtagaggt tttacttgct taaaaaacc    1200 tcccacacct cccccctgaac ctgaaacata aaatgaatgc aattgttgtt gttaacttgt  1260
ttattgcagc ttataatggt tacaaataaa gcaatagcat cacaaatttc acaaataaag   1320
catttttttc actgcaatct cgtgatacgc ctattttttat aggttaatgt catgataata  1380
atggtttctt agacgtcagg tggcactttt cggggaaatg tgcgcggaac ccctatttgt   1440
ttatttttct aaatacattc aaatatgtat ccgctcatga caataaacc ctgataaatg   1500 cttcaataat attgaaaaag gaagagtatg agtattcaac atttccgtgt cgcccttatt   1560
cccttttttg cggcattttg ccttcctgtt tttgctcacc cagaaacgct ggtgaaagta   1620
aaagatgctg aagatcagtt gggtgcacga gtgggttaca tcgaactgga tctcaacagc   1680
ggtaagatcc ttgagagttt tcgccccgaa gaacgttttc caatgatgag cacttttaaa   1740
gttctgctat gtggcgcggt attatcccgt attgacgccg ggcaagagca actcggtcgc   1800
```

```
cgcatacact attctcagaa tgacttggtt gagtactcac cagtcacaga aaagcatctt    1860
acggatggca tgacagtaag agaattatgc agtgctgcca taaccatgag tgataacact    1920
gcggccaact tacttctgac aacgatcgga ggaccgaagg agctaaccgc ttttttgcac    1980
aacatggggg atcatgtaac tcgccttgat cgttgggaac cggagctgaa tgaagccata    2040
ccaaacgacg agcgtgacac cacgatgcct gtagcaatgg caacaacgtt gcgcaaacta    2100
ttaactggcg aactacttac tctagcttcc cggcaacaat taatagactg gatggaggcg    2160
gataaagttg caggaccact tctgcgctcg gcccttccgg ctggctggtt tattgctgat    2220
aaatctggag ccgtgagcg tgggtctcgc ggtatcattg cagcactggg gccagatggt    2280
aagccctccc gtatcgtagt tatctacacg acggggagtc aggcaactat ggatgaacga    2340
aatagacaga tcgctgagat aggtgcctca ctgattaagc attggtaact gtcagaccaa    2400
gtttactcat atatacttta gattgattta aaacttcatt tttaatttaa aaggatctag    2460
gtgaagatcc ttttttgataa tctcatgacc aaaatccctt aacgtgagtt ttcgttccac    2520
tgagcgtcag accccgtaga aaagatcaaa ggatcttctt gagatccttt ttttctgcgc    2580
gtaatctgct gcttgcaaac aaaaaaacca ccgctaccag cggtggtttt tttgccggat    2640
caagagctac caactctttt tccgaaggta actggcttca gcagagcgca gataccaaat    2700
actgttcttc tagtgtagcc gtagttaggc caccacttca agaactctgt agcaccgcct    2760
acatacctcg ctctgctaat cctgttacca gtggctgctg ccagtggcga taagtcgtgt    2820
cttaccgggt tggactcaag acgatagtta ccggataagg cgcagcggtc gggctgaacg    2880
gggggttcgt gcacacagcc cagcttggag cgaacgacct acaccgaact gagataccta    2940
cagcgtgagc tatgagaaag cgccacgctt cccgaaggga gaaaggcgga caggtatccg    3000
gtaagcggca gggtcggaac aggagagcgc acgagggagc ttccagggg aaacgcctgg    3060 tatctttata gtcctgtcgg gtttcgccac ctctgacttg agcgtcgatt tttgtgatgc    3120
tcgtcagggg ggcggagcct atggaaaaac gccagcaacg cggccttttt acggttcctg    3180
gccttttgct ggccttttgc tcacatgttc tttcctgcgt tatcccctga ttctgtggat    3240
aaccgtatta ccgcctttga gtgagctgat accgctcgcc gcagccgaac gaccgagcgc    3300
agcgagtcag tgagcgagga agcggaagag cgcccaatac gcaaaccgcc tctccccgcg    3360
cgttggccga ttcattaatg cagctggcac gacaggtttc ccgactggaa agcgggcagt    3420
gagcgcaacg caattaatgt gagttagctc actcattagg caccccaggc tttacacttt    3480
atgcttccgg ctcgtatgtt gtgtggaatt gtgagcggat aacaatttca cacaggaaac    3540
agctatgaca tgattacgaa ttgcaacgat ttaggtgaca ctatagaaga aaggaatta    3600 atacgactca ctatagggag agagagagaa ttaccctcac taaagggagg agaagcatga    3660
attcaaggta ccagatctta gttattaata gtaatcaatt acgggtcat tagttcatag    3720 cccatatatg gagttccgcg ttacataact tacggtaaat ggcccgcctg gctgaccgcc    3780
caacgacccc cgcccattga cgtcaataat gacgtatgtt cccatagtaa cgccaatagg    3840
gactttccat tgacgtcaat gggtggagta tttacggtaa actgcccact ggcagtaca    3900 tcaagtgtat catatgccaa gtacgccccc tattgacgtc aatgacgta aatggcccgc    3960 ctggcattat gcccagtaca tgaccttatg gactttcct acttggcagt acatctacgt    4020
attagtcatc gctattacca tggtgatgcg gttttggcag tacatcaatg ggcgtggata    4080
gcggtttgac tcacggggat ttccaagtct ccaccccatt gacgtcaatg ggagtttgtt    4140
```

```
ttggcaccaa aatcaacggg actttccaaa atgtcgtaac aactccgccc cattgacgca    4200
aatgggcggt aggcgtgtac ggtgggaggt ctatataagc agagctggtt tagtgaaccg    4260
tggatccacc atggaagacg ccaaaaacat aaagaaaggc ccggcgccat tctatcctct    4320
agaggatgga accgctggag agcaactgca taaggctatg aagagatacg ccctggttcc    4380
tggaacaatt gcttttacag atgcacatat cgaggtgaac atcacgtacg cggaatactt    4440
cgaaatgtcc gttcggttgg cagaagctat gaaacgatat gggctgaata caaatcacag    4500
aatcgtcgta tgcagtgaaa actctcttca attctttatg ccggtgttgg gcgcgttatt    4560
tatcggagtt gcagttgcgc ccgcgaacga catttataat gaacgtgaat tgctcaacag    4620
tatgaacatt tcgcagccta ccgtagtgtt tgtttccaaa aaggggttgc aaaaaatttt    4680
gaacgtgcaa aaaaaattac caataatcca gaaaattatt atcatggatt ctaaaacgga    4740
ttaccaggga tttcagtcga tgtacacgtt cgtcacatct catctacctc ccggttttaa    4800
tgaatacgat tttgtaccag agtcctttga tcgtgacaaa acaattgcac tgataatgaa    4860
ttcctctgga tctactgggt tacctaaggg tgtggcccct ccgcatagaa ctgcctgcgt    4920
cagattctcg catgccagag atcctatttt tggcaatcaa atcgttccgg atactgcgat    4980
tttaagtgtt gtcccattcc atcacggttt tggaatgttt actacactcg gatatttgat    5040
atgtggattt cgagtcgtct taatgtatag atttgaagaa gagctgtttt tacgatccct    5100
tcaggattac aaaattcaaa gtgcgttgct agtaccaacc ctattttcat tcttcgccaa    5160
aagcactctg attgacaaat acgatttatc taatttacac gaaattgctt ctgggggcgc    5220
acctctttcg aaagaagtcg gggaagcggt tgcaaaacgc ttccatcttc cagggatacg    5280
acaaggatat gggctcactg agactacatc agctattctg attacacccg aggggatga    5340
taaaccgggc gcggtcggta agttgttcc attttttgaa gcgaaggttg tggatctgga    5400
taccgggaaa acgctgggcg ttaatcagag aggcgaatta tgtgtcagag acctatgat    5460
tatgtccggt tatgtaaaca atccggaagc gaccaacgcc ttgattgaca aggatggatg    5520
gctacattct ggagacatag cttactggga cgaagacgaa cacttcttca tagttgaccg    5580
cttgaagtct ttaattaaat acaaaggata tcaggtggcc cccgctgaat tggaatcgat    5640
attgttacaa caccccaaca tcttcgacgc gggcgtggca ggtcttcccg acgatgacgc    5700
cggtgaactt cccgccgccg ttgttgtttt ggagcacgga aagacgatga cggaaaaaga    5760
gatcgtggat tacgtcgcca gtcaagtaac aaccgcgaaa agttgcgcg gaggagttgt    5820
gtttgtggac gaagtaccga aaggtcttac cggaaaactc gacgcaagaa aaatcagaga    5880
gatcctcata aaggccaaga agggcggaaa gtccaaattg ctcgagtgat gaaagctgcg    5940
cactagtcac aagatcggat ctacgggtta agcttaataa aggatctttt attttcattg    6000
gatctgtgtg ttggttttt gtatgcggcc gctagcttgg cactggccgt cgttttacaa    6060
cgtcgtgact gggaaaaccc tggcgttacc caacttaatc gccttgcagc acatccccct    6120
ttcgccagct ggcgtaatag cgaagaggcc cgcaccgatc gcccttccca acagttgcgc    6180
agcctgaatg gcgaatggcg cctgatgcgg tattttctcc ttacgcatct gtgcggtatt    6240
tcacaccgca tatggtgcac tctcagtaca atctgctctg atgccgcata gttaagccag    6300
ccccgacacc cgccaacacc cgctgacgcg ccctgacggg cttgtctgct cccggcatcc    6360
gcttacagac aagctgtgac cgtctccggg agctgcatgt gtcagaggtt ttcaccgtca    6420
tcaccgaaac gcgcga                                                    6436
```

<210> SEQ ID NO 107
<211> LENGTH: 6436
<212> TYPE: DNA
<213> ORGANISM: Artificial Sequence
<220> FEATURE:
<223> OTHER INFORMATION: pMIR-REPORT-Luciferase_hsa-miR-100

<400> SEQUENCE: 107

| | | | | | |
|---|---|---|---|---|---|
| gacgaaagat | tggtgtggaa | agtccccagg | ctccccagca | ggcagaagta | tgcaaagcat | 60 |
| gcatctcaat | tagtcagcaa | ccaggtgtgg | aaagtcccca | ggctccccag | caggcagaag | 120 |
| tatgcaaagc | atgcatctca | attagtcagc | aaccatagtc | ccgcccctaa | ctccgcccat | 180 |
| cccgcccta | actccgccca | gttccgccca | ttctccgccc | catggctgac | taatttttt | 240 |
| tatttatgca | gaggccgagg | ccgcctcggc | ctctgagcta | ttccagaagt | agtgaggagg | 300 |
| ctttttttgga | ggcctaggct | tttgcaaaaa | gctagcttgc | atgcctgcag | gtcggccgcc | 360 |
| acgaccggtg | ccgccaccat | cccctgaccc | acgcccctga | ccctcacaa | ggagacgacc | 420 |
| ttccatgacc | gagtacaagc | ccacggtgcg | cctcgccacc | cgcgacgacg | tcccccgggc | 480 |
| cgtacgcacc | ctcgccgccg | cgttcgccga | ctaccccgcc | acgcgccaca | ccgtcgaccc | 540 |
| ggaccgccac | atcgagcggg | tcaccgagct | gcaagaactc | ttcctcacgc | gcgtcgggct | 600 |
| cgacatcggc | aaggtgtggg | tcgcggacga | cggcgccgcg | gtggcggtct | ggaccacgcc | 660 |
| ggagagcgtc | gaagcggggg | cggtgttcgc | cgagatcggc | ccgcgcatgg | ccgagttgag | 720 |
| cggttcccgg | ctggccgcgc | agcaacagat | ggaaggcctc | ctggcgccgc | accggcccaa | 780 |
| ggagcccgcg | tggttcctgg | ccaccgtcgg | cgtctcgccc | gaccaccagg | gcaagggtct | 840 |
| gggcagcgcc | gtcgtgctcc | ccggagtgga | ggcggccgag | cgcgccgggg | tgcccgcctt | 900 |
| cctggagacc | tccgcgcccc | gcaacctccc | cttctacgag | cggctcggct | tcaccgtcac | 960 |
| cgccgacgtc | gaggtgcccg | aaggaccgcg | cacctggtgc | atgacccgca | agcccggtgc | 1020 |
| ctgacgcccg | ccccacgacc | cgcagcgccc | gaccgaaagg | agcgcacgac | cccatggctc | 1080 |
| cgaccgaagc | caccggggc | ggccccgccg | accccgcacc | cgccccgag | gcccaccgac | 1140 |
| tctagaggat | cataatcagc | cataccacat | ttgtagaggt | tttacttgct | ttaaaaaacc | 1200 |
| tcccacacct | ccccctgaac | ctgaaacata | aaatgaatgc | aattgttgtt | gttaacttgt | 1260 |
| ttattgcagc | ttataatggt | tacaaataaa | gcaatagcat | cacaaatttc | acaaataaag | 1320 |
| catttttttc | actgcaatct | cgtgatacgc | ctatttttat | aggttaatgt | catgataata | 1380 |
| atggtttctt | agacgtcagg | tggcactttt | cggggaaatg | tgcgcggaac | ccctatttgt | 1440 |
| ttatttttct | aaatacattc | aaatatgtat | ccgctcatga | caataaacc | ctgataaatg | 1500 |
| cttcaataat | attgaaaaag | gaagagtatg | agtattcaac | atttccgtgt | cgcccttatt | 1560 |
| cccttttttg | cggcatttg | ccttcctgtt | tttgctcacc | cagaaacgct | ggtgaaagta | 1620 |
| aaagatgctg | aagatcagtt | gggtgcacga | gtgggttaca | tcgaactgga | tctcaacagc | 1680 |
| ggtaagatcc | ttgagagttt | tcgccccgaa | gaacgttttc | caatgatgag | cacttttaaa | 1740 |
| gttctgctat | gtggcgcggt | attatcccgt | attgacgccg | ggcaagagca | actcggtcgc | 1800 |
| cgcatacact | attctcagaa | tgacttggtt | gagtactcac | cagtcacaga | aaagcatctt | 1860 |
| acggatggca | tgacagtaag | agaattatgc | agtgctgcca | taaccatgag | tgataacact | 1920 |
| gcggccaact | tacttctgac | aacgatcgga | ggaccgaagg | agctaaccgc | ttttttgcac | 1980 |
| aacatggggg | atcatgtaac | tcgccttgat | cgttgggaac | cggagctgaa | tgaagccata | 2040 |
| ccaaacgacg | agcgtgacac | cacgatgcct | gtagcaatgg | caacaacgtt | gcgcaaacta | 2100 |

```
ttaactggcg aactacttac tctagcttcc cggcaacaat taatagactg gatggaggcg    2160
gataaagttg caggaccact tctgcgctcg gcccttccgg ctggctggtt tattgctgat    2220
aaatctggag ccggtgagcg tgggtctcgc ggtatcattg cagcactggg gccagatggt    2280
aagccctccc gtatcgtagt tatctacacg acggggagtc aggcaactat ggatgaacga    2340
aatagacaga tcgctgagat aggtgcctca ctgattaagc attggtaact gtcagaccaa    2400
gtttactcat atatacttta gattgattta aaacttcatt tttaatttaa aaggatctag    2460
gtgaagatcc ttttttgataa tctcatgacc aaaatccctt aacgtgagtt ttcgttccac    2520
tgagcgtcag accccgtaga aaagatcaaa ggatcttctt gagatccttt ttttctgcgc    2580
gtaatctgct gcttgcaaac aaaaaaacca ccgctaccag cggtggtttt tttgccggat    2640
caagagctac caactctttt tccgaaggta actggcttca gcagagcgca gataccaaat    2700
actgttcttc tagtgtagcc gtagttaggc caccacttca agaactctgt agcaccgcct    2760
acatacctcg ctctgctaat cctgttacca gtggctgctg ccagtggcga taagtcgtgt    2820
cttaccgggt tggactcaag acgatagtta ccggataagg cgcagcggtc gggctgaacg    2880
gggggttcgt gcacacagcc cagcttggag cgaacgacct acaccgaact gagatacccta   2940 cagcgtgagc tatgagaaag cgccacgctt cccgaaggga gaaaggcgga caggtatccg    3000
gtaagcggca gggtcggaac aggagagcgc acgagggagc ttccaggggg aaacgcctgg    3060
tatctttata gtcctgtcgg gtttcgccac ctctgacttg agcgtcgatt tttgtgatgc    3120
tcgtcagggg ggcggagcct atggaaaaac gccagcaacg cggcctttt acggttcctg    3180 gccttttgct ggccttttgc tcacatgttc tttcctgcgt tatcccctga ttctgtggat    3240
aaccgtatta ccgcctttga gtgagctgat accgctcgcc gcagccgaac gaccgagcgc    3300
agcgagtcag tgagcgagga agcggaagag cgcccaatac gcaaaccgcc tctccccgcg    3360
cgttggccga ttcattaatg cagctggcac gacaggtttc ccgactggaa agcgggcagt    3420
gagcgcaacg caattaatgt gagttagctc actcattagg cacccaggc tttacacttt    3480 atgcttccgg ctcgtatgtt gtgtggaatt gtgagcggat aacaatttca cacaggaaac    3540
agctatgaca tgattacgaa ttgcaacgat ttaggtgaca ctatagaaga gaaggaatta    3600
atacgactca ctataggag agagagagaa ttaccctcac taaagggagg agaagcatga    3660
attcaaggta ccagatctta gttattaata gtaatcaatt acgggtcat tagttcatag    3720 cccatatatg gagttccgcg ttacataact tacggtaaat ggcccgcctg gctgaccgcc    3780
caacgacccc cgcccattga cgtcaataat gacgtatgtt cccatagtaa cgccaatagg    3840
gactttccat tgacgtcaat gggtggagta tttacggtaa actgcccact ggcagtaca    3900 tcaagtgtat catatgccaa gtacgccccc tattgacgtc aatgacggta atggcccgc    3960 ctggcattat gcccagtaca tgaccttatg gactttcct acttggcagt acatctacgt    4020
attagtcatc gctattacca tggtgatgcg gttttggcag tacatcaatg gcgtggata    4080 gcggtttgac tcacggggat ttccaagtct ccaccccatt gacgtcaatg ggagtttgtt    4140
ttggcaccaa aatcaacggg actttccaaa atgtcgtaac aactccgccc cattgacgca    4200
aatgggcggt aggcgtgtac ggtgggaggt ctatataagc agagctggtt tagtgaaccg    4260
tggatccacc atggaagacg ccaaaaacat aaagaaaggc ccggcgccat tctatcctct    4320
agaggatgga accgctggag agcaactgca taaggctatg aagagatacg ccctggttcc    4380
tggaacaatt gcttttacag atgcacatat cgaggtgaac atcacgtacg cggaatactt    4440
cgaaatgtcc gttcggttgg cagaagctat gaaacgatat gggctgaata caaatcacag    4500
```

```
aatcgtcgta tgcagtgaaa actctcttca attctttatg ccggtgttgg gcgcgttatt    4560
tatcggagtt gcagttgcgc ccgcgaacga catttataat gaacgtgaat tgctcaacag    4620
tatgaacatt tcgcagccta ccgtagtgtt tgtttccaaa aggggttgc aaaaaatttt     4680 gaacgtgcaa aaaaaattac caataatcca gaaaattatt atcatggatt ctaaaacgga    4740
ttaccaggga tttcagtcga tgtacacgtt cgtcacatct catctacctc ccggttttaa    4800
tgaatacgat tttgtaccag agtcctttga tcgtgacaaa acaattgcac tgataatgaa    4860
ttcctctgga tctactgggt tacctaaggg tgtggccctt ccgcatagaa ctgcctgcgt    4920
cagattctcg catgccagag atcctatttt tggcaatcaa atcgttccgg atactgcgat    4980
tttaagtgtt gtcccattcc atcacggttt tggaatgttt actacactcg gatatttgat    5040
atgtggattt cgagtcgtct taatgtatag atttgaagaa gagctgtttt tacgatccct    5100
tcaggattac aaaattcaaa gtgcgttgct agtaccaacc ctatttcat tcttcgccaa     5160 aagcactctg attgacaaat acgatttatc taatttacac gaaattgctt ctgggggcgc    5220
acctctttcg aaagaagtcg gggaagcggt tgcaaaacgc ttccatcttc cagggatacg    5280
acaaggatat gggctcactg agactacatc agctattctg attacacccg agggggatga    5340
taaaccgggc gcggtcggta aagttgttcc attttttgaa gcgaaggttg tggatctgga    5400
taccgggaaa acgctgggcg ttaatcagag aggcgaatta tgtgtcagag gacctatgat    5460
tatgtccggt tatgtaaaca atccggaagc gaccaacgcc ttgattgaca aggatggatg    5520
gctacattct ggagacatag cttactggga cgaagacgaa cacttcttca tagttgaccg    5580
cttgaagtct ttaattaaat acaaaggata tcaggtggcc cccgctgaat tggaatcgat    5640
attgttacaa cacccaaca tcttcgacgc gggcgtggca ggtcttcccg acgatgacgc     5700
cggtgaactt cccgccgccg ttgttgtttt ggagcacgga aagacgatga cggaaaaaga    5760
gatcgtggat tacgtcgcca gtcaagtaac aaccgcgaaa aagttgcgcg gaggagttgt    5820
gtttgtggac gaagtaccga aaggtcttac cggaaaactc gacgcaagaa aaatcagaga    5880
gatcctcata aaggccaaga agggcggaaa gtccaaattg ctcgagtgat gaaagctgcg    5940
cactagtcac aagttcggat ctacgggtta agcttaataa aggatctttt attttcattg    6000
gatctgtgtg ttggtttttt gtatgcggcc gctagcttgg cactggccgt cgttttacaa    6060
cgtcgtgact gggaaaaccc tggcgttacc caacttaatc gccttgcagc acatccccct    6120
ttcgccagct ggcgtaatag cgaagaggcc cgcaccgatc gcccttccca acagttgcgc    6180
agcctgaatg gcgaatggcg cctgatgcgg tattttctcc ttacgcatct gtgcggtatt    6240
tcacaccgca tatggtgcac tctcagtaca atctgctctg atgccgcata gttaagccag    6300
ccccgacacc cgccaacacc cgctgacgcg ccctgacggg cttgtctgct cccggcatcc    6360
gcttacagac aagctgtgac cgtctccggg agctgcatgt gtcagaggtt ttcaccgtca    6420
tcaccgaaac gcgcga                                                    6436
```

<210> SEQ ID NO 108
<211> LENGTH: 6436
<212> TYPE: DNA
<213> ORGANISM: Artificial Sequence
<220> FEATURE:
<223> OTHER INFORMATION: pMIR-REPORT-Luciferase_hsa-let-7a-5p

<400> SEQUENCE: 108

```
gacgaaagat tggtgtggaa agtccccagg ctccccagca ggcagaagta tgcaaagcat      60
```

```
gcatctcaat tagtcagcaa ccaggtgtgg aaagtcccca ggctccccag caggcagaag    120
tatgcaaagc atgcatctca attagtcagc aaccatagtc ccgcccctaa ctccgcccat    180 cccgcccta actccgccca gttccgccca ttctccgccc catggctgac taatttttt     240 tatttatgca gaggccgagg ccgcctcggc ctctgagcta ttccagaagt agtgaggagg    300
cttttttgga ggcctaggct tttgcaaaaa gctagcttgc atgcctgcag gtcggccgcc    360
acgaccggtg ccgccaccat cccctgaccc acgcccctga ccctcacaa ggagacgacc     420 ttccatgacc gagtacaagc ccacggtgcg cctcgccacc cgcgacgacg tccccgggc     480 cgtacgcacc ctcgccgccg cgttcgccga ctaccccgcc acgcgccaca ccgtcgaccc    540
ggaccgccac atcgagcggg tcaccgagct gcaagaactc ttcctcacgc gcgtcgggct    600
cgacatcggc aaggtgtggg tcgcggacga cggcgccgcg gtggcggtct ggaccacgcc    660
ggagagcgtc gaagcggggg cggtgttcgc cgagatcggc ccgcgcatgg ccgagttgag    720
cggttcccgg ctggccgcgc agcaacagat ggaaggcctc ctggcgccgc accggcccaa    780
ggagcccgcg tggttcctgg ccaccgtcgg cgtctcgccc gaccaccagg caagggtct     840 gggcagcgcc gtcgtgctcc cggagtggga ggcggccgag cgcgccgggg tgcccgcctt    900
cctggagacc tccgcgcccc gcaacctccc cttctacgag cggctcggct tcaccgtcac    960
cgccgacgtc gaggtgcccg aaggaccgcg cacctggtgc atgacccgca agcccggtgc   1020
ctgacgcccg ccccacgacc cgcagcgccc gaccgaaagg agcgcacgac cccatggctc   1080
cgaccgaagc cacccggggc ggccccgccg accccgcacc cgccccgag gcccaccgac    1140 tctagaggat cataatcagc cataccacat ttgtagaggt tttacttgct ttaaaaaacc   1200
tcccacacct cccctgaac ctgaaacata aatgaatgc aattgttgtt gttaacttgt     1260
ttattgcagc ttataatggt tacaaataaa gcaatagcat cacaaatttc acaaataaag   1320
catttttttc actgcaatct cgtgatacgc ctatttttat aggttaatgt catgataata   1380
atggtttctt agacgtcagg tggcactttt cggggaaatg tgcgcggaac ccctatttgt   1440
ttatttttct aaatacattc aaatatgtat ccgctcatga caataaacc ctgataaatg     1500 cttcaataat attgaaaaag gaagagtatg agtattcaac atttccgtgt cgcccttatt   1560
cccttttttg cggcattttg ccttcctgtt tttgctcacc cagaaacgct ggtgaaagta   1620
aaagatgctg aagatcagtt gggtgcacga gtgggttaca tcgaactgga tctcaacagc   1680
ggtaagatcc ttgagagttt tcgccccgaa gaacgttttc caatgatgag cacttttaaa   1740
gttctgctat gtggcgcggt attatcccgt attgacgccg ggcaagagca actcggtcgc   1800
cgcatacact attctcagaa tgacttggtt gagtactcac cagtcacaga aaagcatctt   1860
acggatggca tgacagtaag agaattatgc agtgctgcca taaccatgag tgataacact   1920
gcggccaact tacttctgac aacgatcgga ggaccgaagg agctaaccgc ttttttgcac   1980
aacatggggg atcatgtaac tcgccttgat cgttgggaac cggagctgaa tgaagccata   2040
ccaaacgacg agcgtgacac cacgatgcct gtagcaatgg caacaacgtt gcgcaaacta   2100
ttaactggcg aactacttac tctagcttcc cggcaacaat taatagactg gatggaggcg   2160
gataaagttg caggaccact tctgcgctcg gcccttccgg ctggctggtt tattgctgat   2220
aaatctggag ccggtgagcg tgggtctcgc ggtatcattg cagcactggg gccagatggt   2280
aagccctccc gtatcgtagt tatctacacg acggggagtc aggcaactat ggatgaacga   2340
aatagacaga tcgctgagat aggtgcctca ctgattaagc attggtaact gtcagaccaa   2400
gtttactcat atatacttta gattgattta aaacttcatt tttaatttaa aaggatctag   2460
```

```
gtgaagatcc tttttgataa tctcatgacc aaaatccctt aacgtgagtt ttcgttccac    2520
tgagcgtcag accccgtaga aaagatcaaa ggatcttctt gagatccttt ttttctgcgc    2580
gtaatctgct gcttgcaaac aaaaaaacca ccgctaccag cggtggtttt tttgccggat    2640
caagagctac caactctttt tccgaaggta actggcttca gcagagcgca gataccaaat    2700
actgttcttc tagtgtagcc gtagttaggc caccacttca agaactctgt agcaccgcct    2760
acatacctcg ctctgctaat cctgttacca gtggctgctg ccagtggcga taagtcgtgt    2820
cttaccgggt tggactcaag acgatagtta ccggataagg cgcagcggtc gggctgaacg    2880
gggggttcgt gcacacagcc cagcttggag cgaacgacct acaccgaact gagataccta    2940
cagcgtgagc tatgagaaag cgccacgctt cccgaaggga gaaaggcgga caggtatccg    3000
gtaagcggca gggtcggaac aggagagcgc acgagggagc ttccaggggg aaacgcctgg    3060
tatctttata gtcctgtcgg gtttcgccac ctctgacttg agcgtcgatt tttgtgatgc    3120
tcgtcagggg gcggagcct atggaaaaac gccagcaacg cggccttttt acggttcctg    3180
gccttttgct ggccttttgc tcacatgttc tttcctgcgt tatcccctga ttctgtggat    3240
aaccgtatta ccgcctttga gtgagctgat accgctcgcc gcagccgaac gaccgagcgc    3300
agcgagtcag tgagcgagga agcggaagag cgcccaatac gcaaaccgcc tctccccgcg    3360
cgttggccga ttcattaatg cagctggcac gacaggtttc ccgactggaa agcgggcagt    3420
gagcgcaacg caattaatgt gagttagctc actcattagg caccccaggc tttacacttt    3480
atgcttccgg ctcgtatgtt gtgtggaatt gtgagcggat aacaatttca cacaggaaac    3540
agctatgaca tgattacgaa ttgcaacgat ttaggtgaca ctatagaaga gaaggaatta    3600
atacgactca ctatagggag agagagagaa ttaccctcac taagggagg agaagcatga    3660 attcaaggta ccagatctta gttattaata gtaatcaatt acgggtcat tagttcatag    3720 cccatatatg gagttccgcg ttacataact tacggtaaat ggcccgcctg gctgaccgcc    3780
caacgacccc cgcccattga cgtcaataat gacgtatgtt cccatagtaa cgccaatagg    3840
gactttccat tgacgtcaat gggtggagta tttacggtaa actgcccact tggcagtaca    3900
tcaagtgtat catatgccaa gtacgccccc tattgacgtc aatgacggta aatggcccgc    3960
ctggcattat gcccagtaca tgaccttatg ggactttcct acttggcagt acatctacgt    4020
attagtcatc gctattacca tggtgatgcg gttttggcag tacatcaatg ggcgtggata    4080
gcggtttgac tcacggggat ttccaagtct ccaccccatt gacgtcaatg ggagtttgtt    4140
ttggcaccaa aatcaacggg actttccaaa atgtcgtaac aactccgccc cattgacgca    4200
aatgggcggt aggcgtgtac ggtgggaggt ctatataagc agagctggtt tagtgaaccg    4260
tggatccacc atgaagacg ccaaaaacat aaagaaaggc ccggcgccat tctatcctct    4320
agaggatgga accgctggag agcaactgca taaggctatg aagagatacg ccctggttcc    4380
tggaacaatt gcttttacag atgcacatat cgaggtgaac atcacgtacg cggaatactt    4440
cgaaatgtcc gttcggttgg cagaagctat gaaacgatat gggctgaata caaatcacag    4500
aatcgtcgta tgcagtgaaa actctcttca attctttatg ccggtgttgg gcgcgttatt    4560
tatcggagtt gcagttgcgc ccgcgaacga catttataat gaacgtgaat tgctcaacag    4620
tatgaacatt tcgcagccta ccgtagtgtt tgtttccaaa aaggggttgc aaaaaatttt    4680
gaacgtgcaa aaaaaattac caataatcca gaaaattatt atcatggatt ctaaaacgga    4740
ttaccaggga tttcagtcga tgtacacgtt cgtcacatct catctacctc ccggttttaa    4800
```

```
tgaatacgat tttgtaccag agtcctttga tcgtgacaaa acaattgcac tgataatgaa    4860
ttcctctgga tctactgggt tacctaaggg tgtggccctt ccgcatagaa ctgcctgcgt    4920
cagattctcg catgccagag atcctatttt tggcaatcaa atcgttccgg atactgcgat    4980
tttaagtgtt gtcccattcc atcacggttt tggaatgttt actacactcg gatatttgat    5040
atgtggattt cgagtcgtct taatgtatag atttgaagaa gagctgtttt tacgatccct    5100
tcaggattac aaaattcaaa gtgcgttgct agtaccaacc ctattttcat tcttcgccaa    5160
aagcactctg attgacaaat acgatttatc taatttacac gaaattgctt ctggggcgc     5220
acctctttcg aaagaagtcg gggaagcggt tgcaaaacgc ttccatcttc cagggatacg    5280
acaaggatat gggctcactg agactacatc agctattctg attacacccg aggggatga    5340
taaaccgggc gcgtcggta aagttgttcc attttttgaa gcgaaggttg tggatctgga    5400
taccgggaaa acgctgggcg ttaatcagag aggcgaatta tgtgtcagag gacctatgat    5460
tatgtccggt tatgtaaaca atccggaagc gaccaacgcc ttgattgaca aggatggatg    5520
gctacattct ggagacatag cttactggga cgaagacgaa cacttcttca tagttgaccg    5580
cttgaagtct ttaattaaat acaaaggata tcaggtggcc cccgctgaat tggaatcgat    5640
attgttacaa caccccaaca tcttcgacgc gggcgtggca ggtcttcccg acgatgacgc    5700
cggtgaactt cccgccgccg ttgttgtttt ggagcacgga agacgatga cggaaaaaga    5760
gatcgtggat tacgtcgcca gtcaagtaac aaccgcgaaa aagttgcgcg gaggagttgt    5820
gtttgtggac gaagtaccga aaggtcttac cggaaaactc gacgcaagaa aaatcagaga    5880
gatcctcata aaggccaaga agggcggaaa gtccaaattg ctcgagtgat gaaagctgcg    5940
cactagtaac tatacaacct actacctcaa agcttaataa aggatctttt attttcattg    6000
gatctgtgtg ttggttttt gtatgcggcc gctagcttgg cactggccgt cgttttacaa    6060
cgtcgtgact gggaaaaccc tggcgttacc caacttaatc gccttgcagc acatcccct    6120
ttcgccagct ggcgtaatag cgaagaggcc cgcaccgatc gcccttccca acagttgcgc    6180
agcctgaatg gcgaatggcg cctgatgcgg tattttctcc ttacgcatct gtgcggtatt    6240
tcacaccgca tatggtgcac tctcagtaca atctgctctg atgccgcata gttaagccag    6300
ccccgacacc cgccaacacc cgctgacgcg ccctgacggg cttgtctgct cccggcatcc    6360
gcttacagac aagctgtgac cgtctccggg agctgcatgt gtcagaggtt ttcaccgtca    6420
tcaccgaaac gcgcga                                                    6436
```

<210> SEQ ID NO 109
<211> LENGTH: 6436
<212> TYPE: DNA
<213> ORGANISM: Artificial Sequence
<220> FEATURE:
<223> OTHER INFORMATION: pMIR-REPORT-Luciferase_hsa-let-7c-5p

<400> SEQUENCE: 109

```
gacgaaagat tggtgtggaa agtccccagg ctccccagca ggcagaagta tgcaaagcat      60
gcatctcaat tagtcagcaa ccaggtgtgg aaagtcccca ggctccccag caggcagaag     120
tatgcaaagc atgcatctca attagtcagc aaccatagtc cgcccctaa ctccgcccat      180
cccgccccta actccgccca gttccgccca ttctccgccc catggctgac taatttttt      240
tatttatgca gaggccgagg ccgcctcggc ctctgagcta ttccagaagt agtgaggagg     300
ctttttgga ggcctaggct tttgcaaaaa gctagcttgc atgcctgcag gtcggccgcc      360
acgaccggtg ccgccaccat cccctgaccc acgcccctga ccctcacaa ggagacgacc      420
```

```
ttccatgacc gagtacaagc ccacggtgcg cctcgccacc cgcgacgacg tcccccgggc    480
cgtacgcacc ctcgccgccg cgttcgccga ctaccccgcc acgcgccaca ccgtcgaccc    540
ggaccgccac atcgagcggg tcaccgagct gcaagaactc ttcctcacgc gcgtcgggct    600
cgacatcggc aaggtgtggg tcgcggacga cggcgccgcg gtggcggtct ggaccacgcc    660
ggagagcgtc gaagcggggg cggtgttcgc cgagatcggc ccgcgcatgg ccgagttgag    720
cggttcccgg ctggccgcgc agcaacagat ggaaggcctc ctggcgccgc accggcccaa    780
ggagcccgcg tggttcctgg ccaccgtcgg cgtctcgccc gaccaccagg gcaagggtct    840
gggcagcgcc gtcgtgctcc ccggagtgga ggcggccgag cgcgccgggg tgcccgcctt    900
cctggagacc tccgcgcccc gcaacctccc cttctacgag cggctcggct tcaccgtcac    960
cgccgacgtc gaggtgcccg aaggaccgcg cacctggtgc atgacccgca agcccggtgc    1020
ctgacgcccg ccccacgacc cgcagcgccc gaccgaaagg agcgcacgac cccatggctc    1080
cgaccgaagc cacccggggc ggccccgccg acccgcacc cgcccccgag gcccaccgac    1140
tctagaggat cataatcagc ataccacat ttgtagaggt tttacttgct ttaaaaaacc    1200
tcccacacct cccctgaac ctgaaacata aatgaatgc aattgttgtt gttaacttgt    1260
ttattgcagc ttataatggt tacaaataaa gcaatagcat cacaaatttc acaaataaag    1320 cattttttc actgcaatct cgtgatacgc ctattttat aggttaatgt catgataata    1380
atggtttctt agacgtcagg tggcactttt cggggaaatg tgcgcggaac ccctatttgt    1440 ttattttct aaatacattc aaatatgtat ccgctcatga caataaacc ctgataaatg    1500 cttcaataat attgaaaaag gaagagtatg agtattcaac atttccgtgt cgcccttatt    1560 ccctttttg cggcattttg ccttcctgtt tttgctcacc cagaaacgct ggtgaaagta    1620
aaagatgctg aagatcagtt gggtgcacga gtgggttaca tcgaactgga tctcaacagc    1680
ggtaagatcc ttgagagttt tcgccccgaa gaacgttttc caatgatgag cactttaaaa    1740
gttctgctat gtggcgcggt attatcccgt attgacgccg ggcaagagca actcggtcgc    1800
cgcatacact attctcagaa tgacttggtt gagtactcac cagtcacaga aaagcatctt    1860
acggatggca tgacagtaag agaattatgc agtgctgcca taaccatgag tgataacact    1920
gcggccaact tacttctgac aacgatcgga ggaccgaagg agctaaccgc ttttttgcac    1980
aacatggggg atcatgtaac tcgccttgat cgttgggaac cggagctgaa tgaagccata    2040
ccaaacgacg agcgtgacac cacgatgcct gtagcaatgg caacaacgtt gcgcaaacta    2100
ttaactggcg aactacttac tctagcttcc cggcaacaat taatagactg gatggaggcg    2160
gataaagttg caggaccact tctgcgctcg gcccttccgg ctggctggtt tattgctgat    2220
aaatctggag ccggtgagcg tgggtctcgc ggtatcattg cagcactggg gccagatggt    2280
aagccctccc gtatcgtagt tatctacacg acggggagtc aggcaactat ggatgaacga    2340
aatagacaga tcgctgagat aggtgcctca ctgattaagc attggtaact gtcagaccaa    2400
gtttactcat atatacttta gattgattta aaacttcatt tttaatttaa aaggatctag    2460
gtgaagatcc tttttgataa tctcatgacc aaaatccctt aacgtgagtt ttcgttccac    2520
tgagcgtcag accccgtaga aaagatcaaa ggatcttctt gagatccttt ttttctgcgc    2580
gtaatctgct gcttgcaaac aaaaaaacca ccgctaccag cggtggtttt tttgccggat    2640
caagagctac caactctttt tccgaaggta actggcttca gcagagcgca gataccaaat    2700
actgttcttc tagtgtagcc gtagttaggc caccacttca agaactctgt agcaccgcct    2760
```

```
acatacctcg ctctgctaat cctgttacca gtggctgctg ccagtggcga taagtcgtgt    2820
cttaccgggt tggactcaag acgatagtta ccggataagg cgcagcggtc gggctgaacg    2880
gggggttcgt gcacacagcc cagcttggag cgaacgacct acaccgaact gagataccta    2940
cagcgtgagc tatgagaaag cgccacgctt cccgaaggga gaaaggcgga caggtatccg    3000
gtaagcggca gggtcggaac aggagagcgc acgagggagc ttccaggggg aaacgcctgg    3060
tatctttata gtcctgtcgg gtttcgccac ctctgacttg agcgtcgatt tttgtgatgc    3120
tcgtcagggg ggcggagcct atggaaaaac gccagcaacg cggcctttttt acggttcctg    3180
gccttttgct ggccttttgc tcacatgttc tttcctgcgt tatcccctga ttctgtggat    3240
aaccgtatta ccgcctttga gtgagctgat accgctcgcc gcagccgaac gaccgagcgc    3300
agcgagtcag tgagcgagga agcggaagag cgcccaatac gcaaaccgcc tctccccgcg    3360
cgttggccga ttcattaatg cagctggcac gacaggtttc ccgactggaa agcgggcagt    3420
gagcgcaacg caattaatgt gagttagctc actcattagg caccccaggc tttacacttt    3480
atgcttccgg ctcgtatgtt gtgtggaatt gtgagcggat aacaatttca cacaggaaac    3540
agctatgaca tgattacgaa ttgcaacgat ttaggtgaca ctatagaaga aaggaatta    3600
atacgactca ctatagggag agagagagaa ttaccctcac taaagggagg agaagcatga    3660
attcaaggta ccagatctta gttattaata gtaatcaatt acgggtcat tagttcatag    3720
cccatatatg gagttccgcg ttacataact tacggtaaat ggcccgcctg gctgaccgcc    3780
caacgacccc cgcccattga cgtcaataat gacgtatgtt cccatagtaa cgccaatagg    3840
gactttccat tgacgtcaat gggtggagta tttacggtaa actgcccact ggcagtaca    3900
tcaagtgtat catatgccaa gtacgccccc tattgacgtc aatgacggta atggcccgc    3960
ctggcattat gcccagtaca tgaccttatg ggactttcct acttggcagt acatctacgt    4020
attagtcatc gctattacca tggtgatgcg gttttggcag tacatcaatg ggcgtggata    4080
gcggtttgac tcacggggat ttccaagtct ccacccccatt gacgtcaatg ggagtttgtt    4140
ttggcaccaa aatcaacggg actttccaaa atgtcgtaac aactccgccc cattgacgca    4200
aatgggcggt aggcgtgtac ggtgggaggt ctatataagc agagctggtt tagtgaaccg    4260
tggatccacc atggaagacg ccaaaaacat aaagaaaggc ccggcgccat tctatcctct    4320
agaggatgga accgctggag agcaactgca taaggctatg aagagatacg ccctggttcc    4380
tggaacaatt gcttttacag atgcacatat cgaggtgaac atcacgtacg cggaatactt    4440
cgaaatgtcc gttcggttgg cagaagctat gaaacgatat gggctgaata caaatcacag    4500
aatcgtcgta tgcagtgaaa actctcttca attctttatg ccggtgttgg gcgcgttatt    4560
tatcggagtt gcagttgcgc ccgcgaacga catttataat gaacgtgaat tgctcaacag    4620
tatgaacatt tcgcagccta ccgtagtgtt tgtttccaaa aaggggttgc aaaaaatttt    4680
gaacgtgcaa aaaaaattac caataatcca gaaaattatt atcatggatt ctaaaacgga    4740
ttaccaggga tttcagtcga tgtacacgtt cgtcacatct catctacctc ccggttttaa    4800
tgaatacgat tttgtaccag agtcctttga tcgtgacaaa acaattgcac tgataatgaa    4860
ttcctctgga tctactgggt tacctaaggg tgtggccctt ccgcatagaa ctgcctgcgt    4920
cagattctcg catgccagag atcctatttt tggcaatcaa atcgttccgg atactgcgat    4980
tttaagtgtt gtcccattcc atcacggttt tggaatgttt actacactcg gatatttgat    5040
atgtggattt cgagtcgtct taatgtatag atttgaagaa gagctgtttt tacgatcct    5100
tcaggattac aaaattcaaa gtgcgttgct agtaccaacc ctattttcat tcttcgccaa    5160
```

```
aagcactctg attgacaaat acgatttatc taatttacac gaaattgctt ctgggggcgc      5220
acctctttcg aaagaagtcg gggaagcggt tgcaaaacgc ttccatcttc cagggatacg      5280
acaaggatat gggctcactg agactacatc agctattctg attacacccg aggggggatga    5340 taaaccgggc gcggtcggta aagttgttcc attttttgaa gcgaaggttg tggatctgga      5400
taccgggaaa acgctgggcg ttaatcagag aggcgaatta tgtgtcagag gacctatgat     5460
tatgtccggt tatgtaaaca atccggaagc gaccaacgcc ttgattgaca aggatggatg      5520
gctacattct ggagacatag cttactggga cgaagacgaa cacttcttca tagttgaccg      5580
cttgaagtct ttaattaaat acaaaggata tcaggtggcc cccgctgaat tggaatcgat      5640
attgttacaa caccccaaca tcttcgacgc gggcgtggca ggtcttcccg acgatgacgc      5700
cggtgaactt cccgccgccg ttgttgtttt ggagcacgga aagacgatga cggaaaaaga     5760
gatcgtggat tacgtcgcca gtcaagtaac aaccgcgaaa aagttgcgcg gaggagttgt      5820
gtttgtggac gaagtaccga aaggtcttac cggaaaactc gacgcaagaa aaatcagaga     5880
gatcctcata aaggccaaga agggcggaaa gtccaaattg ctcgagtgat gaaagctgcg     5940
cactagtaac catacaacct actacctcaa agcttaataa aggatctttt attttcattg     6000
gatctgtgtg ttggttttt gtatgcggcc gctagcttgg cactggccgt cgttttacaa      6060
cgtcgtgact gggaaaaccc tggcgttacc caacttaatc gccttgcagc acatcccct      6120 ttcgccagct ggcgtaatag cgaagaggcc cgcaccgatc gcccttccca acagttgcgc     6180
agcctgaatg gcgaatggcg cctgatgcgg tattttctcc ttacgcatct gtgcggtatt    6240
tcacaccgca tatggtgcac tctcagtaca atctgctctg atgccgcata gttaagccag     6300
ccccgacacc cgccaacacc cgctgacgcg ccctgacggg cttgtctgct cccggcatcc     6360
gcttacagac aagctgtgac cgtctccggg agctgcatgt gtcagaggtt ttcaccgtca     6420
tcaccgaaac gcgcga                                                    6436
```